US011676719B2

(12) United States Patent
Feczko et al.

(10) Patent No.: US 11,676,719 B2
(45) Date of Patent: Jun. 13, 2023

(54) SUBTYPING HETEROGENEOUS DISORDERS USING FUNCTIONAL RANDOM FOREST MODELS

(71) Applicant: Oregon Health & Science University, Portland, OR (US)

(72) Inventors: Eric Feczko, Portland, OR (US); Damien A. Fair, Portland, OR (US); Shannon McWeeney, Portland, OR (US)

(73) Assignee: Oregon Health & Science University, Portland, OR (US)

(*) Notice: Subject to any disclaimer, the term of this patent is extended or adjusted under 35 U.S.C. 154(b) by 671 days.

(21) Appl. No.: 16/721,512

(22) Filed: Dec. 19, 2019

(65) Prior Publication Data

US 2020/0219619 A1    Jul. 9, 2020

Related U.S. Application Data

(60) Provisional application No. 62/783,023, filed on Dec. 20, 2018.

(51) Int. Cl.
*G16H 50/20* (2018.01)
*G16H 20/70* (2018.01)
(Continued)

(52) U.S. Cl.
CPC .............. *G16H 50/20* (2018.01); *G06N 5/01* (2023.01); *G06N 20/20* (2019.01); *G16H 20/70* (2018.01)

(58) Field of Classification Search
CPC ......... G16H 10/00–80/00; G06N 3/00–99/007
See application file for complete search history.

(56) References Cited

U.S. PATENT DOCUMENTS

2010/0143318 A1* 6/2010 Johnson ............... C12Q 1/6883
435/6.12
2012/0094315 A1* 4/2012 Fryar-Williams ...........................
G01N 33/6896
204/464
(Continued)

FOREIGN PATENT DOCUMENTS

WO WO-2017201323 A1 * 11/2017 ......... A61B 5/02055

OTHER PUBLICATIONS

Chen et al, "Towards Autism subtypes? Unsupervised machine learning using fcMRI features," Conference: Organization of Human Brain Mapping • At: Honolulu, Hawaii, Jun. 2015. (Year: 2015).*
(Continued)

*Primary Examiner* — Jonathon A. Szumny
(74) *Attorney, Agent, or Firm* — Katherine M. Mead; Tanya M. Harding; Lee & Hayes, P.C.

(57) ABSTRACT

An example method includes identifying training data indicating features of a sample population and clinical outcomes of the sample population. The clinical outcomes are associated with a heterogeneous condition. The method further includes generating decision trees in a Random Forest (RF) based on the training data, each one of the decision trees being configured to divide the sample population into multiple categories based on the features of the sample population. In response to generating the decision trees, a proximity matrix comprising multiple entries is generated using the RF. One of the entries indicates a proportion of the decision trees that categorize a first individual among the sample population and a second individual among the sample population into the same categories among the multiple categories. The method further includes identifying subgroups of the heterogeneous condition by detecting communities of the proximity matrix.

18 Claims, 47 Drawing Sheets
(32 of 47 Drawing Sheet(s) Filed in Color)

(51) Int. Cl.
G06N 20/20 (2019.01)
G06N 5/01 (2023.01)

(56) References Cited

U.S. PATENT DOCUMENTS

| | | | | |
|---|---|---|---|---|
| 2014/0057244 | A1* | 2/2014 | Roots | G09B 19/00 |
| | | | | 434/362 |
| 2014/0065132 | A1* | 3/2014 | Hsiao | A61P 43/00 |
| | | | | 435/7.92 |
| 2015/0377906 | A1* | 12/2015 | Wyrobek | G01N 21/00 |
| | | | | 702/19 |
| 2018/0104313 | A1* | 4/2018 | Kohtz | A61P 25/00 |
| 2018/0330824 | A1* | 11/2018 | Athey | G16H 50/70 |
| 2019/0019581 | A1* | 1/2019 | Vaughan | A61B 5/168 |
| 2019/0110753 | A1* | 4/2019 | Zhang | G06N 3/084 |
| 2020/0305706 | A1* | 10/2020 | Amil Marletti | G16H 50/70 |

OTHER PUBLICATIONS

Chanoud Arthur Nasamran, "Clustering Analysis of Resting-State Functional MRI Data To Identify Possible Subtypes of Autism Spectrum Disorder" A Thesis Presented to the Faculty of San Diego State University, In Partial Fulfillment of the Requirements for the Degree Master of Science—Summer 2017 (Year: 2017).*

Gray et al., "Random forest-based similarity measures for multimodal classification of Alzheimer's disease," NeuroImage 65 (2013) 167-175 (Year: 2013).*

Sim et al., "Random Forests on Distance Matrices for Imaging Genetics Studies," Statistical Applications in Genetics and Molecular Biology, vol. 12 Issue 6, 2013 (Year: 2013).*

Shen et al., "Using Cluster Ensemble and Validation to Identify Subtypes of Pervasive Developmental Disorder," AMIA 2007 Symposium Proceedings, pp. 666-670. (Year: 2007).*

Boland et al., "Development and validation of a classification approach for extracting severity automatically from electronic health records," Journal of Biomedical Semantics (2015) 6:14 (Year: 2015).*

Vaiciukynas E, Verikas A, Gelzinis A, BacauskieneM (2017) "Detecting Parkinson's disease from sustained phonation and speech signals." PLoS ONE 12(10): e0185613. https://doi. (Year: 2017).*

Conrad DJ, Bailey BA (2015) "Multidimensional Clinical Phenotyping of an Adult Cystic Fibrosis Patient Population." PLoS ONE 10(3): e0122705. doi:10.1371/journal.pone.0122705. (Year: 2015).*

Daniel Oehm, "Unsupervised Random Forest Example," https://gradientdescending.com/unsupervised-random-forest-example/, 2018. (Year: 2018).*

Grossi et al., "Pregnancy risk factors in autism: a pilot study with artificial neural networks," Pediatric Research, vol. 79 | No. 2 | Feb. 2016 (Year: 2016).*

Duygu Ozcelik, "A Weakly Supervised Clustering Method for Cancer Subgroup Identification," A thesis submitted to the graduate school of engineering and science of Bilkent University in partial fulfillment of the requirements for the degree of Master of Science in Computer Engineering, Jul. 2016. (Year: 2016).*

Davis, et al., "Prenatal maternal stress programs infant stress regulation," Journal of Child Psychology and Psychiatry, vol. 52, No. 2, Feb. 2011, pp. 119-129.

De Weerth and Buitelaar, "Cortisol awakening response in pregnant women," Psychoneuroendocrinology, vol. 30, No. 3, Oct. 2005, pp. 902-907 (abstract).

Demurie, et al., "Domain-general and domain-specific aspects of temporal discounting in children with ADHD and autism spectrum disorders (ASD): A proof of concept study," Research in Developmental Disabilities, vol. 34, No. 6, Jun. 2013, pp. 1870-1880.

Demurie, et al., "Temporal discounting of monetary rewards in children and adolescents with ADHD and autism spectrum disorders," Developmental Science, vol. 15, No. 6, Nov. 2012, pp. 791-800 (abstract).

Di Martino, et al., "The autism brain imaging data exchange: towards a large-scale evaluation of the intrinsic brain architecture in autism," Molecular Psychiatry, vol. 19, Jun. 2014, pp. 659-667.

Diamond, "Executive functions" Annual Review of Psychology, vol. 64, Jan. 2013, pp. 135-168.

Dias, et al., "Characterizing heterogeneity in children with and without ADHD based on reward system connectivity," Developmental Cognitive Neuroscience, vol. 11, Feb. 2015, pp. 155-174.

Dierker, et al., "Analysis of Cortical Shape in Children with Simplex Autism," Cerebral Cortex, vol. 25, No. 4, Apr. 2015, pp. 1042-1051.

Doshi, et al., "Economic Impact of Childhood and Adult Attention-Deficit/Hyperactivity Disorder in the United States," Journal of the American Academy of Child & Adolescent Psychiatry, vol. 51, No. 10, Oct. 2012, pp. 990-1002.e2.

Duba, et al., "Use of machine learning for behavioral distinction of autism and ADHD," Translational Psychiatry, vol. 6, No. 732, Feb. 2016, 5 pages.

Duchesnay, et al., "Feature selection and classification of imbalanced datasets: Application to PET images of children with autistic spectrum disorders," NeuroImage, vol. 57, No. 3, Aug. 2011, pp. 1003-1014.

Eggebrecht, et al., "Joint Attention and Brain Functional Connectivity in Infants and Toddlers," Cerebral Cortex, vol. 27, No. 3, Mar. 2017, pp. 1709-1720.

Entringer, et al., "Attenuation of maternal psychophysiological stress responses and the maternal cortisol awakening response over the course of human pregnancy," The International Journal on the Biology of Stress, vol. 13, No. 3, Jan. 2010, pp. 258-268 (21 pgs).

Entringer, et al., "Prenatal stress and developmental programming of human health and disease risk: concepts and Integration of empirical findings," Current Opinion in Endocrinology, Diabetes & Obesity, vol. 17, No. 6, 2010, pp. 507-516 (18 pgs).

Etkin and Wager, "Functional Neuroimaging of Anxiety: A Meta-Analysis of Emotional Processing in PTSD, Social Anxiety Disorder, and Specific Phobia," American Journal of Psychiatry, vol. 164, No. 10, Oct. 2007, pp. 1476-1488.

Fair, et al., "Development of distinct control networks through segregation and integration," PNAS USA, vol. 104, No. 33, Aug. 2007, pp. 13507-13512.

Fair, et al., "Distinct neural signatures detected for ADHD subtypes after controlling for micro-movements in resting state functional connectivity MRI data," Frontiers in System Neuroscience, vol. 6, No. 80, Feb. 2013, 31 pages.

Faja, et al., "Executive function predicts the development of play skills for verbal preschoolers with autism spectrum disorders," Autism Research, vol. 9, No. 12, Dec. 2016, pp. 1274-1284.

Feczko, et al., "Subtyping cognitive profiles in Autism Spectrum Disorder using a Functional Random Forest algorithm," Neuroimage, vol. 172, May 2018, pp. 674-688.

Feczko, et al., "The hemodynamic response in children with Simplex Autism," Developmental Cognitive Neuroscience, vol. 2, No. 4, Oct. 2012, pp. 396-408.

Feczko, et al., "The Heterogeneity Problem: Approaches to Identify Psychiatric Subtypes," Trends in Cognitive Sciences, vol. 23, No. 7, Jul. 2019, pp. 584 601.

Filiou and Turek, "Chapter 1—General overview: Biomarkers in neuroscience research," International Review of Neurobiology, vol. 101, Oct. 2011, pp. 2-17.

Fischl, "FreeSurfer," Neuroimage, vol. 62, No. 2, Aug. 2012, pp. 774-781 (18 pgs).

Fombonne, "The Prevalence of Autism," JAMA, vol. 289, No. 1, Jan. 2003, pp. 87-89.

Fonov, et al., "Unbiased average age-appropriate atlases for pediatric studies," Neuroimage, vol. 54, No. 1, Jan. 2011, pp. 313-327 (34 pgs).

Fox and Raichle, "Spontaneous fluctuations in brain activity observed with functional magnetic resonance imaging," Nature Reviews Neuroscience, vol. 8, Sep. 2007, pp. 700-711.

Fox, et al., "The human brain is intrinsically organized into dynamic, anticorrelated functional networks," PNAS USA, vol. 102, No. 27, Jul. 2005, pp. 9673-9678.

(56) References Cited

OTHER PUBLICATIONS

Friedman and Miyake, "Unity and diversity of executive functions: Individual differences as a window on cognitive structure," Cortex, vol. 86, Jan. 2017, pp. 186-204 (36 pgs).
Galera, et al., "Childhood and adolescent hyperactivity-inattention symptoms and academic achievement 8 years later: the GAZEL Youth study," Psychological Medicine, vol. 39, No. 11, Apr. 2009, pp. 1895-1906.
Gao, et al., "Development of human brain cortical network architecture during infancy," Brain Structure and Function, vol. 220, No. 2, Mar. 2015, pp. 1173-1186 (25 pgs).
Gardiner and Iarocci, "Everyday executive function predicts adaptive and internalizing behavior among children with and without autism spectrum disorder," Autism Research, vol. 11, No. 2, Feb. 2018, pp. 284-295.
Geurts, et al., "How specific are executive functioning deficits in attention deficit hyperactivity disorder and autism?," Journal of Child Psychology and Psychiatry and Allied Disciplines, vol. 45, No. 4, May 2004, pp. 836-854.
Geurts, et al., "Prepotent Response Inhibition and Interference Control in Autism Spectrum Disorders: Two Meta-Analyses," Autism Research, vol. 7, No. 4, Aug. 2014, pp. 407-420 (49 pgs).
Glasser, et al., "The minimal preprocessing pipelines for the Human Connectome Project," Neuroimage, vol. 80, Oct. 2013, pp. 105-124.
Glynn, et al., "Pattern of perceived stress and anxiety in pregnancy predicts preterm birth," Health Psychology, vol. 27, No. 1, Jan. 2008, pp. 43-51.
Glynn, et al., "Postnatal maternal cortisol levels predict temperament in healthy breastfed infants," Early Human Development, vol. 83, No. 10, Oct. 2007, pp. 675-681.
Gold, et al., "Amygdala-Cortical Connectivity Associations with Anxiety, Development, and Threat," vol. 33, No. 10, Oct. 2016, pp. 917-926.
Gordon, et al., "Generation and Evaluation of a Cortical Area Parcellation from Resting-State Correlations," Cerebral Cortex, vol. 24, No. 12, Dec. 2014, pp. 3350-3364.
Gotts, et al., "The perils of global signal regression for group comparisons a case study of Autism Spectrum Disorders," Frontiers in Human Neuroscience, vol. 7, Jul. 2013, 20 pages.
Graham, et al., "Implications of newborn amygdala connectivity for fear and cognitive development at 6-months-of-age," Developmental Cognitive Neuroscience, vol. 18, Apr. 2016, pp. 12-25.
Graham, et al., "Maternal Systemic Interleukin-6 During Pregnancy Is Associated With Newborn Amygdala Phenotypes and Subsequent Behavior at 2 Years of Age," Biological Psychiatry, vol. 53, No. 2, Jan. 2018, pp. 109-119.
Green and Swets, "Signal Detection Theory and Psychophysics," retrieved on Aug. 27, 2021, retrieved from <<http://andrei.gorea.free.fr/Teaching_fichiers/SDT%20and%20Psytchophysics.pdf>>, 1966, 45 pages.
Hahn, et al., "Reduced resting-state functional connectivity between amygdala and orbitofrontal cortex in social anxiety disorder," Neuroimage, vol. 56, No. 3, Jun. 2011, pp. 881-889.
Hall and Heckman, "Estimating and depicting the structure of a distribution of random functions," Biometrika, vol. 89, No. 1, Mar. 2002, pp. 145-158.
Hefter, et al., "Perception of facial expression and facial identity in subjects with social developmental disorders," Neurology, vol. 65, No. 10, Nov. 2005, pp. 1620-1625.
Heitz, "The speed-accuracy tradeoff: history, physiology, methodology, and behavior," Neuroscience, vol. 8, Jun. 2014, 19 pages.
Herringa, et al., "Childhood maltreatment is associated with altered fear circuitry and increased internalizing symptoms by late adolescence," PNAS USA, vol. 110, No. 47, Nov. 2013, pp. 19119-19124.
Hiess, et al., "Corpus Callosum Area and Brain Volume in Autism Spectrum Disorder: Quantitative Analysis of Structural MRI from the ABIDE Database," Journal of Autism and Developmental Disorders, vol. 43, Oct. 2015, pp. 3107-3114.
Hill, "Executive dysfunction in autism," Trends in cognitive Sciences, vol. 8, No. 1, Jan. 2004, pp. 26-32.

Holmes and Patrick, "The Myth of Optimality in Clinical Neuroscience," Trends in Cognitive Sciences, vol. 22, No. 3, Mar. 2018, pp. 241-257.
Abraham, et al., "Deriving reproducible biomarkers from multi-site resting-state data: An Autism-based example," NeuroImage, vol. 147, Nov. 2016 / Feb. 2017, pp. 1-19.
Adams and Jarrold, "Inhibition in Autism: Children with Autism have Difficulty Inhibiting Irrelevant Distractors but not Prepotent Responses," Journal of Autism and Developmental Disorders, vol. 42, No. 6, Jun. 2012, pp. 1052-1063.
Ahmed, et al., "Trajectories of maternal depressive and anxiety symptoms from pregnancy to five years postpartum and their prenatal predictors," BMC Pregnancy and Childbirth, vol. 19, No. 26, Jan. 2019, 10 pages.
Alexander & Nitz, "Retrosplenial cortex maps the conjunction of internal and external spaces," Nature Neuroscience, vol. 18, No. 8, Aug. 2015, pp. 1143-1151 (abstract).
Amaral, et al., "Neuroanatomy of autism," Trends in Neuroscience, vol. 31, No. 3, Mar. 2008, pp. 137-145.
Anderson, et al., "Decreased Interhemispheric Functional Connectivity in Autism," Cerebral Cortex, vol. 21, No. 5, May 2011, pp. 1134-1146.
Andescavage, et al., "Complex Trajectories of Brain Development in the Healthy Human Fetus," Cerebral Cortex, vol. 27, No. 11, Nov. 2017, pp. 5274-5283.
Baddeley, "Working memory: looking back and looking forward," Nature Reviews Neuroscience, vol. 4, No. 10, Oct. 2003, pp. 829-839.
Banks, et al., "Amygdala-frontal connectivity during emotion regulation," Social Cognitive and Affective Neuroscience, vol. 2, No. 4, Dec. 2007, pp. 303-312.
Braga & Buckner, "Parallel Interdigitated Distributed Networks within the Individual Estimated by Intrinsic Functional Connectivity," Neuron, vol. 95, No. 2, Jul. 2017, pp. 457-471.e5.
Barkley, "Behavioral inhibition, sustained attention, and executive functions: constructing a unifying theory of ADHD," Psychological bulletin, vol. 121, No. 1, Jan. 1997, pp. 65-94.
Barton, et al., "Are patients with social developmental disorders prosopagnosic? Perceptual heterogeneity in the Asperger and socio-emotional processing disorders," Brain, vol. 127, No. 8, Aug. 2004, pp. 1706-1716.
Bathelt, et al., "Data-Driven Subtyping of Executive Function-Related Behavioral Problems in Children," Journal of the American Academy of Child & Adolescent Psychiatry, vol. 57, No. 4, Apr. 2018, pp. 252-262.e4.
Bebko, et al., "The McGurk effect in children with autism and Asperger syndrome," Autism Research, vol. 7, No. 1, Feb. 2017, pp. 50-59.
Begeer, et al., "False-Belief Understanding and Social Preference Over the First 2 Years of School: A Longitudinal Study," Child Development, vol. 85, No. 6, Nov./Dec. 2014, pp. 2389-2403.
Bennetto, et al., "Intact and Impaired Memory Functions in Autism," Child Development, vol. 67, No. 4, Aug. 1996, pp. 1816-1835 (abstract).
Berenguer, et al., "Children with autism and attention deficit hyperactivity disorder. Relationships between symptoms and executive function, theory of mind, and behavioral problems," Research in Developmental Disabilities, vol. 83, Dec. 2018, pp. 1-26.
Betancur, et al., "Etiological heterogeneity in autism spectrum disorders: more than 100 genetic and genomic disorders and still counting," Brain Research, vol. 1380, Mar. 2011, pp. 1-51.
Bowler, et al., "Nonverbal Short-Term Serial Order Memory in Autism Spectrum Disorder," Journal of Abnormal Psychology, vol. 125, No. 7, Oct. 2016, pp. 886-893.
Brambilla, et al., "Brain anatomy and development in autism: review of structural MRI studies," Brain Research Bulletin, vol. 61, No. 6, Oct. 2003, pp. 557-569.
Braunlich, et al., "Frontoparietal networks involved in categorization and item working memory," NeuroImage, vol. 107, Feb. 2015, pp. 146-162.

(56) References Cited

OTHER PUBLICATIONS

Braungart-Rieker, et al., "Fear and anger reactivity trajectories from 4 to 16 months: the roles of temperament, regulation, and maternal sensitivity," Developmental Psychology, vol. 46, No. 4, Jul. 2010, pp. 791-804.
Breiman and Cutler "Package 'randomForest'" retrieved on Aug. 27, 2021 retrieved from <<https://cran.r project.org/web/packages/randomForest/randomForest.pdf>>, 29 pages.
Breiman, "Random Forests," Machine Learning, vol. 45, Oct. 2001, pp. 5-32.
Breslau, et al., "Change in teachers' ratings of attention problems and subsequent change in academic achievement: a prospective analysis," Psychological Medicine, vol. 40, No. 1, Jun. 2009, pp. 159-166.
Brooker, et al., "The development of stranger fear in infancy and toddlerhood: normative development, individual differences, antecedents, and outcomes," Developmental Science, vol. 16, No. 6, Nov. 2013, pp. 864-878.
Brumback and Rice, "Smoothing Spline Models for the Analysis of Nested and Crossed Samples of Curves," Journal of the American Statistical Association, vol. 93, No. 443, Nov. 1998, 33 pages.
Burghy, et al., "Developmental pathways to amygdala-prefrontal function and internalizing symptoms in adolescence," Nature Neuroscience, vol. 15, No. 12, Dec. 2012, pp. 1736-1741.
Burton, et al., "The Glasgow Face Matching Test," Behavior Research Methods, vol. 42, Feb. 2012, pp. 286-291.
Buss, et al., "Maternal cortisol over the course of pregnancy and subsequent child amygdala and hippocampus volumes and affective problems," PNAS USA, vol. 109, No. 20, May 2012, pp. 1312-1319.
Buss, et al., "The Role of Stress in Brain Development: The Gestational Environment's Long-Term Effects on the Brain," Cerebrum, vol. 2012, Mar.-Apr. 2012, 16 pages.
Calderone, et al., "Comparing Alzheimer's and Parkinson's diseases networks using graph communities structure," BMC Systems Biology, (2016) 10:25, Mar. 2, 2016, pp. 1-10, https://doi.org/10.1186/s12918-016-0270-7.
Callaghan, et al., "The international society for developmental psychobiology Sackler symposium: Early adversity and the maturation of emotion circuits—A cross-species analysis," Developmental Psychobiology, vol. 56, No. 8, Dec. 2014, pp. 1635-1650.
Castellanos, et al., "Characterizing cognition in ADHD: beyond executive dysfunction," Trends in Cognitive Sciences, vol. 10, No. 3, Mar. 2006, pp. 117-123.
Cerliani, et al., "Increased Functional Connectivity Between Subcortical and Cortical Resting-State Networks in Autism Spectrum Disorder," JAMA Psychiatry, vol. 72, No. 8, Aug. 2015, pp. 767-777.
Chan, et al., "Assessment of executive functions: Review of instruments and identification of critical issues," Archives of Clinical Neuropsychology, vol. 23, No. 2, Mar. 2008, pp. 201-216.
Chantiluke, et al., "Disorder-specific functional abnormalities during temporal discounting in youth with Attention Deficit Hyperactivity Disorder (ADHD), Autism and comorbid ADHD and Autism," Psychiatry Research: Neuroimaging, vol. 223, No. 2, Aug. 2014, pp. 113-120.
Chen, et al., "Deficits in executive functions among youths with autism spectrum disorders: an age-stratified analysis," Psychological Medicine, vol. 46, No. 8, Mar. 2016, pp. 1625-1638.
Chen, et al., "Diagnostic classification of intrinsic functional connectivity highlights somatosensory, default mode, and visual regions in autism," NeuroImage: Clinical, vol. 8, Apr. 2015, pp. 238-245.
Chen, et al., "Structural MRI in autism spectrum disorder," Pediatric Research, vol. 69, No. 5, May 2011, pp. 63R-68R.
Cherkassky, et al., "Functional connectivity in a baseline resting-state network in autism," NeuroReport, vol. 17, No. 16, Nov. 2006, pp. 1687-1690.
Cohen, et al., "A global measure of perceived stress," Journal of Health and Social Behavior, vol. 24, No. 4, Dec. 1983, pp. 385-396.
Constantino and Charman, "Diagnosis of autism spectrum disorder: reconciling the syndrome, its diverse origins, and variation in expression," Neurology, vol. 15, No. 3, Mar. 2016, pp. 279-291.
Corbett and Constantine, "Autism and Attention Deficit Hyperactivity Disorder: Assessing Attention and Response Control with the Integrated Visual and Auditory Continuous Performance Test," Child Neuropsychology, vol. 12, No. 1-5, Aug. 2006, pp. 335-348.
Corbett, et al., "Examining executive functioning in children with autism spectrum disorder, attention deficit hyperactivity disorder and typical development," Psychiatry Research, vol. 166, No. 2-3, Apr. 2009, pp. 210-222.
Corbetta and Shulman, "Control of goal-directed and stimulus-driven attention in the brain," Nature Reviews Neuroscience, vol. 3, Mar. 2002, pp. 201-215.
Crippa, et al., "Use of Machine Learning to Identify Children with Autism and Their Motor Abnormalities," Journal of Autism and Developmental Disorders, vol. 45, Jul. 2015, pp. 2146-2156.
Critchfield and Kollins, "Temporal Discounting: Basic Research and the Analysis of Socially I,portant Behavior," Journal of Applied Behavior Analysis, vol. 34, No. 1, Feb. 2013, pp. 101-122.
Dajani, et al., "Investigating functional brain network integrity using a traditional and novel categorical scheme for neurodevelopmental disorders," Neuroimage: Clinical, vol. 21, Jan. 2019, 9 pages.
Murdaugh, et al., "Differential Deactivation during Mentalizing and Classification of Autism Based on Default Mode Network Connectivity," PLOS One, vol. 7, No. 11, Nov. 2012, 11 pages.
Musser, et al., "Shared familial transmission of autism spectrum and attention-deficit/hyperactivity disorders," Journal of Child Psychology and Psychiatry and Allied Disciplines, vol. 55, No. 7, Jul. 2014, pp. 819-827 (18 pgs).
Muthen and Muthen, "Mplus Statistical Analysis With Latent Variables User's Guide," retrieved on Aug. 27, 2021, retrieved from <<https://www.statmodel.com/download/usersguide/MplusUserGuideVer_8.pdf>>, 950 pages.
Nakahachi, et al., "Discrepancy of performance among working memory-related tasks in autism spectrum disorders was caused by task characteristics, apart from working memory, which could interfere with task execution," Psychiatry and Clinical Neurosciences, vol. 60, No. 3, Jun. 2006, pp. 312-318.
Nakahachi, et al., "Disturbed holistic processing in autism spectrum disorders verified by two cognitive tasks requiring perception of complex visual stimuli," Psychiatry Research, vol. 159, No. 3, Jun. 2008, pp. 330-338.
Nebel, et al., "Disruption of functional organization within the primary motor cortex in children with autism," Human Brain Mapping, vol. 35, No. 2, Feb. 2014, pp. 567-580.
Nigg, "Neuropsychologic Theory and Findings in Attention-Deficit/Hyperactivity Disorder: The State of the Field and Salient Challenges for the Coming Decade," Biological Psychiatry, vol. 57, No. 11, Jun. 2005, pp. 1424-1435.
Nigg, "On inhibition/disinhibition in developmental psychopathology: Views from cognitive and personality psychology and a working inhibition taxonomy," Psychological Bulletin, vol. 126, No. 2, Mar. 2000, pp. 220-246.
Nigg, et al., "Neuropsychological Executive Functions and DSM-IV ADHD Subtypes," Journal of the American Academy of Child & Adolescent Psychiatry, vol. 41, No. 1, Jan. 2002, pp. 59-66.
Nijmeijer, et al., "Attention-deficit/hyperactivity disorder and social dysfunctioning," Clinical Psychology Review, vol. 28, No. 4, Apr. 2008, pp. 692-708 (28 pages).
Nordahl, et al., "Cortical Folding Abnormalities in Autism Revealed by Surface-Based Morphometry," Journal of Neuroscience, vol. 27, No. 43, Oct. 2007, pp. 11725-11735.
Ozonoff and Strayer, et al., "Further Evidence of Intact Working Memory in Autism," Journal of Autism and Developmental Disorders, vol. 31, No. 3, Jun. 2001, pp. 257-263.
Parade, et al., "The reliability and validity of the Infant Behavior Questionnaire-Revised," Infant Behavior and Development, vol. 31, No. 4, Dec. 2008, pp. 637-646 (18 pgs).
Partridge and Lerner, "A latent growth-curve approach to difficult temperament," Infant and Child Development, vol. 16, No. 3, Jun. 2007, pp. 255-265.

(56) References Cited

OTHER PUBLICATIONS

Pascualvaca, et al., "Attentional Capacities in Children with Autism: Is There a General Deficit in Shifting Focus?," Journal of Autism and Developmental Disorders, vol. 28, No. 6, Dec. 1998, pp. 467-478.
Pennington and Ozonoff, "Executive Functions and Developmental Psychopathology," Journal of Child Psychology and Psychiatry, vol. 37, No. 1, Jan. 1996, pp. 51-87.
Pennington, et al., "Dimensions of executive functions in normal and abnormal development," Evolution, Neurobiology, and Behavior, 1997, pp. 265-281 (abstract).
Ping, et al., "Prenatal maternal stress predicts stress reactivity at 2.5 years of age: The Iowa Flood Study," Psychoneuroendocrinology, vol. 56, Jun. 2015, pp. 62-78.
Power, et al., "Functional Network Organization of the Human Brain," Neuron, vol. 72, No. 4, Nov. 2011, pp. 365-678.
Power, et al., "Methods to detect, characterize, and remove motion artifact in resting state fMRI," Neuroimage, vol. 84, Jan. 2014, pp. 320-341.
Prater, et al., "Aberrant Amygdala-Frontal Cortex Connectivity During Perception of Fearful Faces and at Rest in Generalized Social Anxiety Disorder," Depression and Anxiety, vol. 30, No. 3, Mar. 2013, pp. 234-241.
Pruett, et al., "Impaired eye region search accuracy in children with autistic spectrum disorders," PLOS One, vol. 8, No. 3, Mar. 2013, 13 pages.
Putnam, et al., "Development and Assessment of Short and Very Short Forms of the Infant Behavior Questionnaire-Revised," Journal of Personality Assessment, vol. 96, No. 4, Jul. 4, 2014, pp. 445-458.
Putnam, et al., "Measurement of fine-grained aspects of toddler temperament: The Early Childhood Behavior Questionnaire," Infant Behavior and Development, vol. 29, No. 3, Jul. 2006, pp. 386-401.
Qiu, et al., "Canonical TGF-BETA signaling regulates the relationship between prenatal maternal depression and amygdala development in early life," Translational Psychiatry, vol. 11, No. 170, Mar. 2012, 10 pages.
Qiu, et al., "Effects of Antenatal Maternal Depressive Symptoms and Socio-Economic Status on Neonatal Brain Development are Modulated by Genetic Risk," Cerebral Cortex, vol. 27, No. 5, May 2017, pp. 3080-3092.
Qiu, et al., "Maternal anxiety and infants' hippocampal development: timing matters," Translational Psychiatry, vol. 3, Sep. 2013, 7 pages.
Radloff, "The CES-D Scale: A Self-Report Depression Scale for Research in the General Population," Applied Psychological Measurement, vol. 1, No. 3, Jun. 1977, pp. 385-701.
Ramsay, et al., "Spline smoothing over difficult regions," Journal of the Royal Statistical Society: Series B (Statistical Methodology), vol. 64, No. 2, May 2002, pp. 307-319 (abstract).
Ray, et al., "Structural and Functional Connectivity of theHuman Brain in Autism Spectrum Disorders andAttention-Deficit/Hyperactivity Disorder: A RichClub-Organization Study," Human Brain Mapping, vol. 35, No. 12, Dec. 2014, pp. 6032-6048.
Redcay, et al., "Intrinsic functional network organization in high-functioning adolescents with autism spectrum disorder," Frontiers in Human Neuroscience, vol. 7, Sep. 2013, 11 pages.
Reiersen and Todd, "Co-occurrence of ADHD and autism spectrum disorders: phenomenology and treatment," Expert Review of Neurotherapeutics, vol. 8, No. 4, Apr. 2008, pp. 657-669.
Rice and Barone, "Critical periods of vulnerability for the developing nervous system: evidence from humans and animal models," Environmental Health Perspectives, vol. 108, No. 3, Jun. 2000, pp. 511-533.
Rifkin-Graboi, et al., "Antenatal Maternal Anxiety Predicts Variations in Neural Structures Implicated in Anxiety Disorders in Newborns," Journal of the American Academy of Child & Adolescent Psychiatry, vol. 54, No. 4, Apr. 2015, pp. 313-321.e2.
Rifkin-Graboi, et al., "Prenatal Maternal Depression Associates with Microstructure of Right Amygdala in Neonates at Birth," Biological Psychiatry, vol. 74, No. 11, Dec. 2013, pp. 837-844.
Robbins, et al., "Cambridge Neuropsychological Test Automated Battery (CANTAB): A Factor Analytic Study of a Large Sample of Normal Elderly Volunteers," Dementia, vol. 5, No. 5, Sep.-Oct. 1994, pp. 266-281.
Rogers, et al., "Neonatal Amygdala Functional Connectivity at Rest in Healthy and Preterm Infants and Early Internalizing Symptoms," Journal of the American Academy of Child & Adolescent Psychiatry, vol. 56, No. 2, Feb. 2017, pp. 157-166.
Rommelse, et al., "Cognitive Profiling Useful for Unraveling Cross-Disorder Mechanisms: Support for a Step-Function Endophenotype Model," Clinical Psychological Science, vol. 4, No. 6, Sep. 2016, pp. 957-970 (abstract).
Rommelse, et al., "Structural brain imaging correlates of ASD and ADHD across the lifespan: a hypothesis-generating review on developmental ASD-ADHD subtypes," Journal of Neural Transmission, vol. 124, No. 2, Feb. 2017, pp. 259-271.
Rosvall and Bergstorm, "Maps of random walks on complex networks reveal community structure," PNAS USA, vol. 105, No. 4, Jan. 2008, pp. 1118-1123.
Roy, et al., "Intrinsic Functional Connectivity of Amygdala-Based Networks in Adolescent Generalized Anxiety Disorder," Journal of the American Academy of Child & Adolescent Psychiatry, vol. 52, No. 3, Mar. 2013, pp. 290-299.e2 (17 pgs).
Rudolph, et al., "Maternal IL-6 during pregnancy can be estimated from newborn brain connectivity and predicts future working memory in offspring," Nature Neuroscience, vol. 21, No. 5, May 2018, pp. 765-772 (25 pgs).
Russell, et al., "Working Memory in Children with Autism and with Moderate Learning Difficulties," Journal of Child Psychology and Psychiatry, vol. 37, No. 6, Sep. 1996, pp. 673-686.
Sabuncu, et al., "Clinical Prediction from Structural Brain MRI Scans: A Large-Scale Empirical Study," Neuroinformatics, vol. 13, Jan. 2015, pp. 31-46.
Sandman, et al., "Exposure to Prenatal Psychobiological Stress Exerts Programming Influences on the Mother and Her Fetus," Neuroendocrinology, vol. 95, No. 1, Feb. 2012, pp. 8-21.
Seeley, et al., "Dissociable Intrinsic Connectivity Networks for Salience Processing and Executive Control," Journal of Neuroscience, vol. 27, No. 9, Feb. 2007, pp. 2349-2356.
Semrud-Clikeman, et al., "Comparison Among Children with Children with Autism Spectrum Disorder, Nonverbal Learning Disorder and Typically Developing Children on Measures of Executive Functioning," Journal of Autism and Developmental Disorders, vol. 44, No. 2, Feb. 2014, pp. 331-342.
Semrud-Clikeman, et al., "Executive Functioning in Children with Asperger Syndrome, ADHD-Combined Type, ADHD-Predominately Inattentive Type, and Controls," Journal of Autism and Developmental Disorders, vol. 40, Aug. 2010, pp. 1017-1027.
Senderecka, et al., "Event-related potentials in children with attention deficit hyperactivity disorder: An investigation using an auditory oddball task," International Journal of Psychophysiology, vol. 85, No. 1, Jul. 2012, pp. 106-115.
Shiels and Hawk, et al., "Self-Regulation in ADHD: The Role of Error Processing," Clinical Psychology Review, vol. 30, No. 8, Dec. 2010, pp. 951-961 (24 pgs).
Shokouhi, et al., "Changes in the Sulcal Size Associated With Autism Spectrum Disorder Revealed by Sulcal Morphometry," Autism Research, vol. 5, No. 4, Aug. 2012, pp. 245-252.
Silverstein, et al., "The Relationship Between Executive Function Deficits and DSM-5-Defined ADHD Symptoms," Journal of Attention Disorders, vol. 24, No. 1, Oct. 2018, pp. 41-51.
Sinzig, et al., "Inhibition, flexibility, working memory and planning in autism spectrum disorders with and without comorbid ADHD-symptoms," Child and Adolescent Psychiatry and Mental Health, vol. 2, No. 4, Jan. 2008, 12 pages.
Sonuga-Barke, et al., "Beyond the Dual Pathway Model: Evidence for the Dissociation of Timing, Inhibitory, and Delay-Related Impairments in Attention-Deficit/Hyperactivity Disorder," Journal of the American Academy of Child & Adolescent Psychiatry, vol. 49, No. 4, Apr. 2010, 32 pages.

(56) References Cited

OTHER PUBLICATIONS

Spek, et al., "Verbal fluency in adults with high functioning autism or Asperger syndrome," Neuropsychologia, vol. 47, No. 3, Feb. 2009, pp. 652-656.

Spielberger, et al., "STAI Manual for the State-Trait Anxiety Inventory," Consulting Psychologists Press, Palo Alto, California, United States of America, 1970, 25 pages.

Stevens, et al., "The comorbidity of ADHD in children diagnosed with autism spectrum disorder," Research in Autism Spectrum Disorders, vol. 31, Nov. 2016, pp. 11-18.

Stevenson, et al., "Brief Report: Arrested Development of Audiovisual Speech Perception in Autism Spectrum Disorders," Journal of Autism and Developmental Disorders, vol. 44, No. 6, Jun. 2014, pp. 1470-1477 (15 pgs).

Stone and Gerrans, "What's domain-specific about theory of mind?," Social Neuroscience, vol. 1, No. 3-4, Sep. 2006, pp. 309-319.

Supekar, et al., "Brain hyperconnectivity in children with autism and its links to social deficits," Cell Reports, vol. 5, No. 3, Nov. 2013, pp. 738-747.

Szatmari, et al., "Developmental trajectories of symptom severity and adaptive functioning in an inception cohort of preschool children with autism spectrum disorder," JAMA Psychiatry, vol. 72, No. 3, Mar. 2015, pp. 276-283.

Tanaka, et al., "The perception and identification of facial emotions in individuals with Autism Spectrum Disorders using the Let's Face It! Emotion Skills Battery," Journal of Child Psychology and Psychiatry, vol. 53, No. 12, Dec. 2012, pp. 1259-1267.

Tau and Peterson, "Normal Development of Brain Circuits," Neuropsychopharmacology, vol. 35, No. 1, Jan. 2010, pp. 147-168.

Thomas, et al., "Newborn amygdala connectivity and early emerging fear," Developmental Cognitive Neuroscience, vol. 37, Jun. 2019, 12 pages.

Thomason, et al., "Age-related increases in long-range connectivity in fetal functional neural connectivity networks in utero," Developmental Cognitive Neuroscience, vol. 11, Feb. 2015, pp. 96-104.

Thorell, "Do delay aversion and executive function deficits make distinct contributions to the functional impact of ADHD symptoms? A study of early academic skill deficits," Journal of Child Psychology and Psychiatry, vol. 48, No. 11, Nov. 2007, pp. 1061-1070.

Tottenham, et al., "Elevated amygdala response to faces following early deprivation," Developmental Science, vol. 14, No. 2, Mar. 2011, pp. 190-204.

Tottenham, et al., "The NimStim set of facial expressions: judgments from untrained research participants," Psychiatry Research, vol. 168, No. 3, Aug. 2009, pp. 242-249.

Tyszka, et al., "Largely Typical Patterns of Resting-State Functional Connectivity in High-Functioning Adults with Autism," Cerebral Cortex, vol. Jul. 2014, pp. 1894-1905.

Uluyagmur-Ozturk, et al., "ADHD and ASD Classification Based on Emotion Recognition Data," 2016 15th IEEE International Conference on Machine Learning and Applications (ICMLA), Dec. 2016, 1 page.

Valk, et al., "Multicenter Mapping of Structural NetworkAlterations in Autism," Human Brain Mapping, vol. 36, No. 6, Jun. 2015, pp. 2364-2373.

Van der Meer, et al., "Homogeneous Combinations of ASD-ADHD Traits and Their Cognitive and Behavioral Correlates in a Population-Based Sample," Journal of Attention Disorders, vol. 21, No. 9, Jul. 2017, pp. 753-763.

Vandenbroucke, et al., "A neural substrate for atypical low-level visual processing in autism spectrum disorder," Brain, vol. 131, No. 4, Apr. 2008, pp. 1013-1024.

Vann, et al., "What does the retrosplenial cortex do?," Nature Reviews Neuroscience, vol. 10, No. 11, Nov. 2009, pp. 792-802.

Vasung, et al., "Development of axonal pathways in the human fetal fronto-limbic brain: histochemical characterization and diffusion tensor imaging," Journal of Anatomy, vol. 217, No. 4, Oct. 2010, pp. 400-417.

Vasung, et al., "Exploring early human brain development with structural and physiological neuroimaging," NeuroImage, vol. 187, Feb. 2019, pp. 226-254 (74 pgs).

Verte, et al., "Executive Functioning in Children with an Autism Spectrum Disorder: Can We Differentiate Within the Spectrum?," Journal of Autism and Developmental Disorders, vol. 36, No. 3, Apr. 2006, pp. 351-372.

Volkmar, et al., "Moving beyond a categorical diagnosis of autism," Lancet Neurology, vol. 15, No. 3, Mar. 2016, pp. 237-238.

Volkow, et al., "Motivation deficit in ADHD is associated with dysfunction of the dopamine reward pathway," Molecular Psychiatry, vol. 16, Nov. 2011, pp. 1147-1154.

Wallace, et al., "Longitudinal Cortical Development During Adolescence and Young Adulthood in Autism Spectrum Disorder: Increased Cortical Thinning but Comparable Surface Area Changes," Journal of the American Academy of Child & Adolescent Psychiatry, vol. 54, No. 6, Jun. 2015, pp. 464-469 (13 pgs).

Wang, et al., "Multi-atlas segmentation of subcortical brain structures via the AutoSeg software pipeline," Frontiers in Neuroinformatics, vol. 8, No. 7, Feb. 2014, 11 pages.

Welsh and Pennington, "Assessing frontal lobe functioning in children: Views from developmental psychology," Developmental Neuropsychology, vol. 4, No. 3, Jan. 1988, pp. 199-230.

Willcutt, et al., "Validity of DSM-IV attention deficit/hyperactivity disorder symptom dimensions and subtypes.," Journal of Abnormal Psychology, vol. 121, No. 4, Nov. 2012, pp. 991-1010.

Willcutt, et al., "Validity of the Executive Function Theory of Attention-Deficit/Hyperactivity Disorder: A Meta-Analytic Review," Biological Psychiatry, vol. 57, No. 11, Jun. 2005, pp. 1336-1346.

Wilson, et al., "Delay discounting of reward in ADHD: application in young children," Journal of Child Psychology and Psychiatry, vol. 52, No. 3, Mar. 2011, pp. 256-264.

Yasuda, et al., "Cognitive inflexibility in Japanese adolescents and adults with autism spectrum disorders," World Journal of Psychiatry, vol. 4, No. 2, Jun. 2014, pp. 42-48.

Yushkevich, et al., "User-guided 3D active contour segmentation of anatomical structures: significantly improved efficiency and reliability," Neuroimage, vol. 31, No. 3, Jul. 2006, pp. 1116-1128 (49 pgs).

Zhang, et al., "Large-scale functional neural network correlates of response inhibition: an fMRI meta-analysis," Brain Structure and Function, vol. 222, No. 9, Dec. 2019, pp. 3973-3990.

Zhang, et al., "Prognostic Significance of Tumor-Associated Macrophages in Solid Tumor: A Meta-Analysis of the Literature," PLOS ONE, vol. 7, No. 12, Dec. 2012, 14 pages.

Holmes, et al., "The Diagnostic Utility of Executive Function Assessments in the Identification of ADHD in Children," Child and Adolescent Mental Health, vol. 15, No. 1, Jan. 2010, pp. 37-43.

Huang-Pollock, et al., "Evaluating vigilance deficits in ADHD: A meta-analysis of CPT performance," Journal of Abnormal Psychology, vol. 121, No. 2, May 2012, pp. 360-371 (22 pgs).

Hughes, et al., "A review of recent reports on autism: 1000 studies published in 2007," Epilepsy and Behavior, vol. 13, No. 3, Oct. 2008, pp. 425-437.

Hurks, et al., "Verbal fluency over time as a measure of automatic and controlled processing in children with ADHD," Brain and Cognition, vol. 55, No. 3, Aug. 2004, pp. 535-544.

Insel, et al., "The NIMH Research Domain Criteria (RDoC) Project: precision medicine for psychiatry," American Journal of Psychiatry, vol. 171, No. 4, Apr. 2014, pp. 395-397.

Insel, et al.,"Research Domain Criteria (RDoC): Toward a New Classification Framework for Research on Mental Disorders," American Journal Psychiatry, vol. 167, No. 7, Jul. 2010, pp. 748-751.

Jamal, et al., "Classification of autism spectrum disorder using supervised learning of brain connectivity measures extracted from synchrostates," Journal of Neural Engineering, vol. 11, No. 4, Jul. 2014, 27 pages.

James, et al., "Principal component models for sparse functional data ," Biometrika, vol. 87, No. 3, Sep. 2000, pp. 587-602.

Johnson and Bickel, "An algorithm for identifying nonsystematic delay-discounting data," Clinical Psychopharmacology, vol. 16, No. 3, Jun. 2008, pp. 264-274 (19 pgs).

(56) References Cited

OTHER PUBLICATIONS

Joseph, et al., "Executive dysfunction and its relation to language ability in verbal school-age children with autism," Developmental Neuropsychology, vol. 27, No. 3, Sep. 2005, pp. 361-378.
Joseph, et al., "Self-ordered pointing in children with autism: failure to use verbal mediation in the service of working memory?" Neuropsychologia, vol. 43, No. 10, Feb. 2005, pp. 1400-1411.
Joshi, et al., "Symptom Profile of ADHD in Youth With High-Functioning Autism Spectrum Disorder: A Comparative Study in Psychiatrically Referred Populations," Journal of Attention Disorders, vol. 21, No. 10, Aug. 2017, pp. 346-855.
Karalunas, et al., "Decomposing attention-deficit/hyperactivity disorder (ADHD)-related effects in response speed and Variability," Neuropsychology, vol. 26, No. 6, Nov. 2012, pp. 684-694.
Karalunas, et al., "Overlapping and Distinct Cognitive Impairments in Attention-Deficit/Hyperactivity and Autism Spectrum Disorder without Intellectual Disability," Journal of Abnormal Child Psychology, vol. 46, No. 8, Nov. 2018, pp. 1705-1716.
Karalunas, et al., "Subtyping Attention-Deficit/Hyperactivity Disorder Using Temperament Dimensions Toward Biologically Based Nosologic Criteria," JAMA Psychiatry, vol. 71, No. 9, Sep. 2014, pp. 1015-1024.
Kasper, et al., "Moderators of working memory deficits in children with attention-deficit/hyperactivity disorder (ADHD): A meta-analytic review," Clinical Psychology Review, vol. 32, No. 7, Nov. 2012, pp. 605-617.
Katuwal, et al., "Divide and Conquer: Sub-Grouping of ASD Improves ASD Detection Based on Brain Morphometry," PLOS One, vol. 11, No. 4, Apr. 2016, 24 pages.
Katuwal, et al., "The predictive power of structural MRI in Autism diagnosis," Annual International Conference of the IEEE Engineering in Medicine and Biology Society, Aug. 2015, pp. 4270-4273.
Kaufman, et al., "Schedule for Affective Disorders and Schizophrenia for School-Age Children-Present and Lifetime Version (K-SADS-PL): initial reliability and validity data," Journal of the American Academy of Child & Adolescent Psychiatry, vol. 36, No. 7, Jul. 1997, pp. 980-988.
Kim, et al., "Anxiety Dissociates Dorsal and Ventral Medial Prefrontal Cortex Functional Connectivity with the Amygdala at Rest," Cerebral Cortex, vol. 21, No. 7, Jul. 2011, pp. 1667-1673.
Kofler, et al., "ADHD and Working Memory: The Impact of Central Executive Deficits and Exceeding Storage/Rehearsal Capacity on Observed Inattentive Behavior," Journal of the American Academy of Child & Adolescent Psychiatry, vol. 38, Feb. 2010, pp. 149-161.
Kohavi, et al., "A Study of Cross-Validation and Bootstrap for Accuracy Estimation and Model Selection," International Joint Conference on Artificial Intelligence (IJCAI), vol. 2, Aug. 1995, pp. 1137-1143.
Lange, et al., "Longitudinal Volumetric Brain Changes in Autism Spectrum Disorder Ages 6-35 Years," Autism Research, vol. 8, No. 1, Feb. 2015, pp. 82-93 (22 pgs).
Lecei, et al., "Can we use neuroimaging data to differentiate between subgroups of children with ADHD symptoms: A proof of concept study using latent class analysis of brain activity," NeuroImages: Clinical, vol. 21, Nov. 2018, 7 pages.
Leitner, et al., "The co-occurrence of autism and attention deficit hyperactivity disorder in children—what do we know?," Frontiers in Human Neuroscience, vol. 8, Apr. 2014, 8 pages.
Leno, et al., "Testing the specificity of executive functioning impairments in adolescents with ADHD, ODD/CD and ASD," European Child & Adolescent Psychiatry, vol. 27, Jul. 2018, pp. 899-908.
Lin, et al., "Altered Resting-State Frontoparietal Control Network in Children with Attention-Deficit/Hyperactivity Disorder," Journal of the International Neuropsychological Society, vol. 21, No. 4, Apr. 2015, 14 pages.
Liu, et al., "Identifying children with autism spectrum disorder based on their face processing abnormality: A machine learning framework," Autism Research, vol. 9, No. 8, Aug. 2016, pp. 888-898.
Lombardo, et al., "Large-scale associations between the leukocyte transcriptome and BOLD responses to speech differ in autism early language outcome subtypes," BioRxiv, vol. 21, Dec. 2018, pp. 1680-1688 (27 pgs).
Lundervold, et al., "Attention Deficits in Children With Combined Autism and ADHD: A CPT Study," Journal of Attention Disorders, vol. 20, Jul. 2016, pp. 599-609.
Macizo, et al., "Phonological and Visuospatial Working Memory in Autism Spectrum Disorders" Journal of Autism and Developmental Disorders, vol. 46, No. 2956-2967.
MacKay, et al., "The problems of flexibility, fluency, and speed-accuracy trade-off in skilled behavior.," Psychological Review, vol. 89, No. 5, Sep. 1982, pp. 483-506.
Mahone, et al., "Validity of the behavior rating inventory of executive function in children with ADHD and/or Tourette syndrome," Archives of Clinical Neuropsychology, vol. 17, No. 7, Oct. 2002, pp. 643-662.
Martel, et al., "Executive Function in Adolescents With ADHD," Journal of the American Academy of Child & Adolescent Psychiatry, vol. 46, No. 11, Nov. 2007, pp. 1437-1444 (abstract).
Martel, et al., "How Do Trait Dimensions Map onto ADHD Symptom Domains?," Journal of Abnormal Child Psychology, vol. 37, Apr. 2009, pp. 337-348 (20 pgs).
Martel, et al., "Research Review: A new perspective on attention-deficit/hyperactivity disorder: emotion dysregulation and trait models," Journal of Child Psychology and Psychiatry, vol. 50, No. 9, Sep. 2009, pp. 1042-1051.
Matson, et al., "Comorbidity and the Need for Interdisciplinary Treatments," Handbook of Interdisciplinary Treatments for Autism Spectrum Disorder, Springer International Publishing, Apr. 2019, pp. 29-47.
Matza, et al., "A review of the economic burden of ADHD," Cost Effectiveness and Resource Allocation, vol. 3, Jun. 2005, 9 pages.
McPheeters, et al., "A Systematic Review of Medical Treatments for Children With Autism Spectrum Disorders," Pediatrics, vol. 127, No. 5, May 2011, pp. 1312-1321.
Miller, et al., "Misunderstanding analysis of covariance," Journal of Abnormal Psychology, vol. 110, No. 1, 2001, pp. 10-48.
Miller, et al., "Sibling Recurrence Risk and Cross-aggregation of Attention-Deficit/Hyperactivity Disorder and Autism Spectrum Disorder," JAMA Pediatrics, vol. 173, No. 2, 2019, pp. 147-152.
Mills, et al., "ADHD and attentional control: Impaired segregation of task positive and task negative brain networks," Network Neuroscience, vol. 2, No. 2, Jun. 2018, pp. 200-217.
Miyake, et al., "The Unity and Diversity of Executive Functions and Their Contributions to Complex "Frontal Lob" Tasks: A Latent Variable Analysis," Cognitive Psychology, vol. 41, No. 1, Aug. 2000, pp. 49-100.
Molitor, et al., "Executive Function Deficits in Adolescents With ADHD: Untangling Possible Sources of Heterogeneity," Journal of Emotional and Behavioral Disorders, vol. 27, No. 3, Sep. 2019, pp. 165-177.
Monk, et al., "Abnormalities of intrinsic functional connectivity in autism spectrum disorders," NeuroImage, vol. 47, No. 2, Aug. 2009, pp. 764-772 (20 pgs).
Moog, et al., "Intergenerational Effect of Maternal Exposure to Childhood Maltreatment on Newborn Brain Anatomy," Biological Psychiatry, vol. 83, No. 2, Jan. 2018, pp. 120-127 (17 pgs).
Mora, et al., "Distinct Trajectories of Perinatal Depressive Symptomatology: Evidence From Growth Mixture Modeling," American Journal of Epidemiology, vol. 169, No. 1, Jan. 2009, pp. 24-32.
Morawetz, et al., "Effective amygdala-prefrontal connectivity predicts individual differences in successful emotion regulation," Social Cognitive and Affective Neuroscience, vol. 12, No. 4, Apr. 2017, pp. 569-585.
Morin, et al., "Atypical Face Perception in Autism: A Point of View?" Autism Research, vol. 8, No. 5, Oct. 2015, pp. 197-506.
Mulder, et al., "Basic Impairments in Regulating the Speed-Accuracy Tradeoff Predict Symptoms of Attention-Deficit/Hyperactivity Disorder," Biological Psychiatry, vol. 68, No. 12, Dec. 2010, pp. 1114-1119.

* cited by examiner

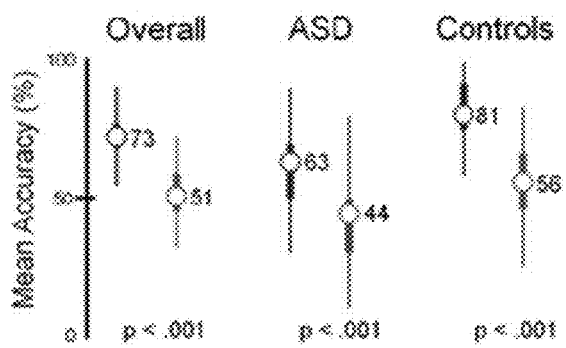
FIG. 14A
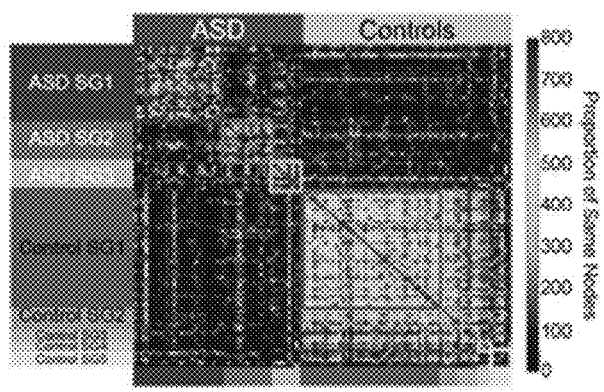
FIG. 14B
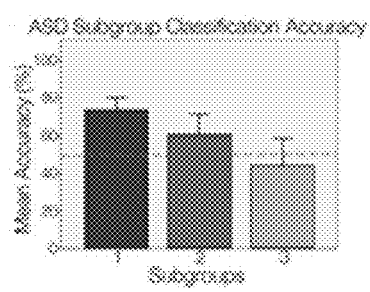 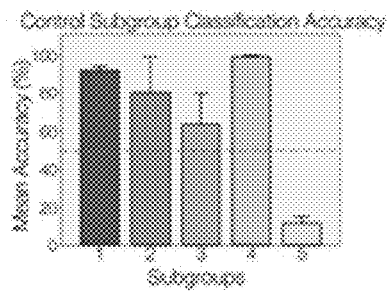 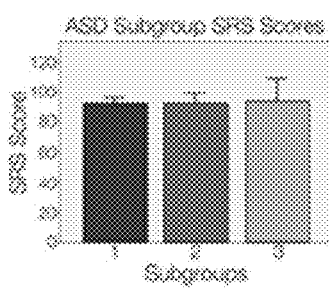
FIG. 14C    FIG. 14D    FIG. 14E

FIG. 18

Proportion of variance explained by age (blue) and gender (red)

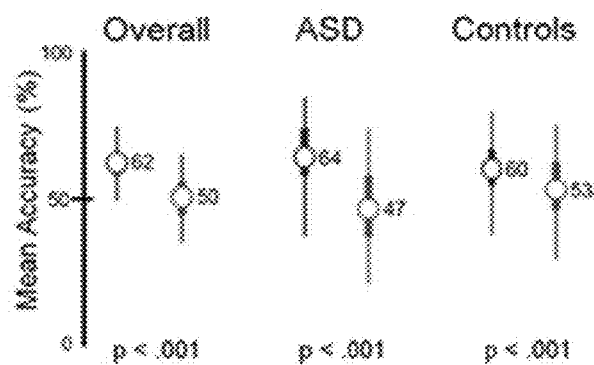
FIG. 20A
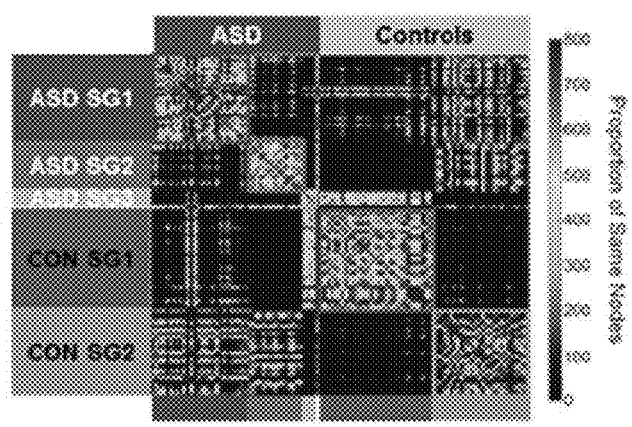
FIG. 20B
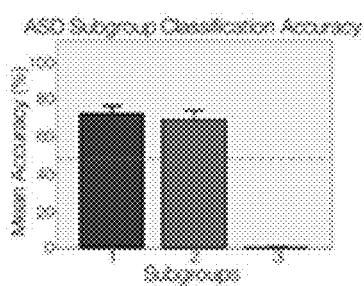 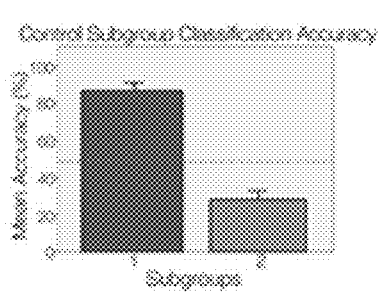 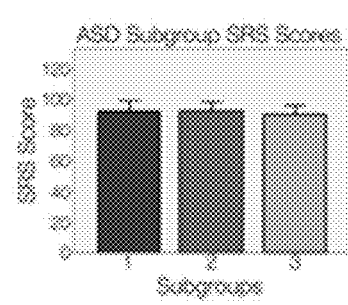
FIG. 20C    FIG. 20D    FIG. 20E

| Table S1 | PDS | | |
|---|---|---|---|
| Average for All Tests: TD = 58, ASD = 47 | | | |
| TD M (SD) | ASD M (SD) | T stat | p-value |
| 1.4 (0.83) | 2.1 (0.95) | 4.14 | <.001 |
| Facial&Affect Processing: TD = 44, ASD = 45 | | | |
| 1.6 (0.76) | 2.1 (1.00) | 2.77 | 0.007 |
| Delay Discounting: TD = 45, ASD = 40 | | | |
| 1.5 (0.79) | 2.3 (0.99) | 4.2 | <.001 |
| Stop Task: TD = 44, ASD = 40 | | | |
| 1.4 (0.85) | 2.1 (1.01) | 3.88 | <.001 |
| Spatial Span Task: TD = 46, ASD = 39 | | | |
| 1.4 (0.89) | 2.1 (1.01) | 3.59 | <.001 |
| CPT: TD = 44, ASD = 35 | | | |
| 1.4 (0.85) | 2.2 (1.01) | 4.16 | <.001 |

FIG. 27

| Participants (N = 130) | ASD (n = 64) | ADHD (n = 66) | Significance test |
|---|---|---|---|
| Female gender, n = 31 (23.8 %) | 13 (20.3) | 18 (27.3) | p = .413 |
| Age in years (7-16y), m = 11.5 (2.2) | 12.2 (2.3) | 10.9 (1.9) | t(128) = 3.67, p <.001 |
| Est. IQ (Block design), m = 11 (3.3) | 10.6 (3.2) | 11.3 (3.3) | t(128) = -1.22, p = .225 |

TABLE 4

| Useable scan data ASD+ADHD (n = 67) | ASD (n = 26) | ADHD (n = 41) | Significance test$^a$ | TD (N = 28) | Significance test$^b$ |
|---|---|---|---|---|---|
| Female gender, n = 15 (22.4%) | 4 (15.4) | 11 (26.8) | p = .37 | 4 (39.3) | p = .13 |
| Age (7-16y), m = 12.2 (2.3) | 13.6 (1.9) | 11.2 (2.0) | t(65) = 4.9, p <.001 | 11.4 (1.7) | t(66.3) = 1.8, p = .074 |
| Est. IQ (Block design) m = 10.8 (3.2) | 10.5 (3.0) | 11 (3.2) | t(65) = -.66, p = .502 | 12.4 (2.8) | t(93) = 4.9, p = .074 |

TABLE 5

FIG. 30

| Demographics | HSG-Mild (n = 79) | HSG-Severe (n = 51) | Significance test |
|---|---|---|---|
| ASD, n (%) | 40 (50.6) | 24 (47.1) | p = .72 |
| Female gender, n (%) | 15 (19) | 16 (31.4) | p = .14 |
| Age in years (7-16y) | 11.6 (2.1) | 11.4 (2.3) | t(128) = .663, p = .508 |
| Est. IQ (Block design) | 11.1 (3.4) | 11.3 (3.3) | t(128) = .553, p = .581 |

FIG. 34

| Response Inhibition | t-test | HSG-Severe | HSG-Mild |
|---|---|---|---|
| BRIEF: Inhibit | t(127,19) = 15.28, p<.001 | -4.55 | -1.43 |
| BRIEF: Emotional control | t(128) = -3.99, p<.001 | -2.84 | -1.65 |
| BRIEF: Monitor | t(127) = -4.20, p<.001 | -2.89 | -1.66 |
| Cognitive Flexibility | | | |
| BRIEF: Shift | t(128) = -2.96, p = .004 | -1.71 | -1.06 |
| BRIEF: Behavior regulation index | t(128) = -6.06, p<.001 | -4.07 | -1.92 |
| BRIEF: Metacognition | t(128) = -3.49, p<.001 | -3.71 | -1.93 |
| Working Memory | | | |
| BRIEF: Working memory | t(128) = -2.24, p = .027 | -2.85 | -2.39 |
| Spatial span, forward: Total Accuracy | t(124) = 2.04, p = .044 | -0.92 | -0.52 |
| Spatial span, backward: Total accuracy | t(125) = 2.35, p = .036 | -0.43 | 0.03 |
| Task Control | | | |
| BRIEF: Initiate | t(128) = -2.39, p = .018 | -1.42 | -1.06 |
| BRIEF: Plan and organize | t(128) = -2.86, p = .005 | -2.42 | -1.74 |
| BRIEF: Organization of materials | t(128) = -3.77, p = .006 | -1.27 | -0.79 |
| Stop task: Accuracy on Go-trials | t(127) = 3.23, p = .002 | -1.72 | -0.71 |

FIG. 36

| Demographics | ISG-Mild (n = 46) | ISG-Severe (n = 84) | Significance test |
|---|---|---|---|
| ASD, n (%) | 26(56.5) | 38(45.2) | P = .272 |
| Female gender, n (%) | 8(17.4) | 23(27.4) | P = .282 |
| Age in years (7-16y) | 11.6 (2.1) | 11.5(2.3) | t(128) = .189, p = .85 |
| Est. IQ (Block design) | 11.6 (3.2) | 10.6 (3.2) | t(128) = 1.58, p = .117 |

FIG. 37

| Response Inhibition | t-test | ISG-Severe | ISG-Mild |
|---|---|---|---|
| Colorword: Total errors | t(91.10) = -2.02, p = .046 | -1.50 | -0.82 |
| Colorword: Uncorrected errors | t(108.70) = -2.24, p = .02 | -0.87 | -0.13 |
| BRIEF: Inhibit | t(128) = -2.83, p = .005 | -3.00 | -2.01 |
| BRIEF: Emotional control | t(128) = -3.17, p = .002 | -2.47 | -1.48 |
| BRIEF: Monitor | t(74.76) = -6.74, p<.001 | -2.84 | -1.01 |
| Stop task: Mean reaction time | t(71.67) = 2.63, p = .01 | -0.23 | -0.89 |
| Cognitive Flexibility | | | |
| BRIEF: Shift | t(128) = -3.10, p = .002 | -1.56 | -0.87 |
| BRIEF: Behavior regulation index | t(128) = -3.84, p<.001 | -3.19 | 1.98 |
| BRIEF: Metacognition | t(128) = -14.41, p<.001 | -2.99 | -0.86 |
| Working Memory | | | |
| BRIEF: Working memory | t(128) = -11.18, p<.001 | -3.24 | -1.18 |
| Digit span: Backward | t(128) = -2.18, p = .031 | -0.76 | -0.39 |
| Task Control | | | |
| BRIEF: Initiate | t(128) = -10.84, p<.001 | -1.64 | -0.40 |
| BRIEF: Plan and organize | t(128) = -12.15, p<.001 | -2.74 | -0.67 |
| BRIEF: Organization of materials | t(128) = -9.70, p<.001 | -1.45 | -0.11 |
| Stop task: Accuracy on Go trials | t(123) = -3.35, p = .01 | -1.45 | -0.49 |

FIG. 38

SUBTYPING HETEROGENEOUS DISORDERS USING FUNCTIONAL RANDOM FOREST MODELS

CROSS-REFERENCE TO RELATED APPLICATIONS

This application claims priority to, and the benefit of, U.S. Provisional Patent Application No. 62/783,023, filed Dec. 20, 2018 and entitled "SUBTYPING HETEROGENEOUS DISORDERS USING FUNCTIONAL RANDOM FOREST MODELS," which is incorporated herein by reference in its entirety.

STATEMENT REGARDING FEDERALLY SPONSORED RESEARCH OR DEVELOPMENT

This invention was made with government support under T15 LM007088 and R01 MH096773 awarded by the National Institutes of Health. The government has certain rights in the invention.

BACKGROUND OF THE DISCLOSURE

Precision medicine proposes to customize medical decisions, diagnostic techniques, and therapeutic treatments tailored to individual patients. However, due to the significant complexity inherent in many disease profiles, it is difficult for clinicians to specifically customize care for individual patients. In some cases, the specificity required to customize precision medicine therapies for patients require results from invasive, time-consuming, and/or expensive diagnostic tests with limited availability.

For certain medical conditions, such as heterogeneous conditions, it may be difficult to identify patients by features that have clinical relevance. As a result, diagnosing and treating patients can be challenging.

SUMMARY OF THE DISCLOSURE

The current disclosure provides various systems, methods, and devices that generate predictive models for subtyping heterogeneous disorders using functional Random Forest (RF) models.

The current disclosure also provides various systems, methods, and devices for generating recommendations related to heterogeneous disorders using predictive models.

An example method includes receiving training data indicating first behavioral features of a sample population and biomarkers associated with Autism Spectrum Disorder (ASD) diagnoses of the sample population, the sample population comprising at least one individual; generating at least 1000 decision trees in a Random Forest (RF) based on the training data, each one of the decision trees being configured to divide the individuals of the sample population into multiple categories of the ASD diagnoses based on the behavioral features; in response to generating the decision trees, generating a proximity matrix comprising multiple entries using the RF, the entries indicating proportions of the decision trees that categorize pairs of the individuals into the same categories among the multiple categories; identifying subgroups of the ASD diagnoses by detecting communities of the proximity matrix; receiving patient data indicating second behavioral features of a particular individual outside of the sample population; determining, based on the second behavioral features and the RF, that the particular individual is part of a particular subgroup among the subgroups; predicting, based on the particular subgroup, a treatment that will improve a prognosis of the particular individual with respect to ASD; and outputting, on a clinical device, an indication of the treatment.

In some implementations, the first behavioral features comprise observed behaviors of the individuals in the sample population, wherein the second behavioral features comprise the observed behaviors of the particular individual, and wherein the behaviors comprise: a behavior related to working memory of each of the individuals; a behavior related to response inhibition of each of the individuals; a behavior related to temporal reward discounting by each of the individuals; a behavior related to attentional vigilance of each of the individuals; a behavior related to processing of a facial feature by each of the individuals; a behavior related to processing of a vocal affect by each of the individuals; and a behavior related to processing of facial emotion by each of the individuals.

In some implementations, the biomarkers comprise at least one of structural Magnetic Resonance Imaging (MRI) images of brains of the individuals, functional MRI (fMRI) images of the brains of the individuals, or genotypes of the individuals.

In various implementations, an example method includes identifying training data indicating features of a sample population and clinical outcomes of the sample population, the clinical outcomes being associated with a heterogeneous condition; generating decision trees in a Random Forest (RF) based on the training data, each one of the decision trees being configured to divide the sample population into multiple categories based on the features of the sample population; in response to generating the decision trees, generating a proximity matrix comprising multiple entries using the RF, one of the entries indicating a proportion of the decision trees that categorize a first individual among the sample population and a second individual among the sample population into the same categories among the multiple categories; and identifying subgroups of the heterogeneous condition by detecting communities of the proximity matrix.

In some cases, the heterogeneous condition comprises at least one of Autism Spectrum Disorder (ASD), ADHD, or infant neurodevelopment. In some cases, the features comprise behavioral features of the sample population. In some cases, the behavioral features of the sample population comprise observed behaviors of the sample population, the observed behaviors comprising at least one of: a first behavior related to working memory of at least one third individual among the sample population; a second behavior related to response inhibition of the at least one third individual; a third behavior related to temporal reward discounting by the at least one third individual; a fourth behavior related to attentional vigilance of the at least one third individual; a fifth behavior related to processing of a facial feature by the at least one third individual; a sixth behavior related to processing of a vocal affect by the at least one third individual; or a seventh behavior related to processing of facial emotion by the at least one third individual.

In some cases, the features comprise perinatal stress of mothers of the sample population. In some cases, the RF comprises at least 1000 decision trees. In some cases, detecting the communities comprises applying infomap to the proximity matrix.

In some cases, the features are features, and the example method further includes identifying second features of a third individual outside of the sample population; and determining, based on the second features, that the third individual is part of a particular subgroup among the subgroups.

In some cases, the example method further includes predicting, based on the particular subgroup, a treatment that will improve a prognosis of the third individual with respect to the heterogeneous condition; and outputting, on a clinical device, an indication of the treatment. In some cases, the method include outputting, on a clinical device, an indication of the particular subgroup.

Various example systems may include at least one processor and memory storing instructions that, when executed by the at least one processor, cause the at least one processor to perform operations comprising any of the example methods described herein. In some cases, an example system can include a clinical device configured to output information related to an identified subtype.

BRIEF DESCRIPTION OF THE FIGURES

The detailed description is described with reference to the accompanying figures. The patent or application file contains at least one drawing executed in color. Copies of this patent or patent application publication with color drawing(s) will be provided by the Office upon request and payment of the necessary fee.

FIGS. 11A-18 illustrate various tables and figures related to Example 1 according to various implementations of the present disclosure.

FIGS. 19-27 illustrate various tables and figures related to Example 2 according to various implementations of the present disclosure.

FIG. 19 illustrates an example radar plot of proportion of variance explained for age (red) and gender (blue). Orientation matches other radar plots in FIG. 15 and FIG. 21.

FIGS. 20A to 20E relates to Example 2. FIG. 20A shows a plot of accuracy for observed (blue) vs. permuted (red) RF models after controlling for age and gender. Wide bars refer to the 25th/75th percentiles and thinner bars refer to the 2.5th/97.5th percentiles. FIG. 20B shows a sorted proximity matrix, where each row and column represents a participant and each cell represents the number of times two participants ended in the same terminal node across all the RF models. FIG. 20C shows a plot of RF classification accuracy for autism spectrum disorder (ASD) subgroups, error bars represent 1 standard error of the mean (SE). Dashed blue line represents 50% mean accuracy. FIG. 20D shows a plot of RF classification accuracy for typically developing (TD) subgroups. Error bars represent 1 SE. Dashed blue line represents 50% mean accuracy. FIG. 20E shows a plot of simple random sample (SRS) for ASD subgroups. The color code for each subgroup can be maintained throughout all subfigures.

FIG. 21 illustrates radar plots representing the 50th percentile for performance per group. All data are normalized within each radar plot from 0 to 100 percent. The colors for each subgroup are the same as in FIGS. 20A to 20E.

FIG. 22A illustrates Autism Diagnostic Observation Schedule (ADOS) Second Edition summed scaled scores for original subgroups. FIG. 22B illustrates ADOS summed scaled scores for supplemental subgroups.

FIG. 23A illustrates age for original ASD subgroups. FIG. 23B illustrates age for original TD subgroups FIG. 23C illustrates age for supplemental ASD subgroups. FIG. 23D illustrates age for supplemental control subgroups.

FIGS. 14A to 14E). FIG. 24A illustrates age for original ASD subgroups. FIG. 24B illustrates age for original TD subgroups FIG. 24C illustrates age for supplemental ASD subgroups. FIG. 24D illustrates age for supplemental TD subgroups. Abbreviations: WISC: Wechsler Intellectual Scale for Children; BD: Block Design.

FIGS. 14A to 14E). FIG. 25A illustrates age for original subgroups. FIG. 25B illustrates age for supplemental subgroups. FIG. 25C illustrates IQ for original subgroups. FIG. 25D illustrates IQ for supplemental subgroups. Abbreviations: WISC: Wechsler Intellectual Scale for Children; BD: Block Design.

FIG. 26 illustrates a plot of variable importance for each feature included in the analysis. The variables are ordered by task, from left to right, in the same order as the radar plots. Positive values indicate that removing the feature from the model increases error (e.g., reduces performance), and therefore are more important variables for the RF model.

FIG. 27 illustrates a pubertal developmental stage (PDS) table for ASD and TD samples per test. Because PDS was acquired once per participant, PDS was not tested for visits that occurred greater than six months after PDS was acquired.

FIG. 28A illustrates plots of classification accuracy and confidence intervals for observed (blue) and permuted (red) models. FIG. 28B illustrates RF similarity matrix derived from the model for positive (purple) and negative (gold). Subgroups (boxes) were identified via Infomap.

FIG. 30 illustrates tables reporting demographics of participants in Example 5.

FIG. 34 illustrates Table 6, which provides demographics for identified Hyperactive subgroups and significance tests comparing HSG-Mild and HSG-Severe.

FIG. 36 illustrates Table 7, which provides variables included in the Hyperactive model that measurably differed between identified subgroups.

FIG. 37 illustrates Table 8, which provides demographics for identified Inattentive subgroups and significance tests comparing ISG-Mild and ISG-Severe.

FIG. 38 illustrates Table 9, which provides variables included in the Inattentive model that observably differed between identified subgroups.

DETAILED DESCRIPTION

Figure 1:
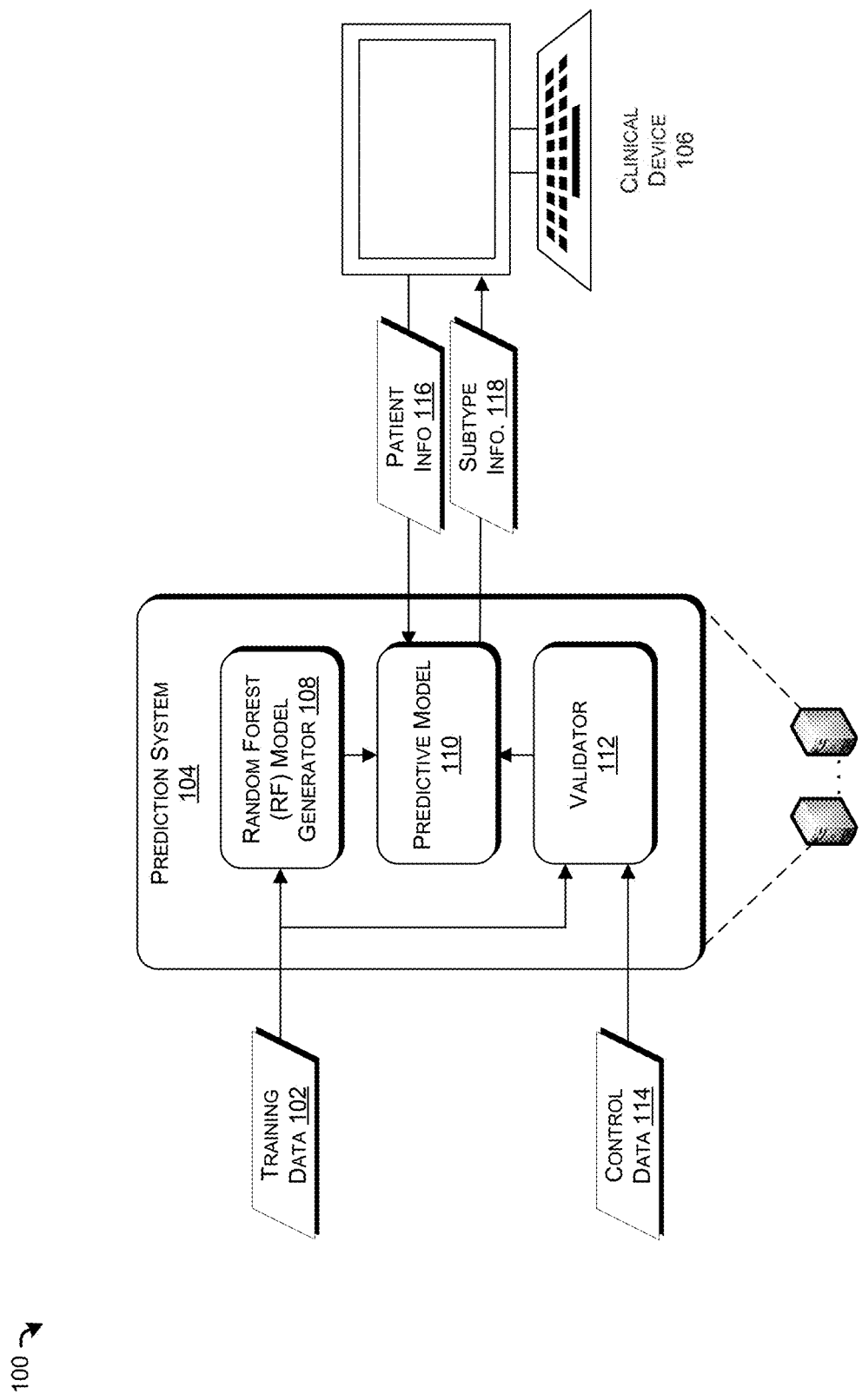
FIG. 1 illustrates a network configuration according to various implementations of the present disclosure.

The current disclosure provides various systems, methods, and devices for generating predictive models for subtyping heterogeneous disorders using functional Random Forest (RF) models. The current disclosure also provides various systems, methods, and devices for generating recommendations related to heterogeneous disorders using predictive models.

The term "heterogeneous condition," "heterogeneous syndrome," "heterogeneous medical condition," and their equivalents, as used herein, can refer to a type of medical condition with multiple etiologies. Multiple individuals with the same heterogeneous condition may present with different clinical or pathological symptoms, and may have different recommended treatments. For example, a stroke is a heterogeneous condition, since one individual with a stroke could present with a first collection of symptoms (e.g., slurred speech and muscular weakness) and another individual with a stroke could present with a second collection of symptoms (e.g., discoordination and an abnormal brain scan), even though both individuals are diagnosed with the same condition. Examples of heterogeneous conditions include autism, Attention-Deficit/Hyperactivity Disorder (ADHD), various cancers, asthma, and the like.

A heterogeneous condition may have a plurality of subtypes. The term "subtype," "endotype," "subgroup," and their equivalents, as used herein, can refer to a distinct class of symptoms and/or biomarkers within a heterogeneous condition. In various examples, a first subtype of a heterogeneous condition may have a different prognosis, ideal treatment, and/or disease progression than a second subtype of the heterogeneous condition.

Clinical treatment of heterogeneous conditions can be complicated. In particular, different subtypes of the heterogeneous condition may have different pathobiological mechanisms. Accordingly, ideal treatments for each subtype may be different. Even after an individual is diagnosed with a particular heterogeneous condition, a particular treatment for that condition may be unsuccessful if that treatment is unsuitable for the individual's subtype. Accordingly, identifying an individual's subtype can help clinicians select effective treatments for the individual.

In some cases, a clinician may be able to determine a particular pathobiological mechanism for an individual with a heterogeneous condition by utilizing specialized and/or expensive diagnostic tests and equipment. The clinician may be able to identify one or more biological conditions of the individual that indicate the subtype of the individual. For example, a clinician may be able to determine a pathobiological mechanism for an individual with autism by using functional Magnetic Resonance Imaging (fMRI). However, in low-resource clinical settings, such diagnostic tests may be unavailable. For example, a rural clinic may not have access to an MRI machine capable of performing fMRI scans on local patients. Identifying an individual's subtype using relatively available and/or inexpensive diagnostic tests (e.g., psychological evaluations) may reduce the necessity for expensive and/or invasive diagnostic tests, particularly for patients in low-resource settings.

Despite the advantages of identifying patients with heterogeneous conditions by subtype, it can be difficult for individual clinicians to identify subtypes of heterogeneous conditions. Accordingly, it can be difficult to diagnose individual patients according to subtype. In some examples, human clinicians may not be able to analyze the vast amount of data to identify of heterogeneous conditions in order to identify subtypes. In some cases, clinicians may not have access to enough diagnostic equipment and/or tests to diagnose individual patients according to subtype. With the growing interest and benefits of precision medicine, techniques for accurately and precisely defining subgroups of heterogeneous disorders can provide improvements to clinical diagnosis and treatment.

According to various implementations of the present disclosure, identification of subtypes of a heterogeneous condition can be enabled using machine learning. In particular, ensemble learning and/or graph theory techniques can be utilized to train one or more predictive models to identify subtypes of a heterogeneous condition. Various machine learning models described herein can combine a supervised machine learning model with an unsupervised machine learning model. In some implementations, subtypes are identified by a predictive model (e.g., a functional Random Forest model) that generates multiple decision trees (e.g., by a supervised a Random Forest technique) using training data, and classifying the decision trees according to subtype (e.g., by an unsupervised community detection technique, such as Infomap).

In various implementations, the predictive model, which includes both the decision trees and classification models, can be adjusted and validated using various techniques. For example, the model can be validated by applying control data (e.g., clinical data associated with individuals who do not have the heterogeneous condition) and/or additional training data (e.g., clinical data that is associated with individuals who have the heterogeneous condition, but that was not utilized in generating the initial model) to the predictive model. In some cases, the model can be validated by classifying individuals according to subtype using the model, and then determining whether the individuals of each subtype are associated with distinct biomarkers.

In particular implementations, the predictive model can be used to classify individuals into subgroups, and to generate recommendations for their treatment according to their subgroups. In some examples, a clinical device (e.g., a terminal that stores medical records, a medical imaging terminal, a surgical device, or the like) may transmit a patient's clinical information to a system, the system may apply the predictive model to the clinical information, and the system may return a prediction of the individual's subtype, a recommendation for further diagnostic tests based on the individual's subtype, a recommendation for treatments based on the individual's subtype, or the like. To improve medical privacy, in some cases, information identifying the patient can be encrypted before the clinical information is transmitted from the clinical device, and decrypted once the prediction(s) and/or recommendation(s) are received from the system.

In various implementations, the predictive model can provide relatively accurate subtyping by utilizing at least one ensemble approach. For instance, the plurality of decision trees included in the predictive model can provide more accurate subtyping than a single decision tree, alone.

According to various implementations, systems, devices, and techniques described herein can be implemented in a number of ways. The various functions, gateways, nodes, and components discussed herein can be implemented as a network element on a dedicated hardware, as a software instance running on a dedicated hardware, or as a virtualized function instantiated on an appropriate platform, such as a cloud infrastructure.

Various implementations described herein can utilize a Functional Random Forest (FRF) model to identify subgroups of a heterogeneous condition. In various examples, the FRF model combines machine learning, in this case the Random Forest (RF) model, and graph theoretic analyses, here community detection, to characterize relevant heterogeneity and subtypes of heterogeneous conditions within populations. According to some implementations, the FRF model characterizes unknown heterogeneity with respect to a question associated with the subtypes, by combining supervised and unsupervised approaches. For example, the FRF model identifies subtypes that are tied to a clinical (e.g., a biological and/or cognitive) outcome.

In some examples, data including various features are initially fit to an outcome via a RF model, using cross-validation to assess model performance. The RF model comprises a collection of decision trees. In various cases, a decision tree is a model that splits cases (nodes) via paths comprising a series of binary rules (paired branches). A case flows left or right along the decision tree depending on the application of the rule to the case. Multiple paths in a given decision tree may lead to the same outcome. The input features can include unstructured clinical notes, clinical assessment or task measures, high-dimensional biological data, or the like. For example, a decision tree may be formed to determine whether a child may need educational support in school. One branch might split children by IQ, with those less than 70 requiring support. Another might split children by autism diagnosis, with those diagnosed positively requiring support. In various implementations, each tree is developed randomly. A random subset of the data is used to generate pseudo-random datasets to train each tree. Within each tree, each rule is determined by selecting the rule with the best split from a randomly chosen subset of features. Such random ensembles will ignore features that are noise (with regard to the outcome), unlike purely unsupervised approaches. Accordingly, the FRF model can more accurately identify subgroups than purely unsupervised approaches.

According to various implementations, the RF model can be used to produce a similarity/proximity matrix, which represents the similarity between pairs of individuals, and a score, which represents the probability of the predicted outcome. The proximity matrix from a given RF is then recast as a graph, where nodes reflect participants and edges are weighted by participant-participant proximity. Community Detection, a graph theory approach, can be used iteratively to identify subgroups. One example of a community detection algorithm is Infomap. Infomap uses a random walker that traverses the constructed graph to identify communities, where a subset of individuals (i.e. nodes) contain more edges that connect each other than edges that do not. The technique is robust to many case scenarios. Because Infomap makes few assumptions regarding the number of groups or their composition, the user does not need to specify how many groups are present, unlike the supervised approaches above. Together, these tools represent the FRF in various cases.

According to various implementations, the outcome for the FRF model reflects the initial question asked by the analysis. The proximity matrix can be used to identify whether subtypes exist is built specifically for the predicted outcome variable. If the model performs well, then identified subtypes are likely to be tied to the outcome. For example, an investigator, using the identical data, might define diagnostic subtypes from several clinical variables and demographic variables. Using the same input features distinct subtypes might be drawn from an outcome (e.g., related to future academic performance), which would weight these features differently. The FRF makes few assumptions regarding data inputs, and can implicitly handle categorical and continuous data in the same model.

The potential usage of the FRF model can be applied to heterogeneous conditions, such as stroke. For example, models that could predict who will benefit from a treatment (e.g., Warfarin) for secondary prevention of a subsequent stroke can be generated. However, the true mechanisms of the behavioral sequela of stroke are unknown. Variability with regard to demographics, health history, environmental exposures, symptoms, and CT findings (i.e. hyperintensities, null findings, and hypointesities on the scan) at the time of presentation may be present for different individuals with different stroke-based health outcomes. In addition, it may be known that not everyone with stroke benefits from anti-coagulation. A large population of stroke patients with input features (i.e., demographics, symptoms, etc.) and their long-term outcomes (i.e. prevention of a new stroke or not)

may be obtained. If a purely supervised or unsupervised approach that do not utilize the outcome of interest (i.e. secondary prevention) was used to parse the variability across the features of the population of stroke patients, the purely supervised or unsupervised approaches would likely identify different types of clusters depending on the restraints and bias of a given method. For example, a supervised approach that was set to force the data into two groups might fit the data primarily into males and females because of the precision of this feature in the data set. This subgrouping is valid, but has limited impact on the outcome of interest. Of course, there are nearly an unlimited number of outcomes depending on the actual type of model used and the specified model parameters; however, such supervised approaches limit the chance that the we identify the model specific to our outcome of interest. Unsupervised models, while not requiring such explicit parameters like the number of groups, is also not guaranteed to give an optimal grouping decision that is important for our question or outcome (i.e. prevention of secondary stroke or not when on Warfarin).

Hybrid techniques like the FRF model have an advantage over other machine learning approaches. In various use cases, the same features of the population could be used to generate the FRF model; however, the first stage of the modeling would initially identify whether the features input are capable of predicting the outcome of interest, and then determine which features are important for that prediction (i.e., it would filter out the features of 'no interest' related to secondary prevention). For example, demographic and environmental measures may not be associated with secondary prevention and the use of Warfarin. Therefore, those measures would have limited contributions to the predictions and thus would not be highly weighted when identifying sub-populations (i.e. the proximity matrix and community detection sub-grouping could be driven by the CT scan because CT measures contribute most to predicting the outcome of interest). Importantly, simply changing the outcome of interest (e.g. to exercise therapy effectiveness) would cause the model to weight input features differently. In turn, these differences would inform distinct sub-populations based on the new outcome measure. Accordingly, the FRF model provides a substantial improvement in the technical field of medical diagnosis and treatment by more accurately identifying distinct, clinically relevant subtypes of heterogeneous conditions (e.g., ASD, ADHD, neurodevelopment, stroke, or the like) than previous techniques. Furthermore, the FRF also improves the technical field by identifying more clinically relevant subtypes than previous techniques.

Example Implementations are Provided Below with Reference to the Following Figures.

FIG. 1 illustrates a network configuration 100 according to various implementations of the present disclosure. The network configuration 100 may include a prediction system 104, which may include a Random Forest (RF) model generator 108, a predictive model 110, and a validator 110.

In some implementations, the RF model generator 108 can be configured to generate the predictive model 110, based at least in part, on training data 102. The RF model generator 108 may be configured to generate a plurality of decision trees and to identify a plurality of subtypes based, at least in part, on classifying the decision trees by subtype. In some examples, the decision trees can be classified by a community detection technique, such as Infomap.

The predictive model 110 may include the plurality of decision trees and the subtypes identified by the RF model generator 108. In particular implementations, the predictive model 110 may include at least 1000 decision trees, at least 10,000 decision trees, or some other number of decision trees.

The validator 112 may be configured to validate the predictive model 110. The validator 112 may validate the predictive model based on a subset of the training data 102 and/or control data 114. In some implementations, the subset of the training data used (by the validator 112) to validate the predictive model 110 may be different from the subset of the training data used (by the RF model generator 108) to generate the predictive model 110.

In some implementations, the validator 112 may be configured to remove decision trees from the predictive model 110 based at least in part on one or more of a sensitivity, a specificity, an accuracy, etc., of the decision trees. In some cases, the validator 112 may delete misleading or relatively unhelpful decision trees from the predictive model 110, which may have relatively poor or unreliable subtype prediction power. In certain examples, a first tree may have a first terminal node that has a 10% likelihood of being associated with subtype A, a second tree may have a second terminal node that has a 90% likelihood of being associated with subtype A. The validator 112 may remove the first tree or the first terminal node from the model because the 10% likelihood is below a predetermined threshold (e.g., 50%) and may retain the second tree and the second terminal node in the model because the 90% likelihood is above the predetermined threshold.

In some examples, a first tree may have a 20% likelihood of correctly identifying a plurality of subtypes, and a second tree may have an 80% likelihood of correctly identifying the plurality of subtypes. The validator 112 may remove the first tree from the model because the 20% likelihood is below a threshold (e.g., 40%), and the validator 112 may retain the second tree in the model because the 80% likelihood is above the threshold.

The prediction system 104 may be configured to communicate with a clinical device 106. The clinical device 106 may transmit patient information 116 to the prediction system 104, and the prediction system 104 may return subtype information back to the clinical device, in various implementations. As described herein, the patient information 116 may include diagnostic results associated with an individual patient.

In particular implementations, the prediction system 104 may apply the patient information 116 to the predictive model 110. For example, the prediction system 104 may feed the patient information 116 through each of the plurality of decision trees in the predictive model, and determine at least one candidate subtype for the patient. The subtype of the patient may be predicted to be the candidate subtype returned by the greatest number of decision trees. In some instances, the predictive model may be further determined to assess a likelihood that the predicted subtype is accurate.

The subtype information 118 may be based, at least in part, on the predicted subtype of the patient. In some implementations, the subtype information 118 may indicate the subtype. In particular implementations, the subtype information 118 may include any of one or more recommended diagnostic tests for the patient based on the subtype, one or more treatments for the patient based on the subtype, or the like.

In some implementations, the clinical device 106 may be configured to output the subtype information 118. For example, the clinical device 106 may output an indicator of the subtype information 118 on a display, which can be viewed by a user (e.g., a clinician). In particular implementations, the subtype information 118 can be displayed in the form of an augmented reality feature. For example, if the clinical device 106 is a terminal configured to display a medical image of a patient's brain, the subtype information 118 may include a pointer to an area of interest in the image of the patient's brain based on the patient's predicted subtype.

Figure 2:
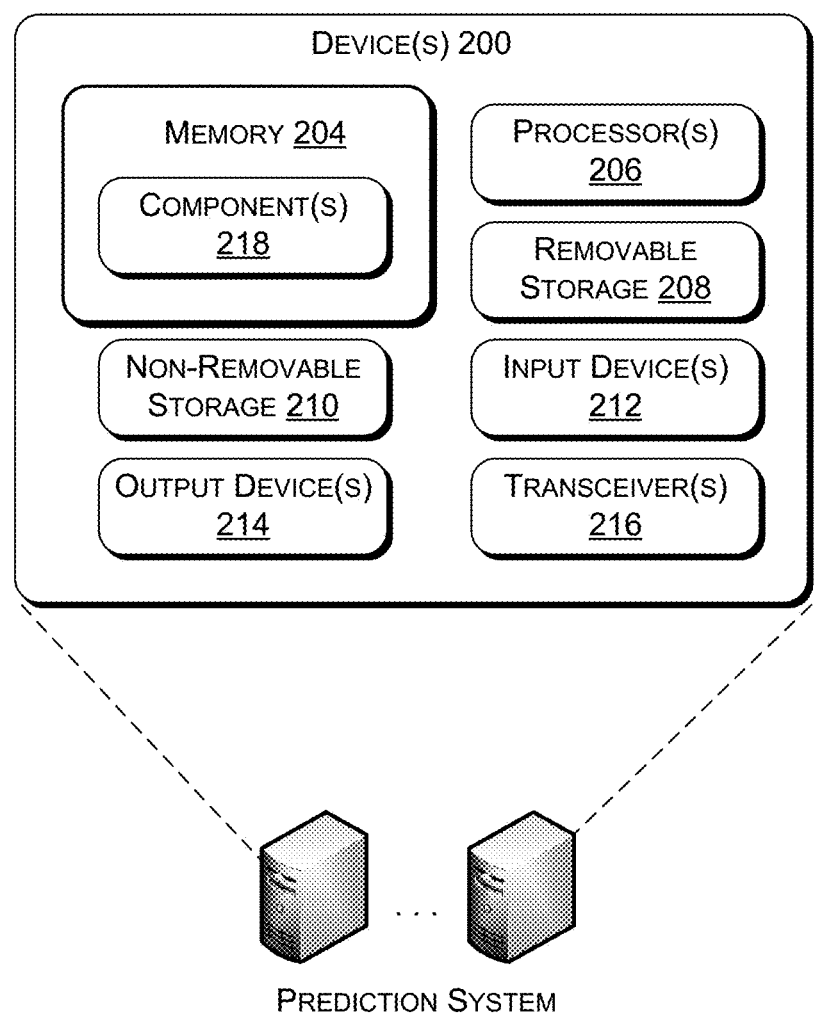
FIG. 2 illustrates a prediction engine according to various implementations of the present disclosure.

FIG. 2 illustrates device(s) 200 corresponding to a prediction engine according to various implementations of the present disclosure. In some implementations, the device(s) 200 may correspond to a prediction system.

The device(s) 200 can include any of memory 204, processor(s) 206, removable storage 208, non-removable storage 210, input device(s) 212, output device(s) 214, and transceiver(s) 216. The device(s) 200 may be configured to perform various methods and functions disclosed herein.

The memory 204 may include component(s) 218. The component(s) 218 may include at least one of instruction(s), program(s), database(s), software, operating system(s), etc. In some implementations, the component(s) 218 include instructions that are executed by processor(s) 206 and/or other components of the device(s) 200. For example, the component(s) 218 include at least one of the RF model generator 108, the predictive model 110, or the validator 112 described above with reference to FIG. 1.

In some implementations, the processor(s) 206 include a central processing unit (CPU), a graphics processing unit (GPU), or both CPU and GPU, or other processing unit or component known in the art.

The device(s) 200 may also include additional data storage devices (removable and/or non-removable) such as, for example, magnetic disks, optical disks, or tape. Such additional storage is illustrated in FIG. 2 by removable storage 208 and non-removable storage 210. Tangible computer-readable media can include volatile and non-volatile, removable and non-removable media implemented in any method or technology for storage of information, such as computer readable instructions, data structures, program modules, or other data. The memory 204, the removable storage 208, and the non-removable storage 210 are all examples of computer-readable storage media. Computer-readable storage media include, but are not limited to, Random Access Memory (RAM), Read-Only Memory (ROM), Electrically Erasable Programmable Read-Only Memory (EEPROM), flash memory, or other memory technology, Compact Disk Read-Only Memory (CD-ROM), Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 200. Any such tangible computer-readable media can be part of the device 200.

The device(s) 200 may be configured to communicate over a telecommunications network using any common wireless and/or wired network access technology. Moreover, the device(s) 200 may be configured to run any compatible device Operating System (OS).

The device(s) 200 also can include input device(s) 212, such as a keypad, a cursor control, a touch-sensitive display, voice input device, etc., and output device(s) 214 such as a display, speakers, printers, etc. These devices are well known in the art and need not be discussed at length here.

As illustrated in FIG. 2, the device(s) 200 also include one or more wired or wireless transceiver(s) 216. For example, the transceiver(s) 216 can include a network interface card (NIC), a network adapter, a Local Area Network (LAN) adapter, or a physical, virtual, or logical address to connect to various network components, for example. To increase throughput when exchanging wireless data, the transceiver(s) 216 can utilize multiple-input/multiple-output (MIMO) technology. The transceiver(s) 216 can comprise any sort of wireless transceivers capable of engaging in wireless, radio frequency (RF) communication. The transceiver(s) 216 can also include other wireless modems, such as a modem for engaging in Wi-Fi, WiMAX, Bluetooth, infrared communication, and the like. The transceiver(s) 216 may include transmitter(s), receiver(s), or both.

Figure 3:
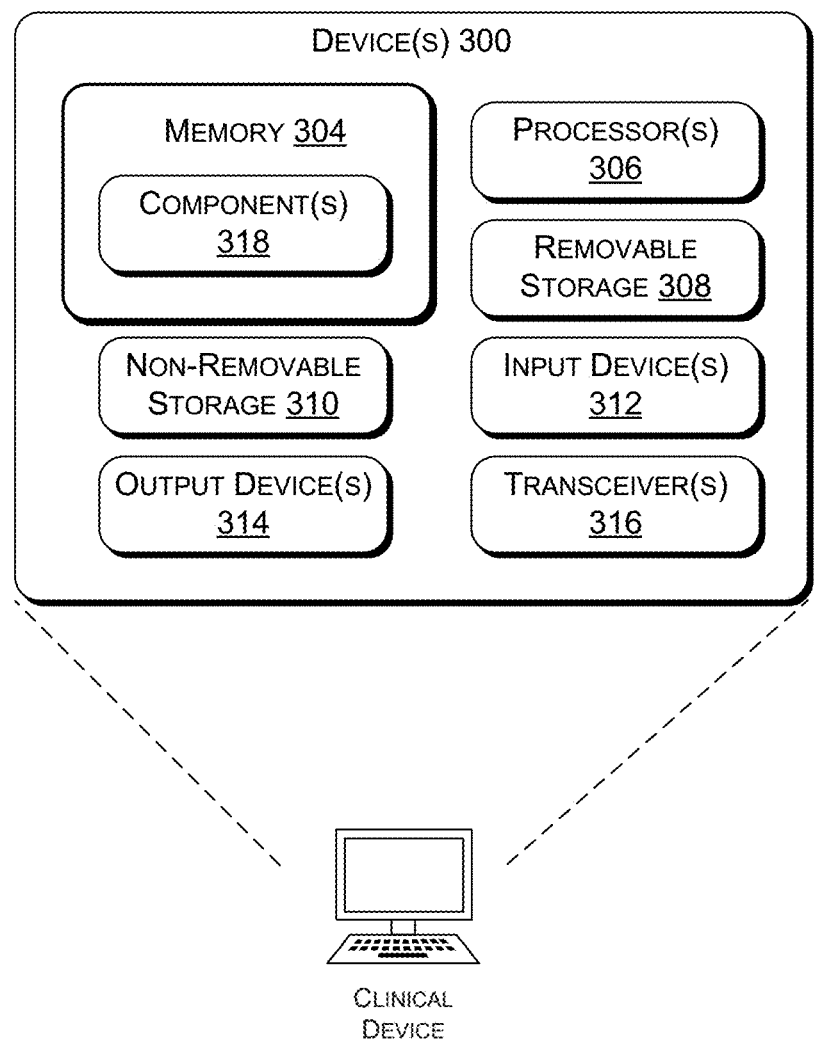
FIG. 3 illustrates a clinical device according to various implementations of the present disclosure.

FIG. 3 illustrates a device(s) 300 corresponding to a clinical device according to various implementations of the present disclosure. In some implementations, the device(s) 300 may correspond to a clinical device.

The device(s) 300 can include any of memory 304, processor(s) 306, removable storage 308, non-removable storage 310, input device(s) 312, output device(s) 314, and transceiver(s) 316. The device(s) 300 may be configured to perform various methods and functions disclosed herein.

The memory 304 may include component(s) 318. The component(s) 318 may include at least one of instruction(s), program(s), database(s), software, operating system(s), etc. In some implementations, the component(s) 318 include instructions that are executed by processor(s) 306 and/or other components of the device(s) 300. For example, the component(s) 318 can include instructions that enable to device(s) 300 to output an indication of a subtype of a heterogeneous condition of an individual, a treatment for the individual based on the subtype, a prognosis of the individual with the subtype, or the like.

In some implementations, the processor(s) 306 include a central processing unit (CPU), a graphics processing unit (GPU), or both CPU and GPU, or other processing unit or component known in the art.

The device(s) 300 may also include additional data storage devices (removable and/or non-removable) such as, for example, magnetic disks, optical disks, or tape. Such additional storage is illustrated in FIG. 3 by removable storage 308 and non-removable storage 310. Tangible computer-readable media can include volatile and non-volatile, removable and non-removable media implemented in any method or technology for storage of information, such as computer readable instructions, data structures, program modules, or other data. The memory 304, the removable storage 308, and the non-removable storage 310 are all examples of computer-readable storage media. Computer-readable storage media include, but are not limited to, Random Access Memory (RAM), Read-Only Memory (ROM), Electrically Erasable Programmable Read-Only Memory (EEPROM), flash memory, or other memory technology, Compact Disk Read-Only Memory (CD-ROM), Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 300. Any such tangible computer-readable media can be part of the device 300.

The device(s) 300 may be configured to communicate over a telecommunications network using any common wireless and/or wired network access technology. Moreover, the device(s) 300 may be configured to run any compatible device Operating System (OS).

The device(s) 300 also can include input device(s) 312, such as a keypad, a cursor control, a touch-sensitive display, voice input device, etc., and output device(s) 314 such as a display, speakers, printers, etc. These devices are well known in the art and need not be discussed at length here.

As illustrated in FIG. 3, the device(s) 300 also include one or more wired or wireless transceiver(s) 316. For example, the transceiver(s) 316 can include a network interface card (NIC), a network adapter, a Local Area Network (LAN) adapter, or a physical, virtual, or logical address to connect to various network components, for example. To increase throughput when exchanging wireless data, the transceiver(s) 316 can utilize multiple-input/multiple-output (MIMO) technology. The transceiver(s) 316 can comprise any sort of wireless transceivers capable of engaging in wireless, radio frequency (RF) communication. The transceiver(s) 316 can also include other wireless modems, such as a modem for engaging in Wi-Fi, WiMAX, Bluetooth, infrared communication, and the like. The transceiver(s) 316 may include transmitter(s), receiver(s), or both.

Figure 4:
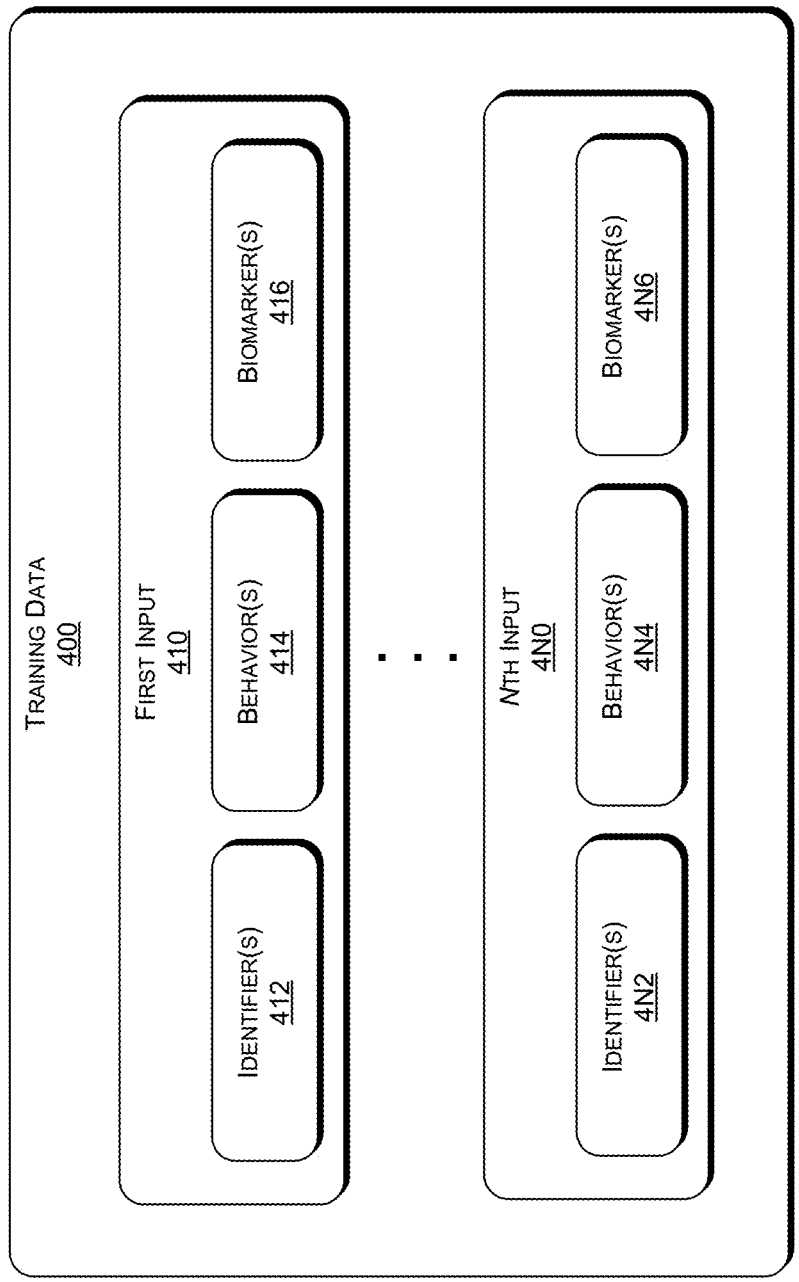
FIG. 4 illustrates training data according to various implementations of the present disclosure.

FIG. 4 illustrates training data 400 according to various implementations of the present disclosure.

The training data 400 may include first through nth inputs 410 through 4N0. Any of the first through nth inputs 410 through 4N0 may correspond to a particular individual's clinical data. For example, the first input 410 may include identifier(s) 412 of a first individual, behavior(s) 414 of the first individual, and biomarker(s) 416 of the first individual. The identifier(s) 412 may identify the first individual by any of an identification code, a name, a gender, an ethnicity, an age, and the like.

The behavior(s) 414 may include clinical data associated with a behavior of the first individual. In particular implementations, the behavior(s) 414 include one or more of: a behavior related to working memory of the first individual; a behavior related to response inhibition of the first individual; a behavior related to temporal reward discounting by the first individual; a behavior related to attentional vigilance of the first individual; a behavior related to processing of a facial feature by the first individual; a behavior related to processing of a vocal affect by the first individual; a behavior related to processing of facial emotion by the first individual; or another type of psychological indicator of the first individual. In various instances, these behaviors can be identified based at least in part on any of tests described below in Example 1.

The biomarker(s) 416 may include clinical data associated with a biological feature of the first individual. In particular implementations, the biomarker(s) 416 may include one or more of medical imaging data (e.g., a Magnetic Resonance Imaging (MRI) scan of the first individual), genetic data (e.g., a genotype of the first individual), analyte levels (e.g., a level of a specific protein in the first individual's blood), or another type of biological indicator of the first individual.

Similarly, the nth input 4N0 includes identifier(s) 4N2, behavior(s) 4N4, biomarker(s) 4N6.

Figure 5:
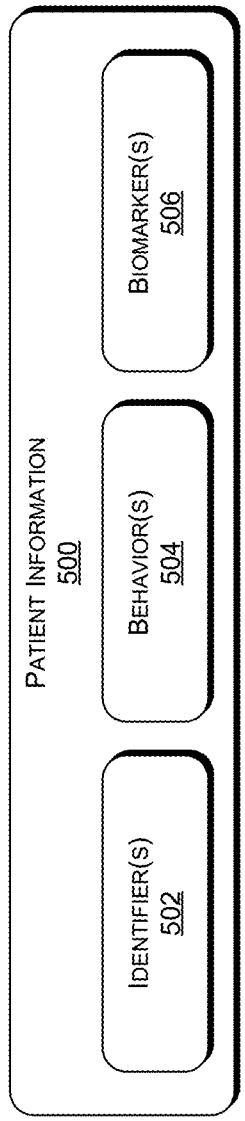
FIG. 5 illustrates patient information according to various implementations of the present disclosure.

FIG. 5 illustrates patient information 500 according to various implementations of the present disclosure. The patient information 500 may include any of identifier(s) 502, behavior(s) 504, and biomarker(s) 506. In some instances, when applied to a relatively sophisticated predictive model, a relatively accurate subtype of the patient associated with the patient information 500 can be determined even when biomarker(s) 506 can be omitted from the patient information 500.

Figure 6:
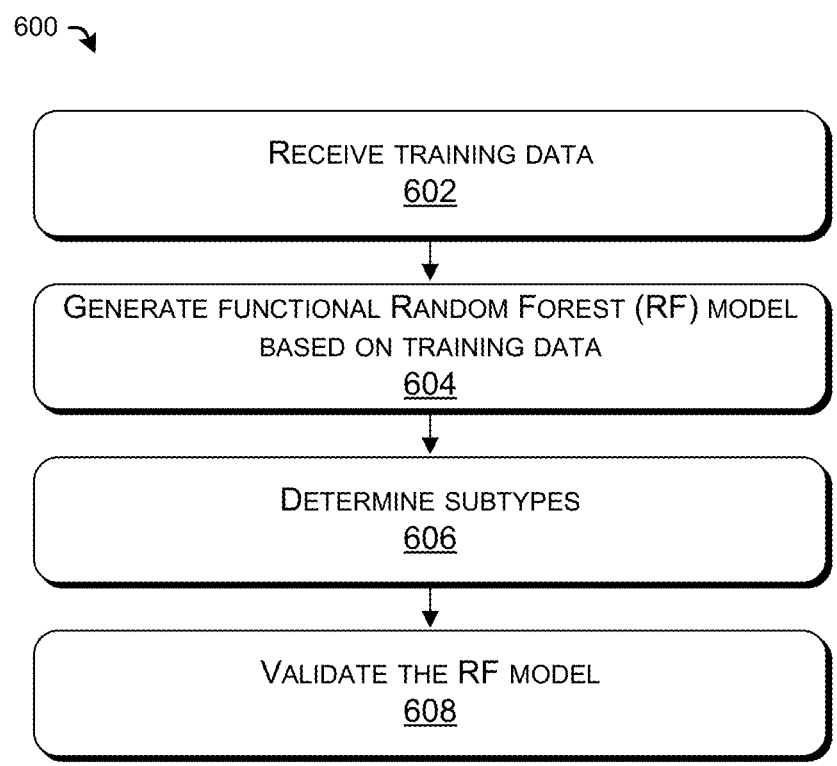
FIG. 6 illustrates a process for establishing a predictive model according to various implementations of the present disclosure.

FIG. 6 illustrates a process 600 for establishing a predictive model according to various implementations of the present disclosure. The process 600 may be performed by a predictive system, for example.

At 602, training data is received. The training data may correspond to clinical information associated with individuals in a sample population. The individuals may include individuals who have a particular heterogeneous condition and individuals who do not have a particular heterogeneous condition. In various implementations, the training data can indicate one or more features of individuals. For example, the features may include demographic information (e.g., age, sex, etc.), results of diagnostic tests (e.g., observed behaviors of the patient, fMRI scans of the patient, biomarkers of the patient, etc.), or the like.

At 604, a functional Random Forest (RF) model may be generated based on the training data. In particular implementations, a plurality of decision trees can be generated based at least in part on a first subset of the training data. Each decision tree may include a plurality of decision nodes. In some cases, each of the nodes corresponds to a decision rule (e.g., in the form of an if-else statement). In some cases, any of the nodes splits into at least two paths. For example, if data is input into a particular node with the decision rule of the form "if A then first path, else second path," and the data includes "A," then the first path is followed. Terminal nodes of a given decision tree correspond to a specific decision. In some instances, at least 1000 decision trees are generated based on the first subset.

At 606, subtypes can be determined based at least in part on the RF model. In some implementations, terminal nodes of the decision trees are evaluated. In particular implementations, a proximity matrix is generated by running a subset (e.g., the first subset or a different subset) of the training data through the plurality of trees. The rows of the proximity matrix may be defined according to each participant in the subset of training data, and the columns of the proximity matrix may be defined according to each participant in the subset of training data. A given entry of the proximity matrix may correspond to an amount (e.g., a percentage) of trees in which the participant defined in the corresponding row and the participant defined in the corresponding column ended up in the same terminal nodes. For example, entry (j, k) can be 50%, where j is a first participant and k is a second participant, and where j and k ended up at the same terminal node in 50% of the decision trees in the RF model.

According to various implementations, subtypes can be identified by applying a community detection technique and/or a graph theory model to the proximity matrix. In certain implementations, the subtypes are identified using Infomap. In some implementations, the subtypes are identified using a non-Infomap clustering and/or community detection technique.

Upon identifying a plurality of subtypes, those subtypes can be correlated to the terminal nodes of the RF model. In various instances, a predictive model can include the plurality of decision trees and their terminal nodes classified into subtype. In some instances, the predictive model can be used to classify new data by subtype.

At 608, a predictive model including the RF model and the determined subtypes can be validated. In some instances, the predictive model is validated using various types of data that can be considered "validation data." For example, the functional RF model may have been trained using non-biomarker-based features of the individuals in the sample population, and the validation data may include biomarker-based features (e.g., fMRI scan results) of the individuals in the sample population, in order to validate a biological basis for the subtypes determined for the RF model.

In some instances, the RF model can be validated using a plurality of null-models. Per null-model, the group assignments can be randomly permuted and the RF procedure above can be performed on the permuted data. If the RF classification models are significantly better than the null models, then the RF models can be interpreted as valid for predicting a given outcome measure. In some instances, an independent samples t-test can be used to evaluate the significance of the RF model performance against the null model performance based on the models' accuracy, specificity, and sensitivity rates. The RF model may be validated, for example, if the model has an above-threshold accuracy, specificity, and/or sensitivity.

In some instances, the RF model can be validated by applying a second subset of the training data to the RF model. The second subset may be different from the first subset.

In certain implementations, the RF model can be validated by applying control data to the RF model. The control data may include information associated with individuals that do not have the heterogeneous condition.

The predictive model can be further validated by comparing biomarker(s) associated with the first and/or second subset of the training data with the identified subtypes. In certain implementations, the subtypes can be associated with particular biological conditions (e.g., a likelihood of a specific analyte identified in the blood, a likelihood of a particular fMRI indicator, etc.). Upon completing process 600, a validated RF model can be generated and used to assist with clinical decision-making.

Figure 7:
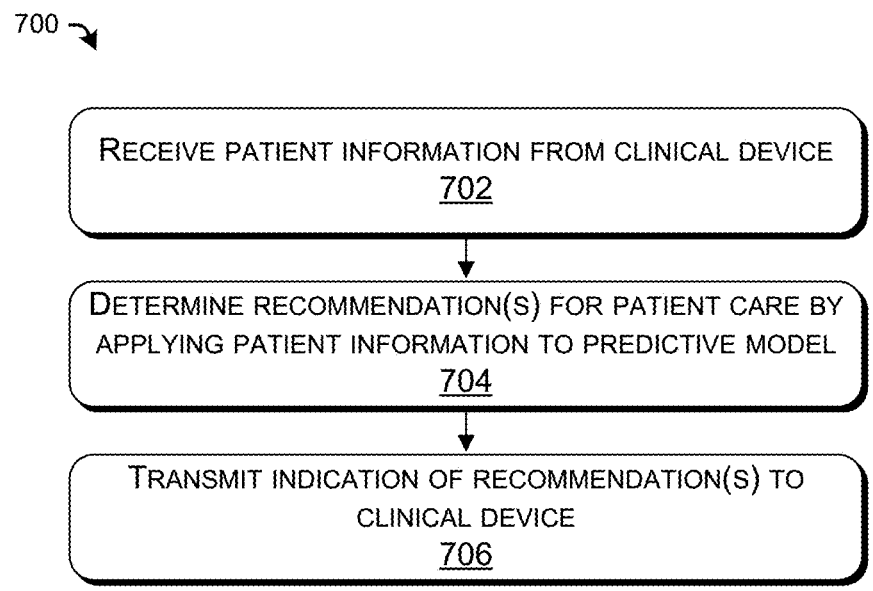
FIG. 7 illustrates a process for providing recommendations(s) to a clinical device using a predictive model according to various implementations of the present disclosure.

FIG. 7 illustrates a process 700 for providing recommendations(s) to a clinical device using a predictive model according to various implementations of the present disclosure.

At 702, patient information associated with a patient may be received from a clinical device. In some implementations, the patient information is encrypted. Once the patient information is received, the patient information may be decrypted. In various implementations, the patient information can indicate one or more features of the patient that are relevant to subtype determination. For example, the features may include demographic information (e.g., age, sex, etc.), results of diagnostic tests (e.g., observed behaviors of the patient, fMRI scans of the patient, biomarkers of the patient, etc.), or the like. In some cases, biomarkers of the patient can be omitted from the patient information.

At 704, recommendation(s) for care of the patient can be determined by applying the patient information to the predictive model. The predictive model may include a functional Random Forest (RF), which includes a plurality of decision trees whose terminal nodes are associated with a plurality of subtypes. The predictive model may have been generated using machine learning (e.g., unsupervised and/or supervised models) and/or graph theory techniques.

In some instances, a plurality of candidate subtypes for the patient are determined by running the patient information through the functional RF model. Each candidate subtype may correspond to a terminal node reached by running the patient information through a given decision tree in the functional RF model. A predicted subtype of the patient can be determined using a "majority vote" analysis. For example, a predicted subtype of the patient may be determined to be one of the plurality of candidate subtypes that is returned by a greatest number of decision trees in the functional RF.

In some implementations, the predictive model may further associate particular subtypes with clinical recommendations. For example, a particular subtype and a particular treatment option may be historically associated with good clinical outcomes in accordance with some treatments. In some examples, the predictive model may have identified that a particular diagnostic test may be helpful before determining a therapy for a particular subtype. Once a subtype of the patient is identified, the predictive model may also determine one or more of these therapeutic and/or diagnostic recommendation(s) for the patient.

In some examples, an ASD subtype of an individual can be identified. Previous patient data may indicate that the ASD subtype responds positively to a particular treatment (whereas an alternative ASD subtype may respond negatively or negligibly to the particular treatment). Treatments for ASD can include, for example, dietary restrictions (e.g., at least one of removing a type of food from the diet, vitamin supplementation, mineral supplementation, or the like), medications, behavioral and/or communication therapies (e.g., at least one of applied behavior analysis (ABA), Discrete Trial Training DTT), Early Intensive Behavioral Intervention (EIBI), Pivotal Response Training (PRT), Verbal Behavior Intervention (VBI), Developmental, Individual Differences, Relationship-based approach (DIR), Treatment and Education of Autistic and related Communication-handicapped Children (TEACCH), sensory integration therapy, speech therapy, occupational therapy, Picture Exchange Communication System (PECS), or the like), or other treatments (e.g., deep pressure treatments, chelation, secretin treatments, or the like). Accordingly, once the subtype of the individual is identified, one or more suitable treatments for the subtype can be further identified based on previously identified treatment efficacies.

In some examples, an ADHD subtype of the individual can be identified. Previous patient data may indicate that the ADHD subtype response positively to a particular treatment (whereas another ADHD treatment may respond negatively or negligibly to the particular treatment). Treatments for ADHD can include, for example, behavioral therapy, medications (e.g., methylphenidate, amphetamine, atomoxetine, guanfacine, clonide, etc.), or the like. Accordingly, once the subtype of the individual is identified, one or more suitable treatments for the subtype can be further identified based on previously identified treatment efficacies.

At 706, an indication of the recommendation(s) may be transmitted to the clinical device. In some instances, the indication is encrypted. In certain implementations, the recommendation(s) may cause the clinical device to display information that can be used to assist a clinician with clinical decision-making. For example, if the patient is predicted to have a particular subtype of a heterogeneous condition that is relatively likely to be resolved with a particular treatment, a recommendation for that treatment (and possibly, indications of related medical literature) could be displayed on the clinician's screen. In some circumstances, if the clinical device is displaying a medical image of the patient (e.g., an fMRI image of the patient's brain), a pointer may be shown on the display pointing to an area of the brain that is correlated with the predicted subtype of the patient.

According to various implementations of the present disclosure, a computer-based Functional Random Forest (FRF) model can be used to capture unknown heterogeneity in clinical outcomes and/or disease profiles. Traditional approaches usually model clinical disorders as homogenous. Investigators typically compare a group of subjects with one of the disorders defined by core symptoms to a group of control subjects without the disorder. Statistical group differences based on psychometrics, functional brain imaging, or genetics are then used to inform models of the disorder. However, there can be evidence that multiple, unique, perhaps even independent pathways can lead to the symptoms that accompany any given syndrome.

According to various implementations of the present disclosure, the FRF approach combines the benefits of network analysis and machine learning approaches. In some implementations, an FRF approach characterizes heterogeneity as it pertains to a clinical disorder or outcome. This approach can be ideal for tackling problems where underlying subgroup composition can be unknown, such as the progression of new diseases, or where the input data may be a mixture of different data types. In addition, the FRF approach can be applied by a computer in order to analyze a large amount of patient data (e.g., medical record data from 100 individuals, 10,000 individuals, 100,000 individuals, or an even greater number of individuals) indicating a large number of features (e.g., 10 features, 100 features, or an even greater number of features) about various individuals, in order to identify distinct subtypes of a heterogeneous condition, which cannot be practically performed in the human mind. Thus, various implementations of the FRF approach enable clinicians to diagnose individuals by subtype of a heterogeneous condition.

The FRF approach may integrate at least one of three validated techniques: Functional Data Analysis (FDA), Random Forest (RF), and Infomap. These techniques make few assumptions about the data, and can therefore map unknown heterogeneity (e.g., characteristics of unknown subtypes of a heterogeneous condition).

Figure 8:
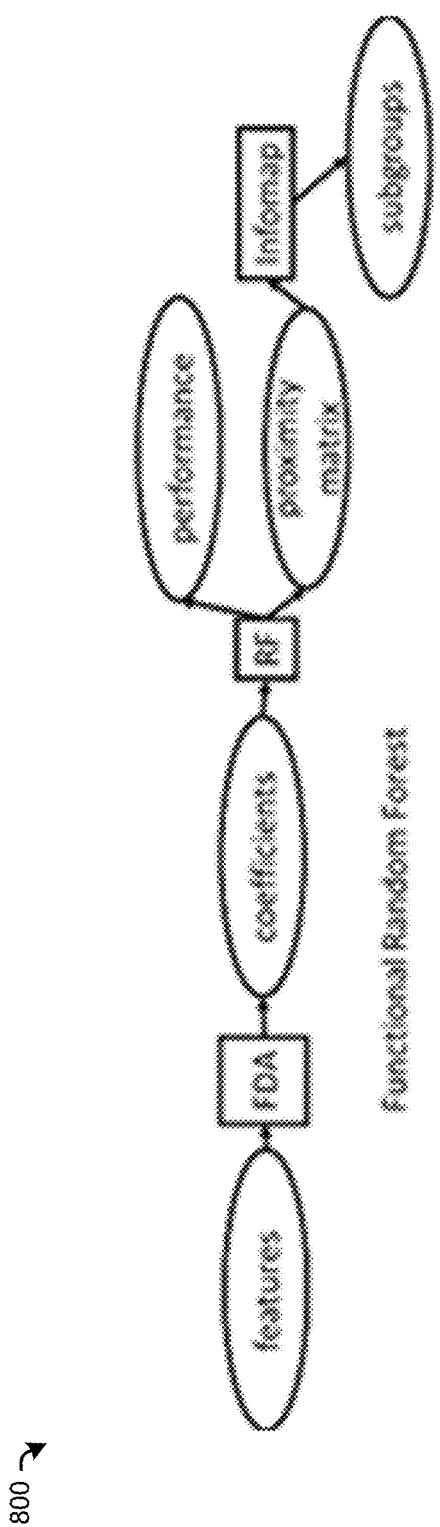
FIGS. 8-10 illustrate various pipelines that can be used to characterize clinical trajectories according to implementations of the present disclosure.

FIG. 8 illustrates an example FRF pipeline that can be used to identify clinical trajectories associated with heterogeneous conditions. A "trajectory," as used herein, may refer to a feature defined as a measurement over time. In particular implementations, such as the one illustrated in FIG. 8, a default FRF pipeline can be used to characterize clinical trajectories. FDA spline-fitting models can make few assumptions about underlying trajectories, and can capture unknown heterogeneous condition symptom (e.g., ADHD symptom) trajectory shapes, which can be entered into an RF model. In various implementations an RF model can be a flexible modeling approach that allows for multiple pathways to the same clinical outcome, and one can measure the similarity between participants from an accurate RF model. In FIG. 8, "performance" can refer to model error estimated from cross-validation or independent testing. For categorical outcomes, model error can be measured by the proportion of test cases that are accurately labeled. For continuous outcomes, model error can be the mean difference between the observed outcomes and predicted outcomes.

In various implementations, the FDA can be generated and/or utilized in a variety of ways. For example, piecewise polynomial functions can be used to fit the trajectory of each symptom per individual and produce a set of coefficients. Knots can be fitted at each of the measured time points. While spline-fitting can handle irregularly collected data, at least 5 timepoints may be used to estimate trajectories. Furthermore, individuals with different age ranges may vary by trajectory due to sampling. Therefore, participants used in this analysis can contain the same minimum and maximum age, such that observed trajectories can be anchored to the same age range. Individuals can be excluded if trajectory values exceed the limits of the assessments.

In various implementations, the RF model can include a random ensemble of decision trees, where each tree can be generated using bootstrapped data from a subset of training data. Per tree, each branch can be determined by selecting the best feature, from a random subset of all the features, that minimizes training error, and the tree can be grown until the training data are classified. For a test or OOB case, each tree can vote on the classification, and the majority vote can determine the class.

As a way to evaluate the success of the approach, while a supervised RF can attempt to classify diagnosis, an unsupervised RF can attempt to classify real from randomly shuffled data, where the relationship between participant and data may be randomized, but the mean and variance of each feature may be preserved. As a result, the relationship between features can be important for prediction. Per tree, each branch can be determined by selecting the best feature, from a random subset of all the features, that minimizes training error, and the tree can be grown until the training data are classified. For a test or OOB case, each tree can vote on the classification, and the majority vote can determine the class. RF performance can be evaluated using the classification error rate to determine whether to identify subgroups from the RF model. Because each tree may have different terminal branches, the RF algorithm may identify different paths for participants with similar outcomes. Therefore, validated models, where accuracy is greater than chance, can be further analyzed to identify putative subgroups that reflect similar outcomes but possibly different etiologies. The RF algorithm can be used to produce a proximity matrix (or similarity matrix), which represents the similarity between pairs of individuals; and a score, which represents the probability of the predicted outcome. While the RF algorithm is powerful, batch effects may be present in the data, which may affect the proximity matrix and subsequent community detection.

In some implementations, putative subgroups can be identified from such similarity measures using Infomap. Infomap can be a graph/coding theory algorithm that robustly identifies communities in graphs. Unlike some other community detection techniques, Infomap makes few assumptions about the size or properties of clinical subgroups, and outperforms other detection methods. In some instances, other techniques can be used for performing community detection and/or clustering.

Figure 9:
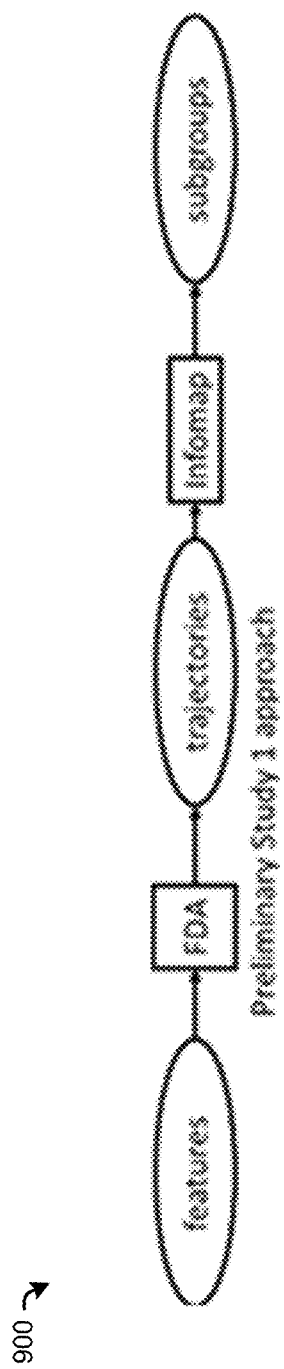

FIG. 9 illustrates an example model to characterize clinical trajectories. In particular implementations, such as the one illustrated in FIG. 9, an alternative model can be used to characterize clinical trajectories, called Functional Trajectories (FTRAJ). This pipeline can derive clinical trajectories using FDA, and for each pair of cases, calculate the association between the trajectories. This can produce a correlation matrix which can be recast as a graph, where infomap can be used to identify subgroups. This technique captures variation in trajectories, but can be insensitive to magnitude differences.

Figure 10:
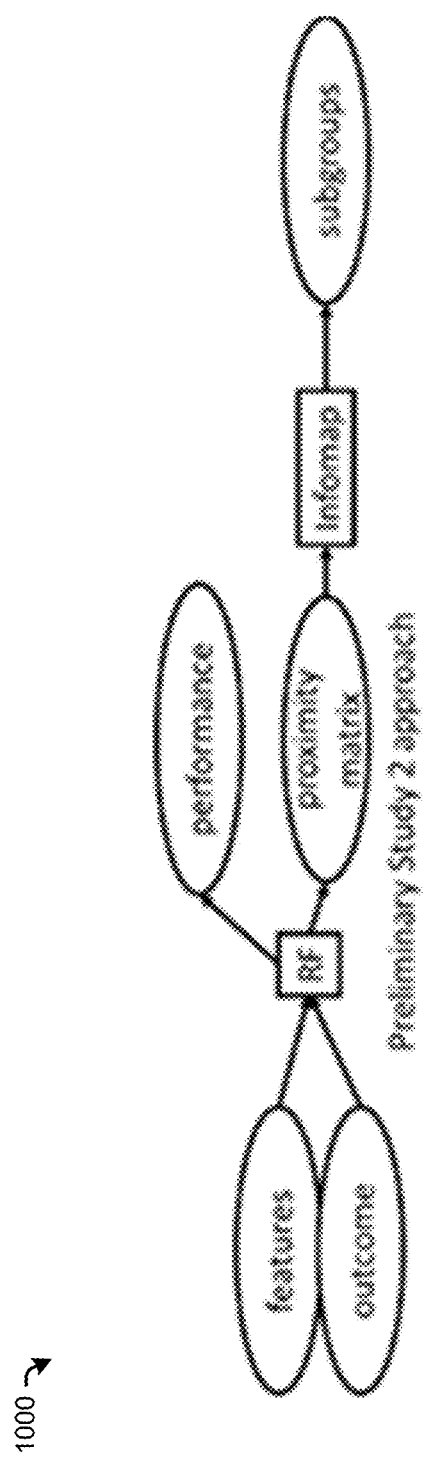

FIG. 10 illustrates an example model to detect subgroups of a heterogeneous condition using clinical outcomes and/or data. A third alternative, called Random Forest Subgroup Detection (RFSD), is shown in FIG. 10. This pipeline characterizes heterogeneity in clinical outcomes. An RF model can be generated from input data by mapping the features to the outcome. In turn, a proximity matrix can be generated from the model and recast as a graph. Using infomap, subgroups are identified from this graph.

Implementations of the present disclosure have a variety of advantages over other technologies. The FRF approach could be applied to any clinical condition. Because the approach does not model population distributions, in some examples, it makes no assumptions about the features input into the model, and can handle multiple data types implicitly. The FRF approach provides an internal method for validating putative subgroups using external data.

The following Example Clauses and Examples 1-4 illustrate various implementations of the present disclosure.

Example Clauses

1. A method, comprising:
receiving testing data; and
generating a functional Random Forest (RF) based at least in part on the testing data.

2. A method of example 1 wherein the testing data comprises at least one behavior and/or at least one biomarker of an individual.

3. A method of example 2 wherein the at least one behavior comprises one or more of:
a behavior related to working memory of the individual;
a behavior related to response inhibition of the individual;
a behavior related to temporal reward discounting by the individual;
a behavior related to attentional vigilance of the individual;
a behavior related to processing of a facial feature by the individual;
a behavior related to processing of a vocal affect by the individual; or
a behavior related to processing of facial emotion by the individual.

4. A method of example 2 or 3 wherein the at least one biomarker comprises one or more of:
a structural Magnetic Resonance Imaging (MRI) image of a brain of the individual;
a functional MRI (fMRI) image of the brain of the individual;
a level of an analyte in the individual;
a pathological indicator of the individual; or
a genotype of the individual.

5. A method of any of examples 1-4 wherein generating the functional RF comprises:
selecting a first subset of the testing data to be training data.

6. A method of example 5 wherein the training data comprises clinical data associated with one or more individuals having a predetermined diagnosis of Autism Spectrum Disorder (ASD).

7. A method of example 5 or 6 wherein generating the functional RF further comprises:
generating a plurality of decision trees using the training data.

8. A method of any of examples 5 to 7 wherein generating the functional RF further comprises:
selecting a second subset of the testing data to be validation data.

9. A method of example 8 wherein the validation data comprises clinical data associated with one or more individuals having a predetermined diagnosis of Autism Spectrum Disorder (ASD).

10. A method of any of examples 7 to 9 wherein generating the functional RF further comprises:
validating the plurality of decision trees using at least one of the training data or the control data.

11. A method of any of examples 7 to 10 wherein generating the functional RF further comprises:
identifying a plurality of Autism Spectrum Disorder (ASD) subgroups based at least in part on the plurality of decision trees.

12. A method of any of examples 8 to 11 wherein generating the functional RF further comprises:
selecting a third subset of the testing data to be control data.

13. A method of example 12 wherein the control data comprises clinical data associated with one or more individuals having a predetermined diagnosis of not having Autism Spectrum Disorder (ASD).

14. A method of any of examples 11 to 13 wherein generating the functional RF further comprises:
determining that the ASD subgroups are distinguishable from a control using the control data.

15. A method of any of examples 11 to 14, further comprising:
generating a predictive model for determining an ASD subgroup of a patient by comparing the ASD subgroups and the at least one biomarker.

16. A system comprising:
one or more processors; and
one or more memories storing one or more components that are executable by the one or more processors to perform operations comprising:
a method of any of examples 1-15.

17. A non-transitory computer-readable medium storing one or more components that are executable by one or more processors to perform operations comprising:
a method of any of examples 1-15.

18. A method comprising:
determining, by a clinical device, a feature of a human subject, the feature comprising at least one behavior, at least one biomarker, or both;
transmitting, by the clinical device to a predictive system, an indication of the feature of the human subject; and
receiving, by the clinical device from the predictive system, an indication of an Autism Spectrum Disorder (ASD) subgroup of the human subject.

19. A method of example 18, wherein the predictive system is configured to generate a functional Random Forest (RF) based at least in part on testing data, to generate a predictive model based at least in part on the functional RF, and to determine the indication of the ASD subgroup of the human subject by applying the indication of the feature to the predictive model.

20. A method of example 18 further comprising:
outputting, on a display of the clinical device, a summary of the ASD subgroup of the human subject.

21. A method of example 20 wherein outputting the summary of the ASD subgroup of the human subject comprises displaying a recommendation for further testing of the human subject based at least in part on the ASD subgroup.

22. A method, comprising
generating a Random Forest (RF) model based on training data; and
determining a plurality of subtypes based at least in part on the RF model.

23. A method of example 22 further comprising receiving the training data.

24. A method of example 22 or 23 further comprising validating the RF model.

25. A method comprising:
receiving patient information from a clinical device;
determining one or more recommendations for patient care by applying the patient information to a predictive model, the predictive model comprising a functional Random Forest (FRF); and
transmitting an indication of the one or more recommendations to the clinical device.

26. A method comprising:
determining, by a clinical device, a feature of a human subject, the feature comprising at least one behavior, at least one biomarker, or both;

transmitting, by the clinical device to a predictive system, an indication of the feature of the human subject; and receiving, by the clinical device from the predictive system, an indication of an Autism Spectrum Disorder (ASD) subgroup of the human subject.

27. A method of example 26, wherein the predictive system is configured to generate a functional Random Forest (RF) based at least in part on testing data, to generate a predictive model based at least in part on the functional RF, and to determine the indication of the ASD subgroup of the human subject by applying the indication of the feature to the predictive model.

28. A method of example 26 or 27 further comprising:

outputting, on a display of the clinical device, a summary of the ASD subgroup of the human subject.

29. A method of example 28 wherein outputting the summary of the ASD subgroup of the human subject comprises displaying a recommendation for further testing of the human subject based at least in part on the ASD subgroup.

30. A method comprising generating a Functional Random Forest (FRF) model based at least in part on training data; and generating a plurality of subgroups based at least in part on the FRF model.

31. A method of example 30, wherein generating the FRF model comprises generating a plurality of trajectory shapes by applying an FDA spline-fitting model a plurality of input features in the training data and entering the plurality of trajectory shapes into a Random Forest (RF) model.

32. A method of example 30 or 31 wherein generating the plurality of subgroups comprises:

generating a proximity matrix based at least in part on the FRF model; and generating the plurality of subgroups by applying an Infomap algorithm to the proximity matrix.

33. A method of any of examples 30-32 wherein generating the FRF model comprises generating the FRF model by mapping a plurality of input features in the training data to a plurality of outcomes in the training data.

34. A method comprising:

deriving a plurality of clinical trajectories based on training data using FDA;

generating a proximity matrix by calculating an association between each pair of individuals in the training data using the clinical trajectories; and generating a plurality of subgroups by applying an Infomap algorithm to the proximity matrix.

35. A system comprising:

one or more processors; and one or more memories storing one or more components that are executable by the one or more processors to perform operations comprising:

a method of any of claims 18-34.

36. A non-transitory computer-readable medium storing one or more components that are executable by one or more processors to perform operations comprising:

a method of any of claims 18-34.

Example 1: Identifying ASD Subgroups Using a Random Forest Model

DSM-5 Autism Spectrum Disorder (ASD) comprises a set of neurodevelopmental disorders characterized by deficits in social communication and interaction and repetitive behaviors or restricted interests, and may both affect and be affected by multiple cognitive mechanisms. Example 1 includes various descriptions of example methods, devices, and systems used to identify and characterize cognitive subtypes within the ASD population using a random forest (RF) machine learning classification model. The model was trained on measures from seven tasks that reflect multiple levels of information processing. 47 ASD diagnosed and 58 typically developing (TD) children between the ages of 9 and 13 participated in this study. The RF model was 72.7% accurate, with 80.7% specificity and 63.1% sensitivity. Using the RF model, the proximity of each subject to every other subject was measured, thereby generating a distance matrix between participants. This matrix was then used in a community detection algorithm to identify subgroups within the ASD and TD groups, revealing 3 ASD and 4 TD putative subgroups with unique behavioral profiles. Differences in functional brain systems between diagnostic groups and putative subgroups were examined using resting-state functional connectivity magnetic resonance imaging (rsfcMRI). Chi-square tests revealed a significantly greater number of between group differences ($p<0.05$) within the cingulo-opercular, visual, and default systems as well as differences in inter-system connections in the somato-motor, dorsal attention, and subcortical systems. Many of these differences were primarily driven by specific subgroups suggesting that the method could potentially parse the variation in brain mechanisms affected by ASD.

Introduction

Issues in Diagnosing and Treating ASD

Lack of Precision Medicine in ASD

Autism Spectrum Disorders (ASD) comprise altered social interactions and/or communication, as well as the presence of stereotyped or repetitive behavior (Constantino, J. N., et al., LANCET. NEUROL. 15, 279-291 (2016)). The prevalence of ASD in the global population has been estimated around 1%, but that number has been growing over the past decade (Fombonne, E, JAMA 289, 87-89 (2003); Mcpheeters, M. L., et al. PEDIATRICS (2011). doi:10.1542/peds.2011-0427). The variability in symptoms, severity, and adaptive behavior impairment within the ASD population (Hill, E. L. TRENDS COGN. SCI. 8, 26-32 (2004)) complicates the development of effective treatments and improved diagnostic measures. Such variation also suggests the possibility of discrete ASD subphenotypes and can be consistent with the evidence that ASD may encompass multiple etiologies (Constantino, J. N., et al., LANCET. NEUROL. 15, 279-291 (2016); Betancur, C., BRAIN RES. 1380, 42-77 (2011)). Therefore, identifying and differentiating subgroups in this population could potentially help refine ASD diagnostic criteria and further the study of precision medicine for individuals with ASD.

Heterogeneity in ASD

The etiology of ASD can be complex, and the ASD diagnosis has been related to multiple cognitive, sensory, and motor faculties (Hughes, J. R., EPILEPSY BEHAV 13, 425-437 (2008)). The focus of this study was on the cognitive domain. A thorough review of cognitive mechanisms underlying ASD suggested that non-social cognitive mechanisms, including reward, executive function, attention, visual and auditory processing, may affect the presentation of social behavior regardless of specific impairment or the existence of domain-specific social cognitive mechanisms (Stone, V. E., SOC NEUROSCI 1, 309-319 (2006)). Seven cognitive domains related to information processing and control that have varying levels of association with ASD were examined: spatial working memory, response inhibition, temporal discounting of reward, attentional vigilance, facial recognition, facial affect processing and vocal affect processing.

Working Memory

Working memory can refer to a limited capacity cognitive system that retains information in an accessible state which supports human thought processes (Baddeley, A. NAT. REV. NEUROSCI. 4, 829-839 (2003)). A vast literature in ASD reveals inconsistent findings as to whether visuospatial working memory may be impaired, suggesting the existence of ASD subgroups, which may drive the observed impairments. Early studies of working memory showed that high (Bennetto, L., et al., CHILD DEV. 67, 1816-1835 (1996)), but not low (Russell, J., et al., J. CHILD PSYCHOL. PSYCHIATRY. 37, 673-686 (1996)), functioning children with autism had impairments in verbal and non-verbal working memory. Another found no differences in working memory between children with or without ASD (Ozonoff, S., et al., J. AUTISM DEV. DISORD. 31, 257-263 (2001)). Measures of non-verbal working memory on a non-spatial and non-verbal self-ordered pointing task correlate with visuospatial memory in children with ASD but not children without ASD (Joseph, R. M., et al., NEUROPSYCHOLOGIA 43, 1400-1411 (2005)). In contrast, children without ASD, but not children with ASD, show a relationship between language ability and verbal working memory (id.). Such heterogeneity may reflect differences in how individuals with ASD utilize visuospatial memory to augment non-verbal working memory, whereas individuals without ASD may utilize language to augment verbal working memory (Joseph, R. M., et al., DEV NEUROPSYCHOL 27, 361-378 (2005)).

More recent studies have supported the hypothesis that children with ASD may use different cognitive mechanisms to support working memory. A large-scale study revealed that children with ASD exhibited lower performance than unaffected children on a spatial span task (Chen, S.-F., et al. PSYCHOL. MED. 1-14 (2016), doi:10.1017/50033291715002238), requiring children to repeat a sequence of fixed spatial locations indicated by a series of changing colors. Interestingly, the ASD participants had significantly lower verbal, but not performance, IQ. This study is consistent with findings from two recent studies on children with ASD (Faja, S., et al., AUTISM RES. 1-11 (2016), doi:10.1002/aur.1608; Bowler, D. M., et al., J. ABNORM. PSYCHOL. 125, 886-893 (2016)), one of which showed that better performance on working memory tasks predicted faster development of play behavior (Faja, S., et al., AUTISM RES. 1-11 (2016), doi:10.1002/aur.1608). However, another recent study found no differences in a similar spatial span task (Macizo, P., et al., J. AUTISM DEV. DISORD. 46, 2956-2967 (2016)). Taken together, all of these findings suggest working memory differences between children with and without ASD are inconsistent, and may be affected by sample differences that comprise different ASD subgroups.

Response Inhibition

Response inhibition can refer here to the ability to inhibit a prepotent response, a lower level component of executive function (Diamond, A., ANNU. REV. PSYCHOL. 64, 135-168 (2013)). Over 40 studies have examined whether response inhibition can be different between individuals with and without ASD (Geurts, H. M., et al., AUTISM RES. 7, 407-420 (2014)). While a number of these studies are underpowered, several use large sample sizes and previously validated psychophysical tests. The results from these studies are quite variable, despite large sample sizes and similar task designs. For example, Geurts and colleagues used a stop task to compare stop signal reaction times between TD and ASD children and found a large effect of diagnosis (Geurts, H. M., et al., J. CHILD PSYCHOL. PSYCHIATRY 45, 836-854 (2004)), while a more recent study employing the same task found only a small effect of ASD when examining commission errors (Adams, N. C., et al., J. AUTISM DEV. DISORD. 42, 1052-1063 (2012)). Although sampling variation may explain divergent results, an interesting possibility can be that heterogeneity in ASD helps explain the inconsistency across the literature (Geurts, H. M., et al., AUTISM RES. 7, 407-420 (2014)).

Temporal Discounting of Reward

Temporal discounting can refer here to the weakening of the subjective value of a reward due to a delay (Critchfield, T. S., et al., JOURNAL OF APPLIED BEHAVIOR ANALYSIS 34, 101-122 (2001)). A few studies (e.g., Demurie, E., et al., DEV. SCI. 15, 791-800 (2012); Demurie, E., et al., RES. DEV. DISABIL. 34, 1870-1880 (2013); Chantiluke, K. et al., PSYCHIATRY RES.—NEUROIMAGING 223, 113-120 (2014)) reveal that those with ASD have altered performance on delayed reward discounting tasks. On average, people naturally prefer immediate to delayed rewards of similar values. Different types of rewards may be discounted differently, and may reflect varying preferences for rewards associated with goal-oriented behavior. For example, individuals with ASD may discount monetary and social rewards similarly, whereas typically developing (TD) individuals discount social rewards more than monetary rewards (Demurie, E., et al., RES. DEV. DISABIL. 34, 1870-1880 (2013)). ASD individuals may also discount monetary rewards more steeply with respect to time than TD individuals (Chantiluke, K. et al., PSYCHIATRY RES.—NEUROIMAGING 223, 113-120 (2014)).

Fair, D. A., et al., FRONT. SYST. NEUROSCI. 6, 80 (2012) Attentional vigilance refers to the ability to maintain an alert state in the absence of an alerting stimulus. It can be often measured using continuous performance tasks (CPTs). ASD performance on CPTs show mixed results. An early study found no difference between children with and without ASD on CPT performance. However, the task used long displays and the parameters of the task were not shifted throughout (Pascualvaca, D. M., et al., J. AUTISM DEV. DISORD. 28, 467-478 (1998)). A more recent study using the same version of the task also failed to find differences between children with and without an ASD. However, they did find differences in EEG signals that are important for sustained and selective attention (Tye, C., et al., EUR. CHILD ADOLESC. PSYCHIATRY 7, e1210-5 (2014)), suggesting that individuals with ASD may use an alternative, perhaps compensatory, strategy to perform similarly on CPTs. Consistent with this hypothesis, individuals with ASD show impaired performance on CPTs where the ratio of distractors to targets (Corbett, B. A., et al., CHILD NEUROPSYCHOL 12, 335-348 (2006)) or inter-stimulus interval (Lundervold, A. J., et al., J. ATTEN. DISORD. 20, 599-609 (2016)) varies over the task duration. On the other hand, increasing attentional demands by crowding the visual display does not seem to affect performance in participants with ASD (Yasuda, Y., et al., WORLD J. PSYCHIATRY 4, 42-48 (2014)).

Processing of Facial Features, Vocal Affect, and Facial Emotion

Previous work has repeatedly suggested that individuals with ASDs may have trouble processing the arrangements of facial features, which may impair facial identity recognition and the ability to link speech to facial expressions. Individuals with ASD show impairments in searching for the eye region on a face (Pruett, J. R., et al., PLOS ONE 8, (2013)). Unlike TD individuals, individuals with ASD are not faster at recognizing a part of the face when it is placed in the context of a whole face (Nakahachi, T., et al., PSYCHIATRY RES 159, 330-338 (2008)), and performance on facial identity recognition is not maintained when the orientation of a face is altered (Morin, K., et al., AUTISM RES. 8, 497-506 (2015)). Impairments in face processing may affect other domains; individuals with an ASD have difficulty integrating visual facial and auditory speech information (Stevenson, R. A., et al., J. AUTISM DEV. DISORD. 44, 1470-1477 (2014)) and do not use visual information from the mouth to guide speech perception (Bebko, J. M., et al., AUTISM RES. 7, 50-59 (2014)).

However, results on facial emotion recognition are more mixed (Annaz, D., et al., J. EXP. CHILD PSYCHOL. 102, 456-486 (2009)). Earlier studies found wide variation in facial emotion recognition performance in adults with an ASD (Barton, J. J. S., et al., BRAIN 127, 1706-1716 (2004); Hefter, R. L., et al., NEUROLOGY 65, 1620-1625 (2005)). More recent studies have shown that facial recognition can be improved in ASD, but that this improvement may not generalize when recognizing emotions from faces (anaka, J. W., et al., J. CHILD PSYCHOL. PSYCHIATRY 53, 1259-1267 (2012)). ASD participants trained to recognize basic emotions like 'happy' or 'sad' for a particular set of identities did not improve recognition on faces from novel identities. Furthermore, ASD participants did not improve at recognizing emotion when the eyes were presented in the context of a whole face, suggesting that such training did not enable individuals with ASD to process the eyes holistically (anaka, J. W., et al., J. CHILD PSYCHOL. PSYCHIATRY 53, 1259-1267 (2012)).

In summary, multiple information processing streams may be affected in individuals with ASD, but the types of impairment may be heterogeneous within the ASD population, with different individuals showing varying patterns of difficulty. Critically, it can be difficult to disentangle from these studies whether individuals with an ASD diagnosis comprise distinct subgroups, as shown by working memory and response inhibition findings. Therefore, it can be critical to test whether ASD can be heterogeneous categorically and/or multi-dimensionally. The identification of distinct ASD subgroups may enable better mapping of the cognitive domains affected by and/or responsible for ASD.

Lack of Clear Biomarkers in ASD

Due to the wide variation in behavioral measures related to ASD, many studies have sought brain-based biological markers to identify a common etiology across individuals with ASD. Markers that are measurable via MRI are highly desirable, because they may represent potential targets for diagnostic tools and or treatments. Unfortunately, the results of these studies are varied due to differences in both study design and sample composition.

Structural Brain Biomarkers Indicating Heterogeneity

Reviews of structural MRI findings in ASD have found a wide range of putative biomarkers across independent studies (Chen, R., et al., PEDIATR RES 69, 63R-8R (2011); Amaral, D. G., et al., TRENDS NEUROSCI (2008); Brambilla, P., et al., BRAIN RES. BULL. 61, 557-569 (2003)). Whole brain-volume (Lange, N., et al., AUTISM RES. 8, 82-93 (2015)) developmental trajectories may differ between individuals with and without ASD. Regionally, the temporal-parietal junction (Dierker, D. L., et al., CEREB. CORTEX 25, 1042-1051 (2015)), anterior insula (Dierker, D. L., et al., CEREB. CORTEX 25, 1042-1051 (2015); Nordahl, C. W., et al., J Neurosci 27, 11725-11735 (2007)), posterior cingulate (Valk, S. L., et al., HUM. BRAIN MAPP. 36, 2364-2373 (2015); Wallace, G. L., et al., J. AM. ACAD. CHILD ADOLESC. PSYCHIATRY 54, 464-469 (2015)), lateral and medial prefrontal (Valk, S. L., et al., HUM. BRAIN MAPP. 36, 2364-2373 (2015)), corpus-callosum (Kucharsky Hiess, R., et al., J. AUTISM DEV. DISORD. 45, 3107-3114 (2015)), intra-parietal sulcus (Nordahl, C. W., et al., J NEUROSCI 27, 11725-11735 (2007); Shokouhi, M., et al., AUTISM RES 5, 245-252 (2012)), and occipital cortex (Wallace, G. L., et al., J. AM. ACAD. CHILD ADOLESC. PSYCHIATRY 54, 464-469 (2015)), have all been shown to be different between samples with and without ASD. This has led a number of reviewers to suggest that the heterogeneity within the disorder may account for the divergent findings (Chen, R., et al., PEDIATR RES 69, 63R-8R (2011); Amaral, D. G., et al., TRENDS NEUROSCI (2008)). Indeed, an interesting study by Christine Nordahl in 2007 examined differences between individuals diagnosed with high-functioning autism, Asperger's, and low functioning autism. Compared to TD individuals, these three samples showed varying cortical folding signatures, indicating that the mechanisms underlying the diagnosis for these samples may differ (Nordahl, C. W., et al., J NEUROSCI 27, 11725-11735 (2007)).

Functional Brain Biomarkers Indicating Heterogeneity

Studies of functional brain biomarkers for ASD have largely centered on studies of resting state functional connectivity MRI (rsfcMRI) for two reasons. First, the hemodynamic response in ASD children has been shown to be largely similar to the hemodynamic response in TD children (Feczko, E., et al., DEV. COGN. NEUROSCI. 2, 396-408 (2012)), suggesting that differences in functional MRI reflect differences in neural activity. Second, the absence of a task enables one to examine differences across multiple brain regions and/or networks, similar to structural MRI.

Unfortunately, findings from rsfcMRI have also varied considerably from study to study. Studies have found altered connectivity within the dorsal attention network (Ray, S., et al., HUM. BRAIN MAPP. (2014), doi:10.1002/hbm.22603); default mode-network (DEF; (Monk, C. S., et al., NEUROIMAGE 47, 764-772 (2009))); whole-brain (Cherkassky, V. L., et al., NEUROREPORT 17, 1687-1690 (2006); Anderson, J. S., et al., CEREB. CORTEX 21, 1134-1146 (2011)) and subcortical-cortical (Di Martino, A., et al., MOL. PSYCHIATRY 19, 659-67 (2014)) underconnectivity; whole-brain (Supekar, K., et al., CELL REP. 5, 738-747 (2013)) and cortical-subcortical (Cerliani, L., et al., JAMA PSYCHIATRY 72, 1-11 (2015)) hyperconnectivity; and altered connectivity within a discrete set of regions dubbed the "social brain" (Gotts, S. J., et al., FRONT HUM NEUROSCI 7, (2013)). Some studies (Redcay, E., et al., FRONT. HUM. NEUROSCI. 7, 573 (2013); Tyszka, J. M., et al., CEREB. CORTEX 24, 1894-1905 (2014)) found no differences in functional connectivity. All of these studies differ not only in MRI processing strategies, but also in the diagnostic inclusion/exclusion criteria. More recent studies (Ray, S., et al., HUM. BRAIN MAPP. (2014), doi:10.1002/hbm.22603; Gotts, S. J., et al., FRONT HUM NEUROSCI 7, (2013); Redcay, E., et al., FRONT. HUM. NEUROSCI. 7, 573 (2013)) also examined differences in processing strategy, but continued to show discrepant results. Taken together, the findings strongly suggest that ASD heterogeneity may limit the replicability of findings.

Machine Learning Approaches in Classifying ASD

Machine learning algorithms provide data-driven methods that can characterize ASD heterogeneity by identifying data-driven subgroups of individuals with ASD. However, most studies using machine-learning algorithms focused only on the identification of individuals with ASD, despite recent studies demonstrating moderate success using such algorithms. A large number of studies have tested whether imaging biomarkers can classify whether an individual has or does not have ASD. Early studies had small sample sizes under 100 individuals and showed high classification rates ranging from 80 to 97 percent accurate (Duchesnay, E., et al., NEUROIMAGE 57, 1003-1014 (2011); Murdaugh, D. L., et al., PLOS ONE 7, (2012); Wang, H., et al., PLOS ONE 7, 1-14

(2012); Jamal, W., et al., J. NEURAL ENG. 11, 046019 (2014)). Larger scale studies greater than 100 individuals typically showed modest accuracy in range of 60 to 80 percent (Katuwal, G. J., et al., PLoS ONE 11, 1-24 (2016); Abraham, A., et al., NEUROIMAGE (2016), doi:10.1016/j.neuroimage.2016.10.045; Chen, C. P., et al., CLIN. 8, 238-45 (2015)). The discrepancies may indicate poor control of motion in some cases or over-fit models in others (Sabuncu, M. R., et al., NEUROINFORMATICS (2014), doi:10.1007/s12021-014-9238-1). Alternatively, the discrepancies might be the result of ASD heterogeneity. Along these latter lines, one of the best classifications of ASD was performed using Random Forests (RF; Chen, C. P., et al., CLIN. 8, 238-45 (2015)). RFs are random ensembles of independently grown decision trees, where each decision tree votes as a weak classifier, and classification into the same group can occur through different pathways. ASD classification was improved when behavioral features were incorporated into models, suggesting that ASD may be stratified by differences in brain function and behavior (Katuwal, G. J., et al., PLoS ONE 11, 1-24 (2016)). Interestingly, random forests can also enable the identification of subgroups (Breiman, L, et al., *Breiman and Cutler's random forests for classification and regression*. Packag. 'random Forest' 29 (2012). doi:10.5244/C.22.54), however, no machine learning approach has attempted to do so for individuals diagnosed with ASD.

Novel Use of Random Forest (RF) in Identifying Subgroups within Sample

In various implementations, a novel approach for using RFs to identify more homogenous ASD subgroups was utilized. RFs can be a random ensemble classification approach that iteratively grows decision trees to classify data. The RF model can produce a proximity matrix that indicates the similarity between participants. This proximity matrix can illustrate how often a pair of subjects were grouped into the same terminal node of each decision tree within the RF and can be similar to a correlation matrix. Conceptually, the proximity matrix can be recast as a graph, and a community detection algorithm (e.g., at least similar to the community detection algorithm described in Rosvall, M., et al, C. T. PROC. NATL. ACAD. SCI. U.S.A 105, 1118-1123 (2008)) can be used to identify putative subgroups. Several recent studies have used community detection to characterize subpopulations (Fair, D., et al., FRONT. SYST. NEUROSCI. 6, 80 (2012)). However, one limitation from the approach is that the community detection approach may not tie the sub-grouping to the outcome measurement of interest. In other words, prior studies have not evaluated whether the similarity measured between participants, which drives the community detection, can be associated with the clinical diagnosis. Thus, an approach that ties the defined subpopulations to the clinical diagnosis can be better equipped to identify clinically relevant subgroups. The combination of random forest classification and community detection can be used assist with this goal.

In Example 1, children were classified with and without ASD using several information processing and control measures. To attempt to validate the group assignments identified from the cognitive measures, the strength of rsfcMRI connections, within or between neural systems, were compared across the identified subgroups. Such a link would provide external evidence that these subgroups differ in functional brain organization as it pertains to an ASD diagnosis.

Participants

Figures 11A, 11B:
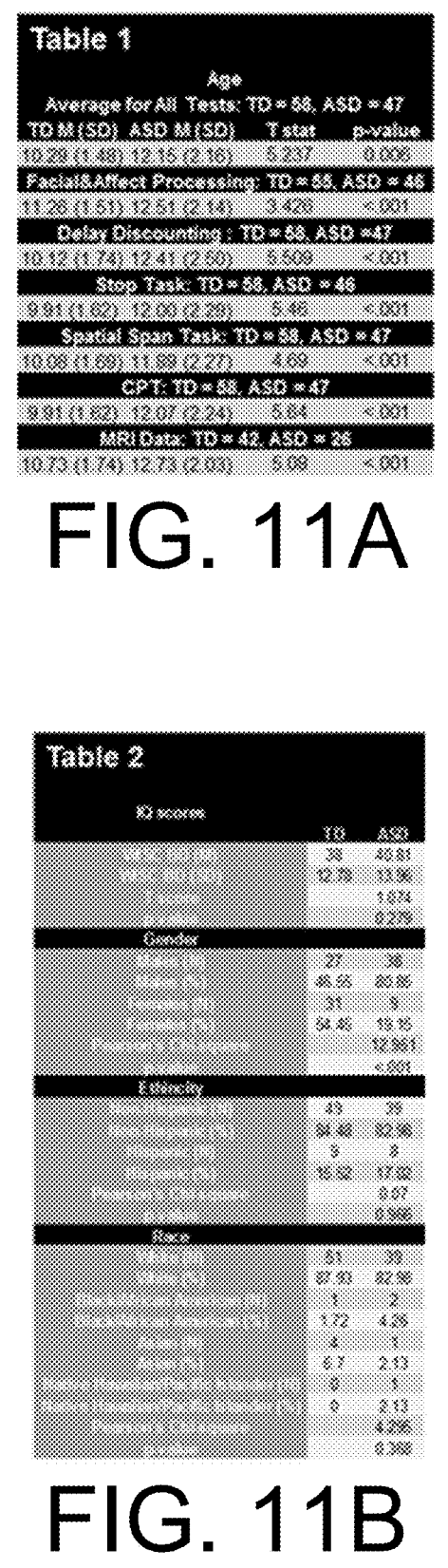

The study sample included data from 105 children between the ages of 9 and 13. Age demographics are shown in Table 1, PDS in Table 1 of FIG. 11A, and all other demographics are shown in Table 2 of FIG. 11B. The ASD group was recruited by community outreach and referrals from an autism treatment center and included 47 children (11 females) with a mean age of 12.15 years (SD=2.12) across all tests. All ASD children had their diagnosis confirmed (using DSM-IV criteria) by a diagnostic team that included two licensed psychologists and a child psychiatrist, and were assessed with a research reliable Autism Diagnostic Observation Schedule Second Edition (ADOS; mean ASD=12.36, SD=3.371), Autism Diagnostic Interview-Revised interview (ADI-R) and by the Social Responsiveness Scale Second Edition (SRS; TD mean=17.8, SD=10.45; ASD mean=92.32, SD=27.02) surveys filled out by parents of the children. The TD group included 58 children (31 females) with a mean age of 10.29 years (SD 2.16) for all tests. A Fisher's exact test indicated that gender was significantly different between the two groups (p=0.025). It should be noted that the gender difference between the groups can be consistent with the hypothesis that males are at increased risk for autism in the general population. Parental pubertal developmental stage (PDS) report was used to assess pubertal stage. The PDS information was acquired once for all participants, but was untied to the tasks or MRI visits, which limited the ability to infer from it. For each MRI and task visit, the difference between the date of PDS acquisition and the date the task/MRI was acquired was calculated. For each task, any participant that had a PDS within 6 months of the task/MRI visit was included. As a result, the reported subject numbers for the PDS, as linked to the task and MRI, vary. However, at least a single PDS measure was acquired for all participants. Median PDS values were calculated from the observable measures on the PDS (e.g. hair growth or skin changes), measures that did not involve observation (e.g. whether the parent will discuss puberty with his/her child) were excluded. Unsurprisingly, differences in PDS were strikingly similar to the differences observed in age (see: FIG. 27). Exclusion criteria for both groups included the presence of seizure disorder, cerebral palsy, pediatric stroke, history of chemotherapy, sensorimotor handicaps, closed head injury, thyroid disorder, schizophrenia, bipolar disorder, current major depressive episode, fetal alcohol syndrome, severe vision impairments, Rett's syndrome, and an IQ below 70. Participants in the TD group were also excluded if diagnosed with attention-deficit hyperactivity disorder. Subjects taking prescribed stimulant medications completed medication washout prior to testing and scanning. Children performed tasks and completed MRI visits following a minimum of five half-life washouts, which ranged from 24 to 48 hours given the preparation. Participants on non-stimulant psychotropic medication (e.g. anxioltyics or anti-depressants) were excluded from this study.

Data Collection Procedures

ASD participants came in for a screening visit to determine if they qualified for the study. During this initial visit, informed written consent or assent was obtained from all participants and their parents, consistent with the Oregon Health & Science University institutional review board. Additionally, children completed the ADOS and the Wechsler Intelligence Scale for Children IV (WISC-IV; 72) block design subtest while parents completed the SRS, ADI-R, and Developmental and Medical History surveys. Participants who qualified for the study came back for a second visit where they completed the Delay Discounting, Spatial Span, CPT, and Stop tasks. All participants also experienced a "mock scanner" to acclimate to the scanner environment and to train themselves to lie still during the procedure. Participants then came in for a third visit where they were scanned. At the fourth visit, participants completed predetermined Face Identity Recognition, Facial Affect Matching, and Vocal Affect Recognition tasks.

Participants in the TD group were recruited from a partner study with similar protocol. During the initial screening visit, participants underwent a diagnostic evaluation based on the Kiddie-Schedule for Affective Disorders and Schizophrenia (KSADS) interview, as well as parent and teacher standardized ratings, which were reviewed by their research diagnostic team. TD participants completed their study visits and tasks in a similar timeline and were recruited for the study during their MRI visit. TD participants were then screened and enrolled in an additional visit in which they completed the Face Identity Recognition, Facial Affect Matching, and Vocal Affect Recognition tasks.

Most of the participants consented to a longitudinal study where they returned on an annual basis to be reassessed on these same tasks and were re-scanned. For this study, data from each participant's earliest time point for each completed task and MRI scan was used. Per task and scan, a t-test was conducted to test whether the cross-sectional ages were significantly different for that test. In all cases, ASD participants were significantly older than TD participants (all p<0.05). Non-verbal intelligence, as measured by the WISC block design, was controlled for by ensuring that block design scores were not significantly different between the groups (p=0.285). The difference in visit age for the ASD (mean years=1.51, s.d. (years)=1.36) and typical (mean years=1.14, s.d. (years)=1.17) samples selected was also calculated and tested. No significant group effects on average visit difference (t(103)=1.49, p=0.14) were observed.

Tasks

Figure 12:
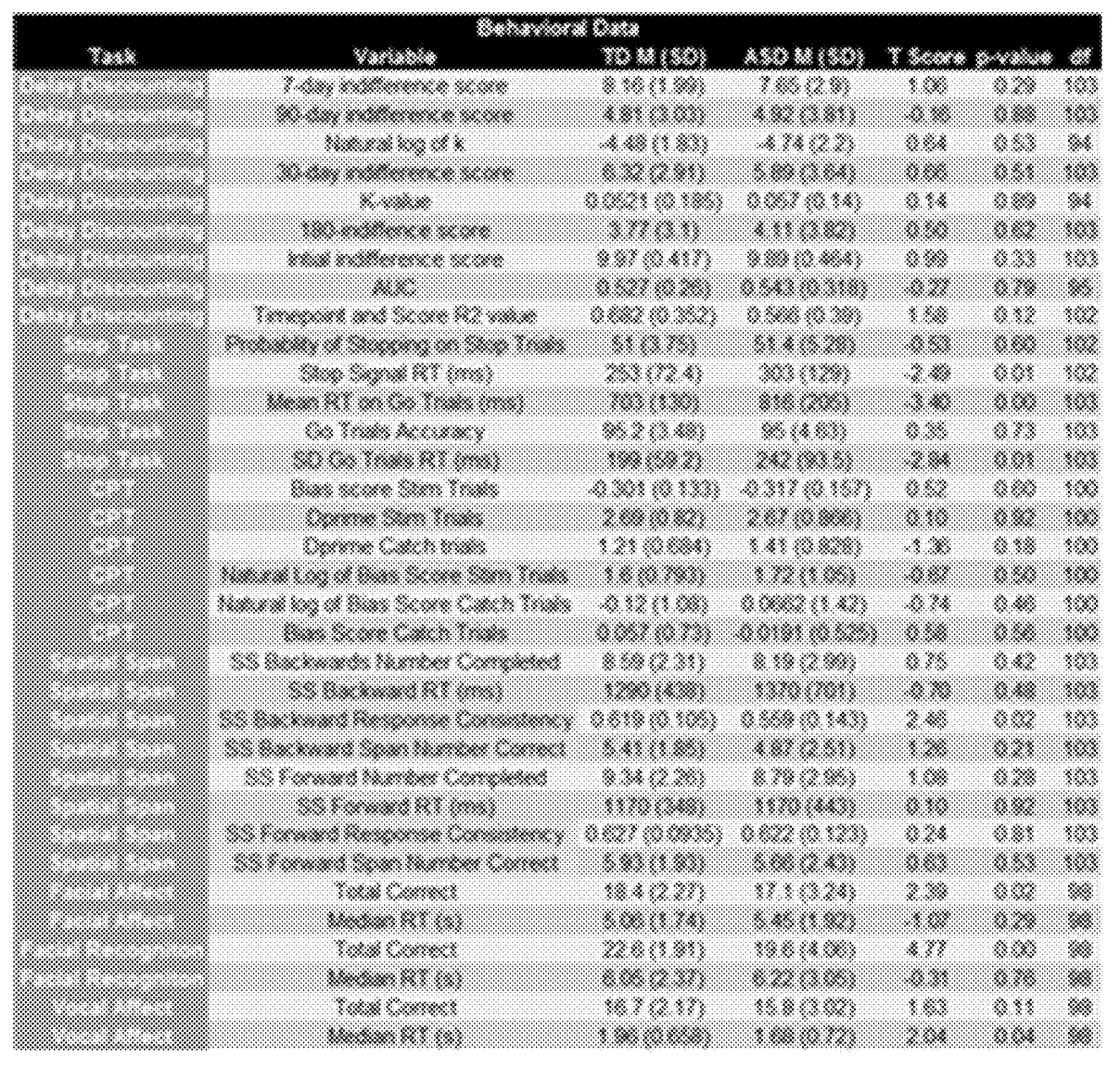

Measures derived from seven tasks were used as input features for the random forest. These seven tasks cover multiple levels of information processing, which may affect or be affected by the presence of an ASD diagnosis. Per measure, an independent samples, two-tailed, t-test was conducted to evaluate whether ASD and TD participants differed significantly. Table 3 of FIG. 12 lists each feature along with the t-statistic and p-value associated with the test. Because the random forest approach can be robust against the presence of non-predictive features (Breiman, L. E. O., MACH. LEARN. 45, 5-32 (2001)), the initial feature selection was inclusive. Despite this liberal inclusion, these non-predictive features did not contribute meaningfully to the classification model and thus did not affect results materially (see, e.g., Example 2).

Delay Discounting

The Delay Discounting task measures an individual's impulsivity by asking them to evaluate a reward's subjective value following a delay. The task design employed here has been described in detail previously (Mitchell, S. H., PSYCHOPHARMACOL. 146, 455-464 (1999); Wilson, V. B., et al., J. CHILD PSYCHOL. PSYCHIATRY 52, 256-264 (2011)). In short, this computerized task consisted of 91 questions and requested participants to choose between two hypothetical amounts of money, one smaller amount that would be available immediately, and one larger amount that would be available after a fluctuating delay (between 0 to 180 days). No actual money was obtained. 9 variables from this task were used in the RF model: the indifference score at 5 time points (7, 30, 90, or 180 days), the calculated area under the curve (AUC) based on these indifference scores, the proportion of variance explained between the scores and their timepoints, their k value (a measure of overall rate of discounting), and the natural log-transformation of these k values. Three validity criteria were applied (see, e.g., Johnson, M. W., et al., EXP. CLIN. PSYCHOPHARMACOL. 16, 264 (2008)): 1) an indifference point for a specific delay could not be greater than the preceding-delay indifference point by more than 20% ($2); 2) the final (180 day) indifference point was required to be less than the first (0 day) indifference point, indicating evidence of variation in subjective value of rewards across delays; and 3) the 0-day indifference point was required to be at least 9.25. Lower values for the 0-day indifference point indicate that the child chose multiple times to have a smaller reward now over a larger reward now, suggesting misunderstanding or poor task engagement. Data that did not meet validity criteria were treated as missing in analyses.

Spatial Span

The Spatial Span task measures an individual's visuospatial working memory capacity. Participants received a spatial span subtest identical to the computerized Cambridge Neuropsychological Test Battery (CANTAB; (Robbins, T. W., et al., DEMENTIA 5, 266-281 (1994))). Briefly, this computerized task presents a series of 10 white boxes randomly placed on the screen, a subset of which would change color in a fixed order. Participants were instructed to watch for boxes that changed color and to keep track of their sequence. In the spatial forward task, participants were instructed to click on the boxes in the same sequential order in which they were presented. In the spatial backward task, participants were instructed to click on the boxes in the reverse order in which they were presented. The tasks were counterbalanced, and every subject had the opportunity to practice before administration. At the beginning of both tasks, the numbers of squares that changed started at three and increased to nine, with two trials at each sequence length (a total of 24 trials for both tasks). The task discontinued when a child failed both trials at a sequence length. 8 measures from this task were used in the RF model: reaction time, accuracy, number completed, and span number correct for both the forward and backward tasks.

Stop Task

A tracking version of the Logan stop task was administered to all participants. The Stop Task can be a dual go-stop task. The go portion of the task measures reaction time and variability of reaction time on a simple choice detection task; the stop portion measures speed at which the individual can interrupt a prepotent response (how much warning is needed). For this computerized task participants fixated on a small cross in the center of computer screen, which appeared for 500 ms on each trial. For the "go trials" (75% of total trials), either a rainbow "X" or an "O" would appear on the screen for 1000 ms. Participants then had 2000 ms to indicate whether they saw an "X" or an "O" using a key press, after which the next trial would automatically start. The "stop trials" (25% of total trials) were identical except that an auditory tone was played briefly after the presentation of the visual cue. The timing of the tone was varied stochastically to maintain approximately 50% success at stopping. Participants were instructed to not respond with the key press if they heard the tone. Each participant performed 20 practice trials to ensure they understood the task, before completing eight 32 trial blocks of the task. 5 measures from this task were used in the RF forest model: accuracy of the X/O choice on "go-trials", probability of successful stopping on the "stop-trials", stop signal reaction time (computed as the difference between go RT and timing of the stop delay warning signal), mean reaction time on go-trials, and the standard deviation of reaction times during "go-trials".

Continuous Performance Task

The Continuous Performance task was an identical-pairs version of the common CPT, which measures vigilance. For this computerized task, participants viewed a series of four digit numbers (250 ms per cue) and were instructed to press a button whenever they saw a pair of identical numbers back-to-back. The task consisted of three types of trials: 1) trials where the paired numbers were made of distinct digits called "stim trials", 2) trials where paired numbers only differed by one digit called "catch trials" and 3) trials where the pair of numbers were identical (target trials). The task included a total of 300 stimuli and required about 10 minutes to complete. There were 20% target trials, 20% catch trials, and 60% "stim" or non-target trials. 6 measures from this task were used in the RF model: dprime (a measure of discriminability, see, e.g., Green, D. M. & Swets, J. A. SIGNAL DETECTION THEORY AND PSYCHOPHYSICS. (Wiley, 1966)) per discrimination type (essentially, "hard" and "easy" discriminations), bias score for each discrimination type, and the natural log of bias per discrimination type.

Face Identity Recognition Task

Figure 13A:
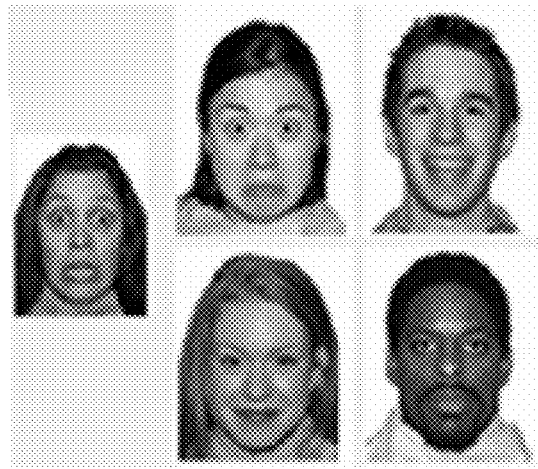
Figure 13B:
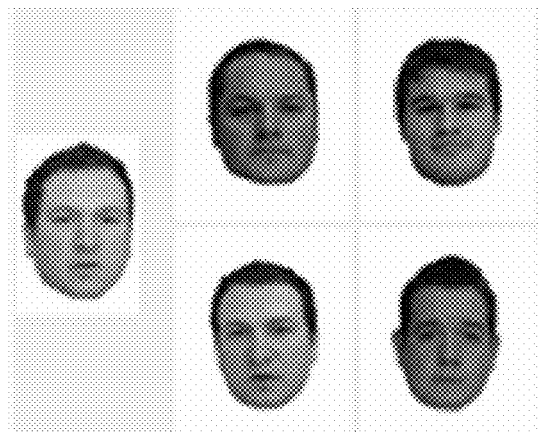

The Face Identity Recognition Task was to measure facial processing skills. In this computerized identification task, for each of the 25 trials (inter-trial interval=2 s), participants were presented with a "target face" on the left side of the screen, a colored photograph of a human face presented in standardized poses with neutral facial expressions. At the same time, participants were shown an additional four facial photographs on the right side of the screen (all photographs were selected from the Glasgow Unfamiliar Faces Database (Burton, et al., BEHAV. RES. METHODS 42, 286-291 (2010)), see FIG. 13B), one of which matched the target face. Participants were asked to select the target face out of the lineup by touching the screen with stylus pen. Reaction times were calculated from the moment the trial began to the participant's response; however, participants were not told they were being timed or instructed to complete the task as quickly as possible. Each participant was allowed five practice trials to ensure they understood the task. Two measures from this task were used in the RF model which included the number of correct responses and the median reaction time for all trials.

Facial Affect Matching Task

The Facial Affect Matching Task and was designed to measure affect discrimination skills using facial expressions. In this computerized task, for each of the 25 trials (inter-trial interval=2 s), participants were presented with a "target emotion", a colored photograph of a human face expressing one of six possible emotions (happiness, sadness, surprise, disgust, fear or anger), on the left side of the screen. At the same time, participants were shown an additional four facial photographs on the right side of the screen (all photographs were selected from the NimStim set of facial expressions; see FIG. 13A; see, e.g., Tottenham, N., et al., PSYCHIATRY RES 168, 242-249 (2009)), one of which matched the target emotion. Participants were asked to select the target emotion out of the lineup by touching the screen with stylus pen. Reaction times were calculated from the moment the trial began to the participant's response; however, participants were not told they were being timed or instructed to complete the task as quickly as possible. Each participant was allowed five practice trials to ensure they understood the task. Two measures from this task were used in the RF model which included the number of correct responses and the median reaction time for all trials.

Vocal Affect Recognition

Figure 13C:
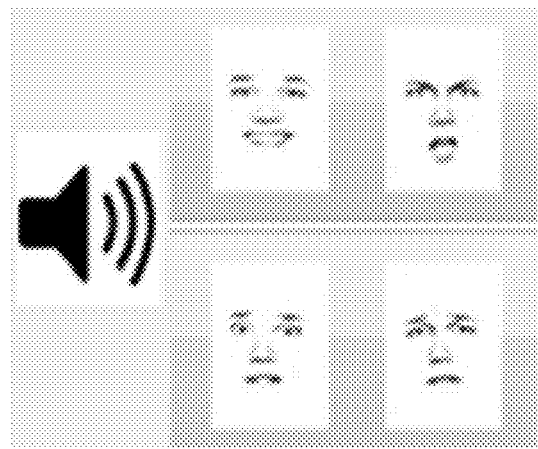

The Affect Matching Task was designed to measure affect discrimination skills using auditory cues. In this computerized task, for each of the 24 trials (inter-trial interval=2 s), participants were presented with an audio recording of an actor reading neutral phrases (e.g., "we leave tomorrow") but expressing one of four possible emotions (happiness, sadness, fear or anger) during the reading. Participants were asked to identify what type of emotion the actor was expressing by selecting one of four black and white drawings of facial expressions, each depicting one of the 4 basic emotions (see FIG. 13C). Reaction times were calculated from the moment the trial began to the participant's response; however, participants were not told they were being timed or instructed to complete the task as quickly as possible. Each participant was allowed four practice trials to ensure they understood the task. 2 measures from this task were used in the RF model which included the number of correct responses and the median reaction time for all trials.

MRI Scans

Data Acquisition

Participants were scanned in a 3.0 T Siemens Magnetom Tim Trio scanner (Siemens Medical Solutions, Erlangen, Germany) with a 12 channel head coil at the Advanced Imaging Research center at Oregon Health and Science University. One T1 weighted structural image (TR=2300 ms, TE=3.58 ms, orientation=sagittal, FOV=256×256 matrix, voxel resolution=1 mm×1 mm×1.1 mm slice thickness), and one T2-weighted structural image (TR=3200 ms, TE=30 ms, flip angle=90° FOV=240 mm, slice thickness=1 mm, in-plane resolution=1×1 mm) was acquired for each participant. Functional imaging was performed using blood oxygenated level-dependent (BOLD) contrast sensitive gradient echo-planar sequence (TR=2500 ms, TE=30 ms, flip angle=90°, in-plane resolution 3.8×3.8 mm, slice thickness=3.8 mm, 36 slices). For fMRI data acquisition, there were three 5-minute rest scans where participants were asked to relax, lie perfectly still and fixate on a black cross in the center of a white display.

General Preprocessing

The functional images went through identical Human Connectome Project preprocessing pipelines as described previously (Glasser, M. F., et al., NEUROIMAGE 80, 105-24 (2013)) in order to reduce artifacts. These pipelines included 1) PreFreeSurfer, which corrects for MR gradient and bias field distortions, performs T1w and T2w image alignment, and registers structural volume to MNI space; 2) FreeSurfer (Fischl, B., NEUROIMAGE 62, 774-781 (2012)), which segments volumes into predefined cortical and subcortical regions, reconstructs white and pial surfaces, and aligns images to a standard surface template (FreeSurfer's fsaverage); 3) PostFreeSurfer, which converts data to NIFTI and GIFTI formats, down sampled from a 164 k to a 32 k vertices surface space, applies surface registration to a Conte69 template, and generates a final brain mask. 4) fMRIVolume, which removes spatial distortions, performs motion correction, aligns fMRI data to the subject's structural data, normalizes data to a global mean, and masks the data using the final brain mask, and 5) fMRISurface which maps the volume time series to a standard CIFTI grayordinate space.

Functional Connectivity Processing

The resting state functional connectivity MRI data received additional preprocessing that have been widely used in the imaging literature (see, e.g., Power, J. D., et al., NEUROIMAGE 84, 320-341 (2014)) to account for signals from non-neuronal processes. These steps included: 1) removal of a central spike caused by MR signal offset, 2) slice timing correction 3) correction for head movement between and across runs, 4) intensity normalization to a whole brain mode value of 1000, 5) temporal band-pass filtering (0.009 Hz<f<0.08 Hz), 6) regression of nuisance variables: 36 motion related parameters, and three averaged signal timecourses from the grayordinates, white matter, and cerebrospinal fluid (CSF). Additionally, because previous research has indicated that minor head movement can result in changes in MRI signal, motion-targeted "scrubbing" was performed on all rs-fcMRI data (Power, J. D., et al., NEUROIMAGE 84, 320-341 (2014)). These steps included censoring any volumes with frame displacement (FD)>0.2 mm, and the elimination of any run with less than a total of two and a half minutes of data.

Correlation Matrix Generation

All timecourses and correlations were derived from a set of 333 Regions of Interest (ROIs) produced from a published data-driven parcellation scheme (FIG. 16) 86, and a set of 19 subcortical areas parcellated by FreeSurfer during preprocessing. The resulting parcellations set comprised 352 ROIs. Correlations between ROIs were calculated using Pearson product-moment coefficient between each pair of ROIs over the extracted time series following preprocessing and motion censoring. A correlation matrix was created for each participant and then created group correlation matrices by averaging individual matrices across groups and subgroups.

Data Analysis

Exploratory Data Analysis

Prior to construction of the RF model, the quantity of missing data was measured. Machine-learning model performance can be greatly affected by missing data. Therefore, any measures and participants that were missing more than 15 percent of data were excluded. The remaining missing data was imputed separately for the training and test datasets using the random forest algorithm below, where the missing data's column is the outcome measure and the remaining variables are used as predictors. Prior to the exploratory data analysis, there were a total of 143 subjects (73 ASD, 70 TD) with partially completed data. After eliminating subjects with more than 15 percent missing data, the subject list was finalized down to 105 subjects (47 ASD, 58 TD). In the final dataset, less than 3 percent of all possible data was missing. An inspection of the missing data was unable to find any patterns that distinguish the missing ASD data from the remaining cases.

Random Forest Classification

General Algorithm

The RF algorithm constructs a series of decision trees. Per tree, a bootstrapped dataset can be generated from a subset of the training data and a subset of features are randomly used to predict group classification or outcome measure in the case of imputation. The Gini impurity can be used as the cost function to determine the optimal tree for classification and the mean square error can be used as the cost function to determine the optimal tree for regression. Finally, a testing dataset comprising participants that were excluded from the training dataset can be used to evaluate classification model performance.

In Example 1, this algorithm was implemented via in-house custom-built MATLAB programs that used the MATLAB TreeBagger class. 1000 trees were used for the classification model and 20 trees were used for the surrogate imputation. Missing data was imputed separately for training and testing datasets. For classification, 1000 iterations of the RF algorithm were run to assess the performance of the RF models. Per iteration, 60 percent of participants formed the training dataset and the remaining 40 percent formed the testing dataset.

Optimization and Validation

Distributions of overall, ASD, and control accuracy were constructed from the 1000 iterations and compared against a distribution of 1000 null-models. Per null-model, the group assignments are randomly permuted and the RF procedure above can be performed on the permuted data. If the RF classification models are significantly better than the null models, then the RF models are interpreted as valid for predicting a given outcome measure. An independent samples t-test was used to evaluate the significance of the RF model performance against the null model performance based on the models' accuracy, specificity, and sensitivity rates.

Community Detection

Since each tree has different terminal branches, the RF algorithm may identify different paths for participants with the same diagnosis. Therefore, validated models can be further analyzed to identify putative subgroups that reflect the same diagnosis but perhaps different etiologies. Briefly, the RF algorithm produces a proximity matrix, where the rows and columns reflect the participants and each cell represents the proportion of times, across all trees and forests, a given pair of participants ended in the same terminal branch. For the classification model, the Infomap algorithm was used to identify putative subgroups from the proximity matrix for participants with an ASD and from the proximity matrix for control participants. Because there was no basis for determining what constitutes an edge, an iterative procedure was used (Karalunas, S. L., et al., JAMA PSYCHIATRY 71, 1015-24 (2014)), where a consensus set of community assignments was identified across possible thresholds.

Radar Plot Visualization

Task measures were then examined via radar plots to identify features that distinguish putative subgroups. Since plotting all measures may obscure differences between the groups, visualized task measures were chosen via statistical testing. For the ASD and the TD samples separately, one-way ANOVAs, with subgroup as the factor and each subgroup a level, were conducted for each task measure. Significant ($p<0.05$) task measures were chosen for visualization. Individual task measures were converted to percentiles and visualized by task.

Functional Connectivity Cluster Analysis

A chi-square approach was used to identify potential differences between subgroups within or between functional systems, as opposed to individual functional connections (Eggebrecht, A. T., et al., CEREB. CORTEX 1-12 (2017), doi: 10.1093/cercor/bhw403). Briefly, three sets of mass univariate tests were conducted for Fisher-Z transformed functional connections: a set of one-way ANOVA using ASD subgroup as the factor, a set of one-way ANOVAs using control subgroup as the factor, and a set of t-tests between ASD and control groups. Per set, a matrix of coefficients are extracted and binarized to an uncorrected $p<0.05$ threshold. This binary matrix can be then divided into modules based on the published community structure (Gordon, E. M., et al., CEREB. CORTEX (2014), doi:10.1093/cercor/bhu239) which reflects groups of within system (e.g. connections within the default mode system) and between system (e.g. connections between the default mode system and the visual system) functional connections. The subcortical parcellation was defined as its own system for this analysis because of prior research suggesting differences between cortical and subcortical connectivity (Di Martino, A., et al., MOL. PSYCHIATRY 19, 659-67 (2014)). A ratio of expected significant to non-significant functional connections (i.e. the expected ratio) can be calculated by dividing the total number of significant connections by the total number of all connections. Per module, the number of expected significant and non-significant functional connections can be determined by multiplying the expected ratio by the total number of functional connections within the module. A chi-squared statistic can be then calculated using the observed and expected ratio of significant connections. Permutation tests were conducted for all functional connections across the 352 ROIs to calculate the p value per module, and evaluate whether the observed clustering is greater than what would be observed by random chance.

Results

Random Forest Classification Results

Random Forest Successfully Classified Individuals as Having ASD or not

RF model accuracy is shown in FIGS. 14A to 14E. Applying the RF algorithm on behavioral data from 7 different tasks (34 variables) achieved an overall classification accuracy of 73% (M=0.727, SD=0.087) and an independent sample t-test revealed that the RF model was significantly more accurate than the permutation accuracy measure of 51% [M=50.9, SD=0.103; t (1998)=51.325, p<0.001]. The RF model had a sensitivity of 63% (M=0.631, SD=0.153) when classifying ASD subjects, the ability to correctly identify true positives, and an independent sample t-test revealed that the model's sensitivity was significantly higher compared to the permutation sensitivity of 44%. [M=0.441, SD=0.166; t (1998)=26.643, p<0.001]. The RF model also had a specificity of 81% (M=0.807, SD=0.153) when classifying control participants, the ability to correctly identify true negatives, and an independent sample t-test revealed that this was significantly more accurate compared to the permutation specificity of 56%. [M=0.564, SD=0.153; t (1998)=40.501, p<0.001]. Taken together, these findings show that the RF model identified patterns in the cognitive data that stratified individuals with an ASD diagnosis from individuals without. (Note: Due to confound age and gender factors, a secondary RF analysis was performed on the behavioral data, controlling for both factors. Despite the large confounds, the RF analysis accurately classified ASD from control participants greater than chance.

Proximity Matrices from Random Forest Model Suggest Subgroups in ASD and Control Samples Next, applied community detection was applied to the proximity matrices generated through the random forest modeling. The community detection algorithm identified three putative ASD subgroups and four putative control subgroups (FIGS. 14A to 14E). For children with an ASD diagnosis, the largest subgroup comprised 25 individuals, while the other two subgroups numbered 13 and 9 children respectively. For children without an ASD diagnosis, the largest subgroup comprised 39 individuals; three other subgroups were evenly split with five, five, and three children respectively. Six controls were not identified as part of any community, which were placed into a fifth "unspecified" subgroup. To characterize these subgroups, variation in accuracy of classification between subgroups was examined, and then variation in the task measures between the subgroups was examined.

ASD Subgroups Differed in Terms of Classification Accuracy

Next, the classification accuracy of individuals within each ASD subgroup was compared to see if specific subgroups may have differentially affected RF model performance FIGS. 14A to 14E. It also allowed for validation that these subgroups were indeed systematically different from one another based on the cognitive data used in the RF model.

Because multiple RFs were constructed, each subject was included in the test dataset a large number of times, therefore the rate of accurate classification per subject was calculated. A one-way between subjects ANOVA was conducted to compare the rate of classification accuracy between the 3 ASD subgroups identified by community detection. There was no significant difference between the groups [F (2, 44)=1.859, p=0.168]. An independent sample t-test was conducted to see if subgroup classification accuracy significantly differed from chance (0.5) using a Bonferroni adjusted alpha level of 0.0167 per test (0.05/3). Subgroup 1 was significantly better at classification than chance [M=0.726 SD=0.367; t (24)=3.0732, p=0.005] but subgroups 2 [M=0.607 SD=0.383; t (12)=1.01, p=0.334] and subgroup 3 [M=0.443 SD=0.431; t (8)=−0.399, p=0.701] were not.

These results suggest that there may be differences in the subgroups that are important for distinguishing ASD from TD. This difference can be subtle, because effects of subgroup on accuracy are small and could largely be driven by the small sample size in subgroups 2 and 3. However, variation in classification accuracy may reflect differences in cognitive profiles. Subjects in subgroup 3 had a classification accuracy of only 44%, which may indicate that these individuals had cognitive scores more similar to the control group than the ASD group, while subgroup 1 had a classification accuracy of nearly 73% suggesting that their cognitive scores may be far different from both the control group, and ASD subgroup 3.

Control Subgroups Differed in Terms of Classification Accuracy

The classification accuracy of individuals within each control subgroup was also compared, to again see if specific subgroups were differentially affecting the RF model's performance (FIGS. 14A to 14E).

A one-way between subjects ANOVA was conducted to compare classification accuracy for each of the 4 control subgroups plus the controls that were lumped into a fifth subgroup, identified by community detection. There was a significant effect of subgroups on classification accuracy [F (4, 53)=24.018, p<0.001]. Post-hoc comparisons using an independent-sample t-test indicated that the classification accuracy for subgroup 5 (M=0.120 SD=0.086) was significantly worse (using a Bonferroni adjusted alpha level of 0.006 per test) than subgroup 1 [M=0.922 SD=0.137; t(43)= −13.871, p<0.001], subgroup 2 [M=0.804 SD=0.422; t(9)= −3.910, p=0.004], and subgroup 4 [M=0.995 SD=0.0089; t(7)=−16.903, p<0.001], but not subgroup 3 [M=0.636 SD=0.362; t(9)=−3.411, p=0.008]. Additionally, an independent sample t-test was conducted to see if subgroup classification accuracy significantly differed from chance (0.5) using the Bonferroni adjusted alpha level of 0.006 per test. Participants in subgroups 1 [t (38)=19.276, p<0.001] and 4 [t (2)=96.00, p<0.001] were classified as controls significantly more than chance, while participants in subgroup 5 [t (5)=−10.773, p<0.001] were classified as controls significantly less than chance.

Community Detection Identified these Subgroups in ASD and Control Samples Who Differed in Behavioral Tasks and Classification Accuracy To test whether ASD subgroups may reflect quantitative variation in autism symptom severity, it was examined whether identified ASD subgroups varied by Social Responsiveness Scale (SRS). A one-way ANOVA revealed no significant differences between the subgroups on SRS (FIG. 14E; F (2, 44)=0.006, p=0.994), suggesting that ASD subgroups had similar autism severity but varied in other ways. Because normal variation in cognitive profiles may affect the manifestation of a developmental disorder (Fair, D., et al., FRONT. SYST. NEUROSCI. 6, 80 (2012)), the variation in task performance for ASD (FIG. 15, left) and control (FIG. 15, right) subgroups were then examined. For control subgroups, the fourth subgroup was not examined due to the small sample size and the fifth subgroup was not examined because it represented "unspecified" subjects. A series of subgroupXtask measure repeated measures ANOVA were performed to assess whether task performance should be examined between specific subgroups. The ASD subgroups (F(66, 1056)=7.65, p=7.5*10-54), control subgroups (F(66, 1452)=2.19, p=2.4*10-7), and accurately identified subgroups (F(33, 1716)=10.64, p=3.3*10-49) showed significant differences across task, indicating that identified subgroups varied by task measure. Post-hoc one-way ANOVAs identified 11 significant different features for control subgroups (F (2, 46)>3.29, p<0.0462) and 16 significant different features for ASD subgroups (F (2, 44)>3.45, p<0.0405). For both ASD and control subgroups, similar relative cognitive profiles were observed. The largest subgroup in both cohorts performed best on stop and continuous performance tasks. The second largest subgroup in both cohorts had the smallest spatial span, and the highest accuracy and longest reaction times for the facial and affect processing tasks. The third subgroup in both cohorts was characterized by highest spatial span, but lowest accuracy and shortest reaction time for the face processing tasks. Participants who show a combination of low accuracy and short reaction time may be showing a speed accuracy trade-off (MacKay, D. G., PSYCHO. REV. 89, 483-506 (1982)), where individual participants are making quicker responses at a cost of more accurate responses. For the most part, delayed discounting did not differentiate the subgroups, which may be because evidence is mixed whether delayed discounting varies by ASD or ASD subgroups. A prior study suggests that ASD and control subgroups discount monetary rewards similarly (Demurie, E., et al., RES. DEV. DISABIL. 34, 1870-1880 (2013)); the relationship between discounting and time varies by ASD subgroup, which can be consistent with findings from a separate study where some ASD participants may discount monetary rewards more steeply than controls (Chantiluke, K. et al., PSYCHIATRY RES. —NEUROIMAGING 223, 113-120 (2014)). The similar cognitive profiles observed between controls and ASD subgroups suggests that normal variation in cognitive profiles may impact how ASD manifests in individuals.

Functional Connectivity Results

Functional Connectivity Differences Between ASDs and Controls

Figure 16:
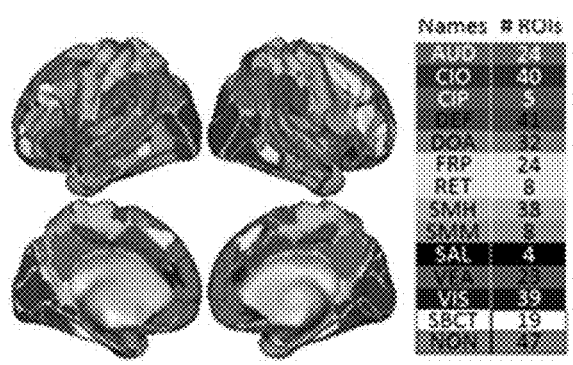
Figure 17A:
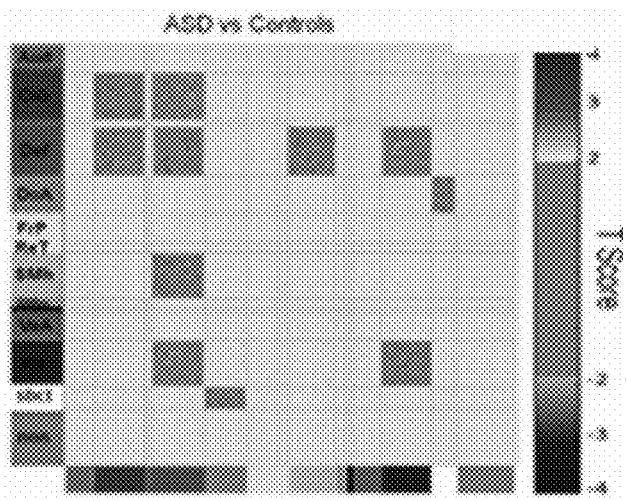

To test the hypothesis that the ASD and controls groups differed in terms of resting-state functional connections between, and within, different functional systems, the chi-squared approach, described earlier, was used. The Gordon parcellation plus 19 subcortical regions were used to define the modules (FIG. 16). The analysis was conducted on the 26 ASD subjects and 42 control subjects with satisfactory fMRI data (FIG. 17A). The chi-squared analysis revealed significant clustering effects between the cingulo-opercular system and the default mode system ($\chi 2$=48.86, p=0.0002), the somato-motor hand system and the default mode system ($\chi 2$=12.81, p=0.0016), the visual system and default mode system ($\chi 2$=11.74, p=0.001), and between the subcortical system and the dorsal attention system ($\chi 2$=35.05, p=0.0024). It also revealed significant clustering effects within the cingulo-opercular ($\chi 2$=259.36, p=0.0002), the default mode system ($\chi 2$=11.66, p=0.0002), and the visual system ($\chi 2$=35.05, p=0.0002). These findings are consistent with prior reports of rsfcMRI differences between TD and ASD samples.

Subgroup Differences within ASD and Control Samples

Figure 17B:
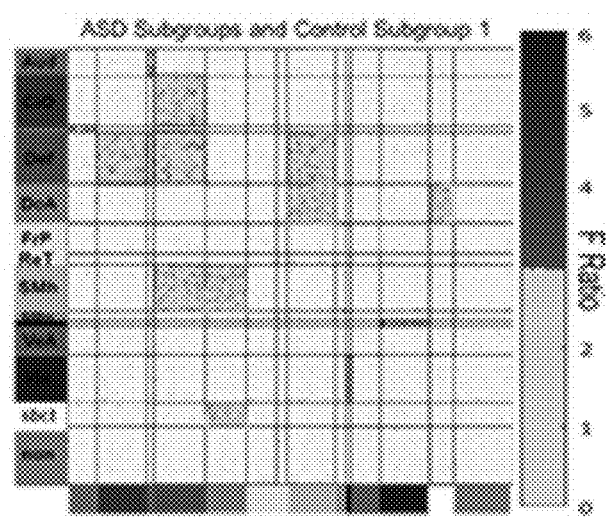
Figure 17C:
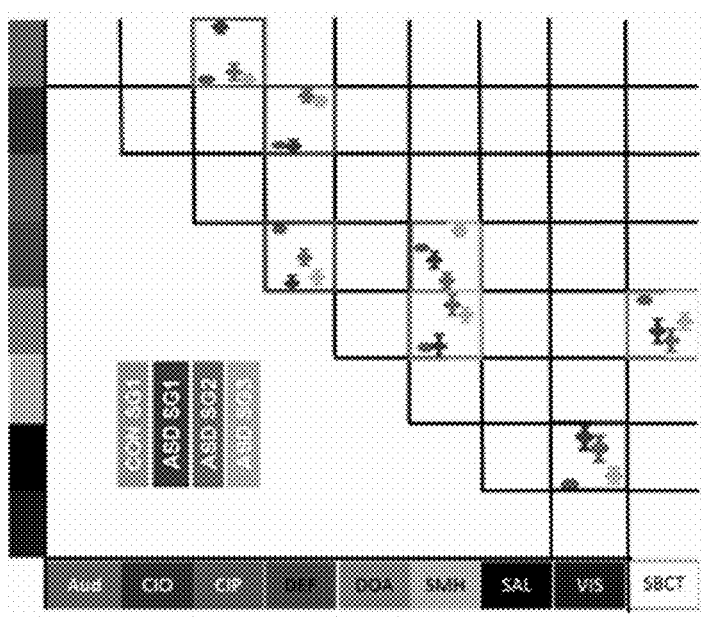
Figure 18:
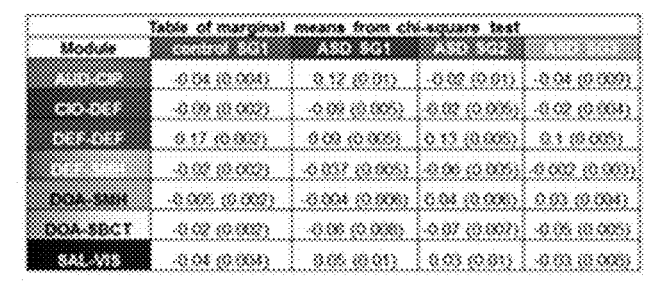

Because ASD subgroups differed in classification accuracy with respect to chance (FIG. 14C), whether variance between each of the ASD subgroups and the large control subgroup differed in terms of resting-state functional connections between, and within, different function systems, was tested using the chi-squared analysis. Unfortunately, due to the MRI 'scrubbing' procedure, there was not sufficient data in the other control subgroups to include them in this analysis. A one-way ANOVA was conducted with four groups on 57 subjects: the 31 subjects from Control subgroup one, 12 subjects from ASD subgroup 1, 8 subjects from ASD subgroup two, and 6 subjects from ASD subgroup three who had satisfactory fMRI data. A permutation test was used to determine each system's expected ratio and compared this to the observed ratio using the chi-squared analysis (FIG. 17B). The estimated marginal means from the ANOVA was used to visualize which subgroups drove significant clustering (FIG. 17C). This test revealed significant increases in connectivity for ASD subgroup 1, relative to all other subgroups, between the cingulo-parietal system and the auditory system ($\chi 2$=12.06, p=0.0014). Significant increases in ASD subgroup 2 and 3 between the cingulo-opercular system and the default system ($\chi 2$=24.01, p=0.0002), and between the dorsal attention system and the somato-motor hand system ($\chi 2$=15.37, p=0.0006). Significant increases in ASD subgroup 1 and 2 connectivity between the salience system and the visual system ($\chi 2$=11.36, p=0.0016). Significant increases in control connectivity were observed within the default system ($\chi 2$=22.36, p=0.0010) and between the dorsal attention system and the subcortical system ($\chi 2$=11.85, p=0.002). Connectivity between the default system and the somato-motor hand system ($\chi 2$=28.85, p=0.0002) showed mixed results, with ASD subgroups deviating from controls. The estimated marginal means for these tests are summarized in FIG. 18.

These differences overlapped substantially with the differences observed between ASD and controls (FIG. 17A), suggesting that normal variation in mechanisms that are also affected by ASD may cause variation in how ASD may manifest (Constantino, et al., LANCET. NEUROL. 15, 279-291 (2016); Szatmari, P., et al., JAMA PSYCHIATRY 72, 276-83 (2015)). These findings should be interpreted cautiously, however, because these data are not predictive of diagnosis.

Discussion

Accuracy of the Random Forest Model

Link of Results to Prior Findings Using Machine Learning ASD Classification

Using a RF model, ASD and control participants were accurately classified 73 percent of the time using a comprehensive battery of cognitive tasks often identified as affected by an ASD diagnosis. Despite differences in age between samples, it is unlikely that the accurate classification was driven by age for two primary reasons. First, task measures important for classification did not show strong correlations with age (see: supplemental materials for discussion, Example 2); when corrected for multiple comparisons, no relationships between gender and task performance are observed. Second, a second RF model controlling for age and gender across all features was performed, which continued to perform above chance (see: supplemental materials for discussion, Example 2).

Higher performance has been reported for behavior when constructing a model using visual face scanning (88.1%; Liu, W., et al., AUTISM RES. 9, 888-898 (2016)) or goal-oriented reach (96.7%; Crippa, A., et al., J. AUTISM DEV. DISORD. 45, 2146-2156 (2015)) measures. However, high classification accuracy may be a function of validation strategies or sample size. Liu et al used a leave-one-outcross validation (LOOCV) strategy, which improves classification accuracy within a test dataset, but may reduce the generalizability of the model to other datasets. Crippa et al. also used a LOOCV validation strategy, and were also limited in sample size. Machine learning approaches using imaging data have shown that validation accuracy decreases as the sample size increases, suggesting that these small sample sizes may be overfitting the data (Katuwal, G. J., et al., PLOS ONE 11, 1-24 (2016); Sabuncu, M. R., et al., NEUROINFORMATICS (2014), doi:10.1007/s12021-014-9238-1).

Recent classification studies incorporating brain measures have shown comparable results to the initial classification and further suggest that heterogeneity of clinically relevant ASD subgroups may limit high classification accuracy. Duchesnay et al. found that PET imaging could be used to predict ASD with 88% accuracy in a sample of 26 participants (Duchesnay, E., et al., NEUROIMAGE 57, 1003-1014 (2011)). Murdaugh et al. used the intra-DEF connectivity to predict ASD with 96% accuracy in a sample of 27 participants (Murdaugh, D. L., et al., PLOS ONE 7, (2012). Wang et al., using whole-brain functional connectivity, correctly predicted ASD with 83% accuracy in a sample of 58 participants (Wang, H., et al., PLOS ONE 7, 1-14 (2012)). Jamal et al. used EEG activity during task switching to predict ASD with 95% accuracy in a sample of 24 participants (Jamal, W., et al., J. NEURAL ENG. 11, 046019 (2014)). Using large data consortiums like the Autism Brain Imaging Data Exchange (ABIDE), recent classification studies have developed and tested models using datasets with over 100 participants. Collectively, these large-sample studies demonstrate performance accuracy from 59% to 70% when testing untrained data (Katuwal, G. J., et al., PLOS ONE 11, 1-24 (2016); Abraham, A., et al., NEUROIMAGE (2016), doi:10.1016/j.neuroimage.2016.10.045; Chen, C. P., et al., CLIN. 8, 238-45 (2015); Sabuncu, M. R., et al., NEUROINFORMATICS (2014), doi:10.1007/s12021-014-9238-1; Katuwal, G. J., et al., ANNUAL INTERNATIONAL CONFERENCE OF THE IEEE ENGINEERING IN MEDICINE AND BIOLOGY SOCIETY 4270-4273 (2015), doi: 10.1109/EMBC.2015.7319338). The data of Example 1 highlights the importance of considering heterogeneity for such tests.

Extension of Prior Machine Learning Studies

Individual Classification Results and their Relation to Subgroups

The RF approach of Example 1 extends prior studies by identifying putative subgroups from a validated ASD classification model. Specifically, three ASD and four control putative subgroups, with a fifth group of isolated subjects, were identified. To further characterize these subgroups, it was determined whether subgroups were stratified via classification accuracy. Because of the extremely stringent inclusion criteria of Example 1, it is highly likely that all ASD subjects indeed have an ASD, therefore ASD subgroups that contain misclassified individuals may represent clinically important subgroups that the initial RF model failed to capture. Control subgroups that contain misclassified individuals may represent subgroups that the initial RF model confused for ASD individuals. The largest subgroup for ASD and the largest and smallest subgroup for controls were significantly more accurate than chance. Other ASD and control subgroups were not, and the distinction in classification accuracy may reflect the heterogeneity within the disorder. In an earlier study, ASD participants were sub-grouped on the basis of symptom severity, verbal IQ, and age, which caused classification rates to increase by as much as 10% (Katuwal, G. J., et al., PLOS ONE 11, 1-24 (2016)). On the other hand, the fact that control subgroups also showed misclassification suggests that variation in such skills may represent the existence of broad cognitive subgroups that are independent of diagnosis, whose variation may impact the presentation of ASD symptoms (Constantino, et al., LANCET. NEUROL. 15, 279-291 (2016)). Prior work by Fair et al. has shown similar heterogeneity in both TD and ADHD children; as with Katuwal, taking into account this heterogeneity improved diagnostic accuracy (Fair, D., et al., FRONT. SYST. NEUROSCI. 6, 80 (2012)).

ASD Subgroups are not Associated with Variance in Symptom Severity

It is controversial whether clinical subgroups even exist in ASD. Recently, it has been suggested that ASD represents the tail end of a continuous distribution of social abilities. According to these theories, categorically distinct subtypes are either artificial constructs (Volkmar, F. R. et al., LANCET. NEUROL. 15, 237-238 (2016)) or unknown (Constantino, et al., LANCET. NEUROL. 15, 279-291 (2016)). Categorically distinct subtypes may be difficult to discover due to the heterogeneity present within the typical population (Fair, D., et al., FRONT. SYST. NEUROSCI. 6, 80 (2012)) as well as the heterogeneity in genetic causes of ASD (Constantino, et al., LANCET. NEUROL. 15, 279-291 (2016)). According to Constantino et al., such genetic subtypes may interact with the environment of the individual, leading to varying manifestations of ASD. Findings that the trajectories of adaptive functioning and autism symptom severity are distinct from one another (Chen, S.-F., et al. PSYCHOL. MED. 1-14 (2016), doi:10.1017/S0033291715002238; Szatmari, P., et al., JAMA PSYCHIATRY 72, 276-83 (2015)) further suggest a dissociation between adaptive functioning and symptom burden.

Therefore, the subgroups identified in Example 1 may reflect the variation in autism symptom severity or in cognitive mechanisms that may impact ASD profiles, independent of severity. To test this hypothesis, it was examined whether the ASD subgroups identified in Example 1 varied by autism symptom severity, as measured by the SRS 96 and the ADOS (Supplemental Analysis 3, Example 2). It was found that the subgroups did not differ on the SRS or the ADOS, suggesting that autism symptom severity was similar across the three subgroups, despite differences in classification accuracy. Because the ASD diagnosis of the participants is likely to be accurate, it is possible that the variation between these three subgroups reflects typical variation in cognitive mechanisms, which may be independent of autism symptom severity but influence ASD presentation (Chen, S.-F., et al. PSYCHOL. MED. 1-14 (2016), doi: 10.1017/50033291715002238; Szatmari, P., et al., JAMA PSYCHIATRY 72, 276-83 (2015)). Identification of such subgroups may be critical for the development of personalized treatment approaches in future studies and has the potential for improving ASD diagnosis and long term outcomes (Constantino, et al., LANCET. NEUROL. 15, 279-291 (2016)). Future studies could better characterize putatively identified subgroups by examining how subgroups may differ on measures of adaptive functioning, or examining whether the subgroups may be characterized by a set of measured ASD symptoms. Critically, future studies could also seek to assess the stability of identified subgroups using longitudinal data.

Describe Identified Subgroups

To further characterize the identified subgroups, differences in the subgroups on the tasks incorporated into the model were examined. With such an analysis, the results can be compared to prior research that has identified subgroups in independent datasets using similar tasks (Fair, D., et al., FRONT. SYST. NEUROSCI. 6, 80 (2012)). Replication of similar subgroups would suggests these subgroups may be meaningful. However, because the data from these tasks were used to construct the model, an independent set of measures may be necessary to establish the validity of the identified subgroups. Therefore, differences in functional brain organization in a subset of participants was also examined, to see whether differences in functional brain organization between the subgroups reflects the effect of an ASD diagnosis on functional brain organization.

Differences in Behavior and how that Compares to Previous Literature

Due to fragmentation and limited sample size, variation in task performance was examined between the three ASD subgroups and between the largest three control subgroups only. Subgroup differences were largely similar, independent of clinical diagnosis. Per sample, the largest subgroups performed best on CPT and stop tasks, and worst on face processing tasks. The second largest subgroups had the smallest spatial span and were slower but more accurate on the face processing tasks. The third largest subgroups had the largest spatial span and were faster, but less accurate, on the face processing tasks. The distinctions between these subgroups are consistent with prior research, which characterized heterogeneity in typical and ADHD samples and found multiple subgroups characterized by either a small spatial span, slow RT, and high information processing, or high spatial span, fast RT and low information processing (Fair, D., et al., FRONT. SYST. NEUROSCI. 6, 80 (2012)). Taken together, these findings suggest that clinical heterogeneity may emerge from normal variation in cognitive profiles, and are consistent with a recent study showing that clinical heterogeneity within ASD may be driven by normative development (van der Meer, J. M. J., et al., J. ATTEN. DISORD. 1087054714533194 (2014)). The various findings of Example 1 extend the prior findings to ASD and establishes a predictive model, which provides some clinical validity to the identified subgroups.

The finding that the differences between subgroups were similar in both ASD and TD samples may appear inconsistent with prior studies that show an effect of ASD on the relationship between cognitive measures and task performance (Joseph, R. M., et al., NEUROPSYCHOLOGIA 43, 1400-1411 (2005); Tye, C., et al., EUR. CHILD ADOLESC. PSYCHIATRY 7, e1210-5 (2014); Barton, J. J. S., et al., BRAIN 127, 1706-1716 (2004); Hefter, R. L., et al., NEUROLOGY 65, 1620-1625 (2005)). However, differences in diagnostic criteria may explain some of the apparent contradiction here. The study provided herein in Example 1 used a team of experts to confirm ASD diagnosis per individual, whereas these prior studies often used only a DSM diagnosis plus one or two instruments that assess autism symptom severity (e.g. the ADOS and/or ADIR). The inconsistency in findings may be interpreted as further evidence of heterogeneity within ASD. Differences in cognitive profiles across individuals with ASD could explain the variation in attention, working memory, and face processing. In addition, prior work suggests that cognitive subtypes within ASD may be similar to cognitive subtypes found in typical populations (Rommelse, N. N. J., et al., CLIN. PSYCHOL. SCI. 4, 957-970 (2016)).

Differences in fMRI Data and Validation of Subgroups how that Compares to Previous Literature To provide further validation of the subgroups, it was examined whether significant differences in the functional organization of the brain between subgroups overlapped with significant effects of ASD on functional brain organization. Since this data was never used in the RF model, variation that overlaps with differences between ASD and typical children may reflect clinically or etiologically important distinctions between subgroups. Because differences in symptom severity between subgroups were not observed, the findings above are more likely to reflect typical variation in neural mechanisms underlying cognitive performance, as opposed to manifestations of ASD symptoms.

Differences between children with and without ASD are consistent with prior studies but also show some novel findings. Children with an ASD have shown altered visual system responses to stacks of oriented lines (Vandenbroucke, M. W., et al., BRAIN 131, 1013-1024 (2008)), and at rest they've exhibited altered DEF functional connectivity (Monk, C. S., et al., NEUROIMAGE 47, 764-772 (2009)), but not altered cingulo-operuclar connectivity (Redcay, E., et al., FRONT. HUM. NEUROSCI. 7, 573 (2013)). Between system differences have been less studied in ASD, however, subcortical cortical connectivity has been shown to be altered (Di Martino, A., et al., MOL. PSYCHIATRY 19, 659-67 (2014); Cerliani, L., et al., JAMA PSYCHIATRY 72, 1-11 (2015)) as well as the dorsal attention network organization (Ray, S., et al., HUM. BRAIN MAPP. (2014), doi:10.1002/hbm.22603), which may be consistent with altered connections between subcortical and dorsal attention networks. However, differences between the DEF and visual, somatomotor, and cingulo-opercular systems have not been documented. The differences found between somatomotor and DEF may be consistent with findings of altered motor system function in ASD (Nebel, M. B., et al., HUM. BRAIN MAPP. 35, 567-580 (2014)), while differences between DEF and cingulo-opercular systems may be consistent with altered rich-club organization (Ray, S., et al., HUM. BRAIN MAPP. (2014), doi:10.1002/hbm.22603).

The ANOVA chi-squared analysis may be underpowered (Eggebrecht, A. T., et al., CEREB. CORTEX 1-12 (2017), doi: 10.1093/cercor/bhw403) and, though enticing, may not be definitive. Nevertheless, the subgroup chi-squared ANOVAs hint that the identified subgroups may reflect differences in both mechanisms relevant to an ASD diagnosis, and mechanisms that reflect variation across the subgroups. Four of the seven connectivity modules significantly affected by an ASD diagnosis showed variation in the ANOVA analysis: connectivity within the DEF; connectivity between the DEF and cingulo-opercular systems, between the DEF and somatomotor systems, and between the dorsal attention and subcortical systems. It was also found that significant variation in the ANOVA chi-squared analysis from the ASD and typical comparisons. Like with behavioral measures in children with and without ADHD, it can be possible that variation within the ASD subgroups identified in Example 1 may actually be "nested" within the normal variation found in brain networks across typical children (Constantino, et al., LANCET. NEUROL. 15, 279-291 (2016); Fair, D., et al., FRONT. SYST. NEUROSCI. 6, 80 (2012); Szatmari, P., et al., JAMA PSYCHIATRY 72, 276-83 (2015)).

Figure 15:
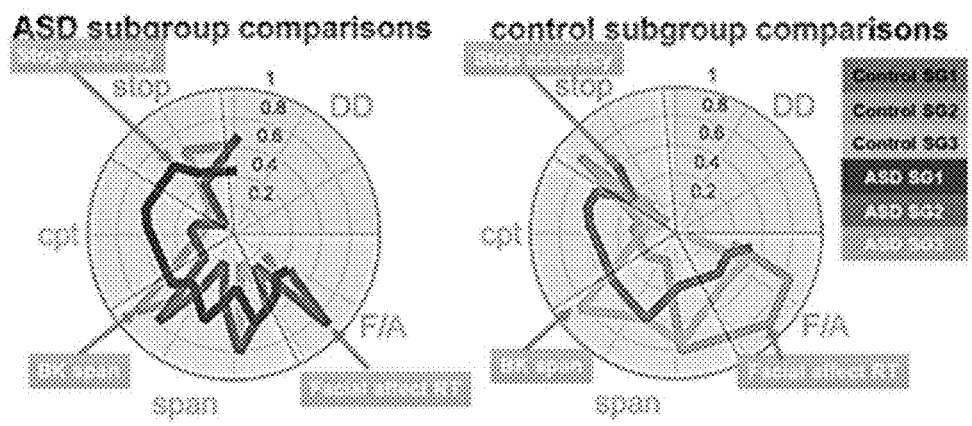

The correspondence between the subgroups and the connectivity profiles are intriguing, and hint that the first ASD subgroup may have altered visual processing mechanisms, the third ASD subgroup may have altered attention mechanisms, and the second ASD subgroup may have both. Speculatively, the first ASD subgroup shows the best ASD performance on both stop and CPT tasks, just as individuals in the first control subgroup performs better than the other control subgroups. Inter-system connectivity between the default mode and task control and attention systems (i.e. CIP and DOA) are control-like in the first ASD subgroup, as well as connectivity between attention and motor systems. As discussed extensively in the introduction, such variation can be consistent with the literature and may reflect typical heterogeneity variability related to the presentation of ASD. The third ASD subgroup shows the worst performance on facial and affect tasks of the three ASD subgroups; the first control group performs worse on the same tasks compared to the other control subgroups (FIG. 15; right). Such tasks would involve visual processing, and the chi-squared comparison reveals that the third ASD and first control subgroups have similar visual system connectivity. Variation in facial task performance may be implicated in some children with autism (Tanaka, J. W., et al., J. CHILD PSYCHOL. PSYCHIATRY 53, 1259-1267 (2012)), but not others (Barton, J. J. S., et al., BRAIN 127, 1706-1716 (2004)). It will be interesting to see whether future studies identify similar variation in system-level connectivity between ASD subgroups, and whether these groups are stable over time. In addition, future studies with larger sample sizes may be able to uncover additional or more refined sub-populations within the disorder.

Effects of Demographics on RF Model Performance and Subgroup Affiliation

Due to the age and gender differences between the ASD and TD samples, it may be desirable to test whether the typical variation affecting ASD subgroups may reflect differences in demographic variables. Six supplemental analyses (see: Supplemental Materials, Example 2) were further conducted to address this question. The analyses detailed extensively in Supplemental Materials (Example 2) are alluded to here. Specifically, the effect of age and gender on the behavioral measures was evaluated (Supplemental Analysis 1), the RF classification on behavioral measures when controlling for age and gender was performed (Supplemental Analysis 2), the effect of ASD subgroup on ADOS symptom scores was examined (Supplemental Analysis 3), whether subgroup affiliation affected age, IQ, or gender was tested (Supplemental Analyses 4 and 5), and how much each behavioral measure improved RF classification was measured (Supplemental Analysis 6).

Figure 19:
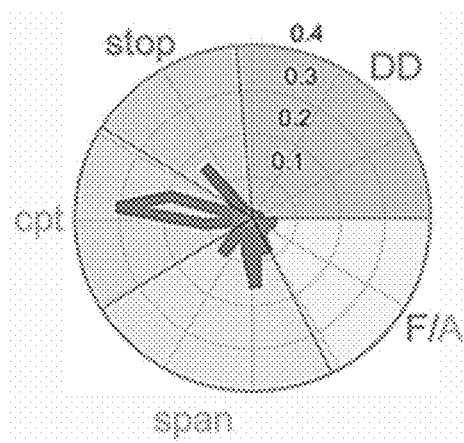
Figure 26:
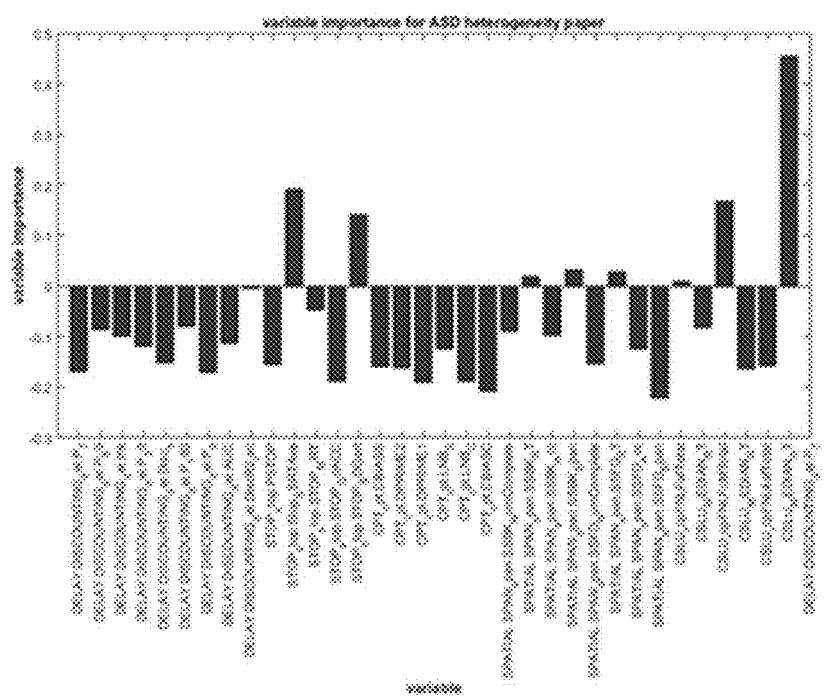

The results from the supplemental RF were concerning, and hinted that controlling for age and gender may have, in fact, biased the analysis in unintended ways. There is some literature (Miller, G. A., et al., J. ABNORM. PSYCHOL. 110, 40-48 (2001)) that suggests such biases may occur when the differences in groups might differ by the controlling variables, but the features important for classification (i.e. in this case the behavioral measures) are not associated with those variables (i.e., here, age or gender). When the association between age/gender and behavioral measures was compared (Supplemental Analysis 1; FIG. 19) to the behavioral measure importance (Supplemental Analysis 6; FIG. 26), only a few variables were associated with age or gender; the most important behavioral features showed no association with either demographic variable. Based on the RF analysis, several sub-groups were found to differ primarily by age and gender. Such findings were minimal in the main analysis. The findings provide important context for the primary findings, and highlight the importance of first examining the relationship between nuisance variables and input features. If no associations between input features and regressors are found, but regressors are associated with the outcome variable, then such regression may bias subsequent models in unintended ways. Similar concerns have been found when using parametric tests like analysis of covariance (ANCOVA) in psychiatric research (Miller, G. A., et al., J. ABNORM. PSYCHOL. 110, 40-48 (2001)). Nonetheless, several considerations arise from these supplementary analyses.

Figure 21:
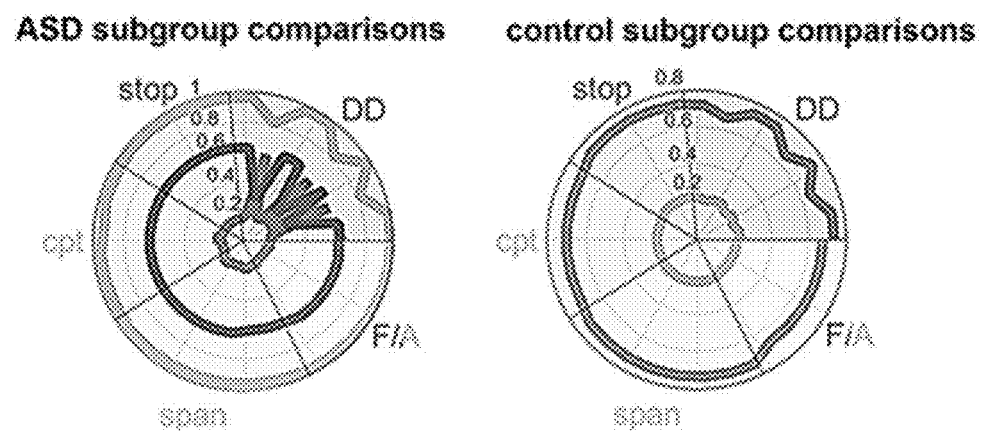

When controlling for age and gender, the supplemental RF (Supplemental Analysis 2, Example 2) showed a reduction in classification accuracy from 73 to 62 percent (FIG. 20A). Nevertheless, the RF model remained significantly above chance for both ASD (64 percent) and TD (60 percent) individuals. Notably, the drop in model performance was driven entirely by the TD group, where performance dropped over 20 percent. Inspection of the subgroups shows that the second TD subgroup was more similar to the ASD subgroups; accuracy for the second TD subgroup was almost zero, suggesting that they were all being classified with ASD (FIG. 20D), and therefore ASD classification may be driven by typical heterogeneity. Such an interpretation can be consistent with the findings from the original RF of Example 1. Additionally, there was little evidence suggesting that ASD subgroups varied by either SRS (FIG. 20E and FIG. 14E) or ADOS (FIGS. 22A and 22B; Supplemental Analysis 3) measures, which further indicates that ASD subgroups vary by typical heterogeneity and not autism symptom severity. However, it may be unclear whether typical heterogeneity reflects demographic variables like age and gender or more cognitive variables like IQ or general task performance (FIG. 21). Therefore, further analyses investigated what aspects of typical heterogeneity affected subgroup affiliation.

Figure 23A:
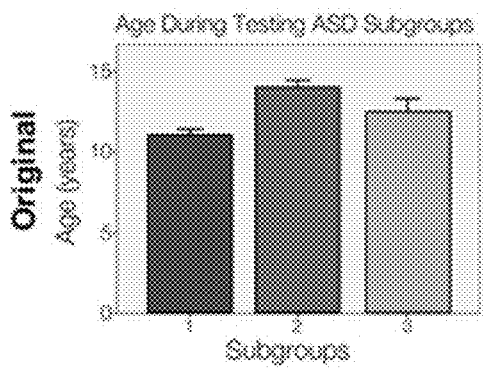
FIGS. 23A to 23D illustrate bar plots of age for original (top) and supplemental (bottom) subgroups. Plots are split by ASD (left) and TD (right) subgroups. Error bars reflect one standard error of the mean. Subgroups are color-coded by their affiliated colors.
Figure 23B:
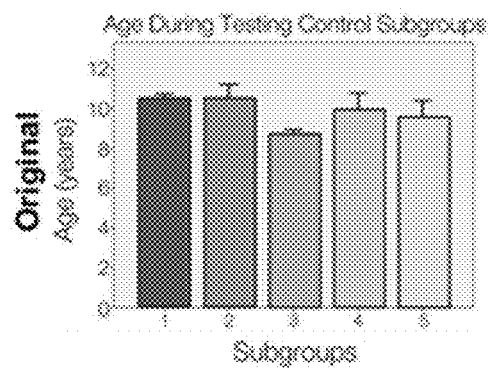
Figure 23C:
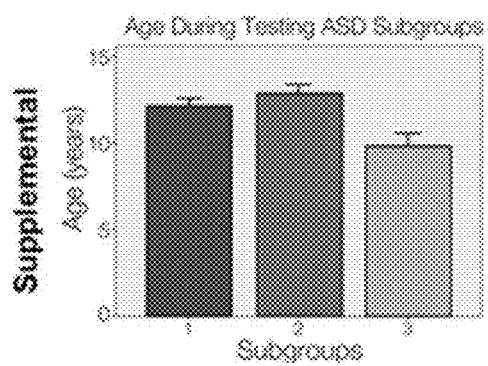
Figure 23D:
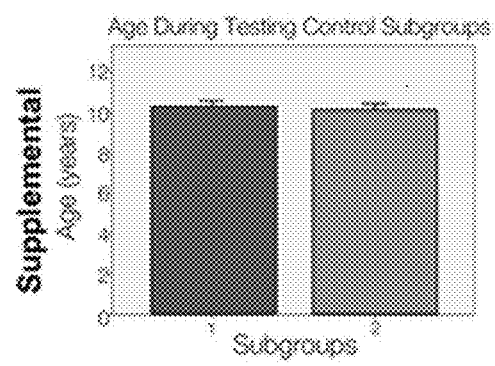
Figure 24A:
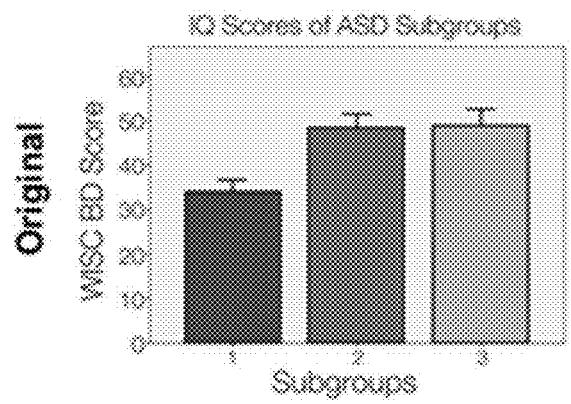
FIGS. 24A to 24D illustrate bar plots of IQ, as measured by block design scaled scores for original (top) and supplemental (bottom) subgroups. Plots are split by ASD (left) and TD (right) subgroups. Error bars reflect one standard error of the mean. Subgroups are color-coded by their affiliated colors (see.
Figure 24B:
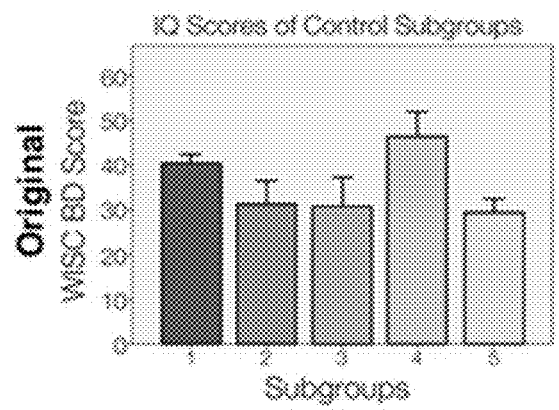
Figure 24C:
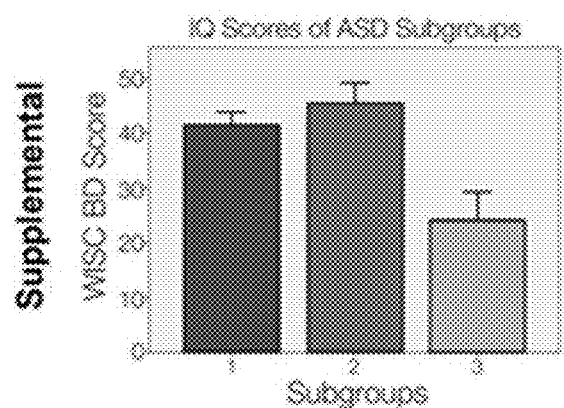
Figure 24D:
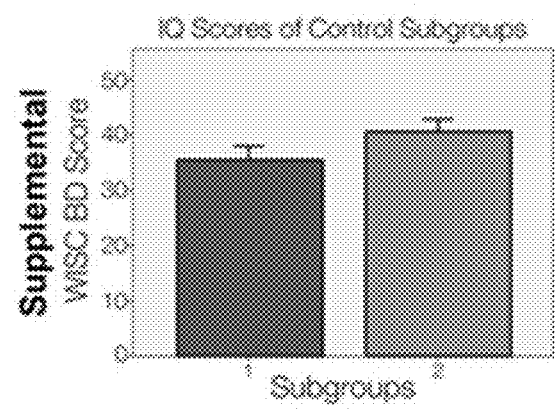
Figure 25A:
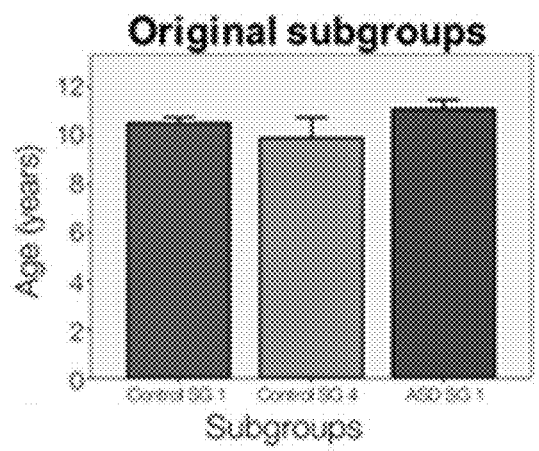
FIGS. 25A to 25D illustrate age (top) and IQ (bottom) bar plots for accurately classified original (left) and supplemental (bottom) subgroups. Error bars reflect one standard error of the mean. Subgroups are color-coded by their affiliated colors (see.
Figure 25B:
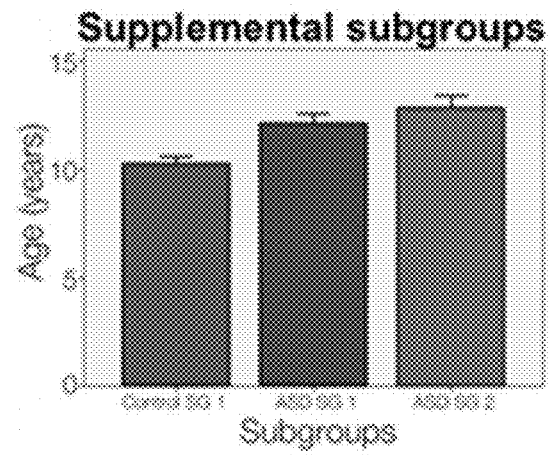
Figure 25C:
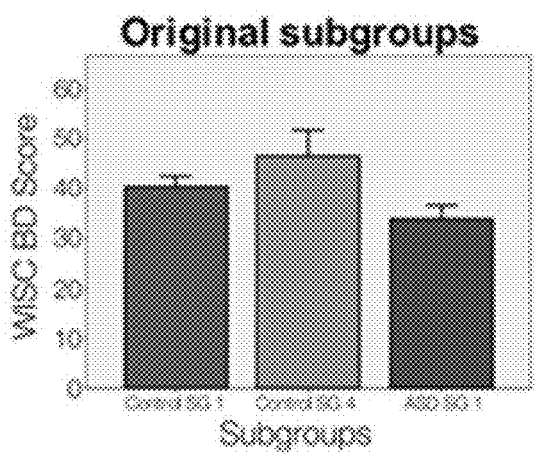
Figure 25D:
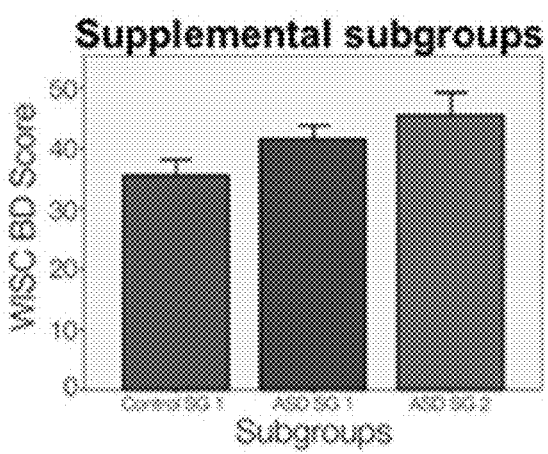

The original RF model may be driven by cognitive profile, while the supplemental RF model may be driven more by demographics Surprisingly, as noted above, the supplemental RF analysis identified subgroups that varied more by age and gender than the original RF (Supplemental Analysis 4, Example 2). When variation between control subgroups was examined, it was determined that the supplemental RF subgroups (FIGS. 23D and 24D) were split by gender, while the original subgroups showed no demographic differences (FIGS. 24B and 24D). The ASD supplemental subgroups varied by age (FIG. 23C), gender, and IQ (FIG. 24D), while the ASD original subgroups varied by age (FIG. 23A) and IQ (FIG. 24A). The variation in age and IQ differed between the supplemental and original analysis. The most accurately classified ASD subgroup in the original analysis of Example 1 was closest in terms of age and IQ to the control subgroups, while the least accurately classified ASD subgroup in the supplemental analysis was most similar to the control subgroups. Because such demographic differences between accurately classified subgroups may explain the RF classification, it was determined whether accurately classified ASD subgroups differed from accurately classified control subgroups. Since gender did not vary in the original analysis between ASD subgroups and between control subgroups, age and IQ variables were used. It was found that age and IQ varied more in the supplemental (Example 2) than in the original analysis (Example 1), however, IQ was numerically lower in the original ASD subgroup when compared to the control subgroups. Taken together, the findings suggest that the original RF was driven by variation in typical cognitive profiles, whereas the supplemental RF may be affected by variation in gender and age.

Example 2: Identifying ASD Subgroups Using a Functional Random Forest Model

Introduction

The results in Example 1 suggest that ASD subgrouping may vary by typical heterogeneity. Due to the differences in gender and age between the ASD and typical samples, Example 2 examines the effects of demographic variables on the RF classification and subgroup identification, and whether the groups varied by clinical assessments. To examine these effects, five supplemental analyses were conducted, in which 1) the association between task performance and age/gender was evaluated, 2) whether an RF using age and gender regressed task data accurately classifies ASD from TDs was tested, 3) whether ADOS symptom severity varied between ASD subgroups was measured, 4) whether ASD and TD subgroups varied by demographic was determined, and 5) whether accurately classified subgroups differed by demographics was tested. Additionally, Example 2 includes an evaluation of which features were considered most important within the model (Supplemental Analysis 6).

Supplemental Analysis 1: Evaluation of Age and Gender on Input Features

Introduction

In the sample of Example 1, ASD outcomes varied by age and gender, but it was possible that, within the specific sample, such variation may not be associated with performance on the tasks measured. Therefore, it was examined whether age and gender were associated with task measures using linear and logistic regression. If age and gender are associated with specific measures, then such measures may not be specific to clinical outcomes, and age and gender could drive RF classification. If age and gender are unrelated to specific measures, then such measures may be specific to clinical outcomes, and it can be less likely that age and gender drive RF classification.

Methods

In order to evaluate whether age and gender may have driven the results in Example 1, a linear regression analysis was performed for age and a logistic regression analysis was performed for gender against the 34 features used as predictors in the random forest (RF) algorithm. All data across ASDs and TDs were used in the regression analysis, in order to assess how much effects of ASD on gender and age may have influenced the primary findings in Example 1. False Discovery Rate (FDR) with a q of 0.05 was used to correct for multiple comparisons. The effect size for each regression was assessed using R-squared values as the measure of effect size. If R-squared values are low for all features, it would suggest that age and gender are not driving factors in the analysis.

Results

Figure 22A:
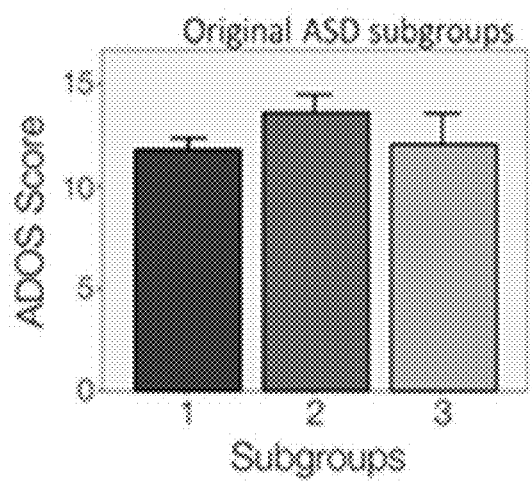
FIGS. 22A to 22B illustrates bar plot of ADOS summed scaled scores for ASD subgroups. Error bars reflect one standard error of the mean. Subgroups are color-coded by their affiliated colors.
Figure 22B:
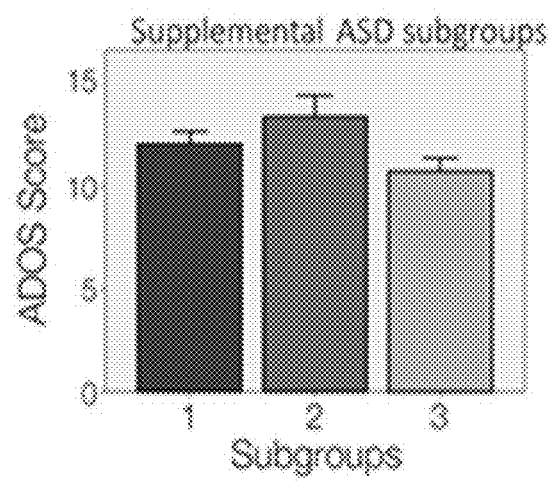

FIG. 19 shows the relationships observed between age (FIG. 19; blue), gender (FIG. 19; red), and task measures. No measure was significantly associated with gender, after correction for multiple comparisons ($R2<0.045$, $p>0.169$). However, eight features were significantly correlated with age (significant p threshold=0.011): CPT dprime1 ($R2=0.308$, $p<0.001$), CPT dprime2 ($R2=0.192$, $p<0.001$), CPT natural log of bias ($R2=0.105$, $p=0.001$), spatial span forward RT ($R2=0.158$, $p<0.001$), spatial span backward RT ($R2=0.105$, $p=0.001$), spatial span forward span ($R2=0.086$, $p=0.002$), spatial span forward number completed ($R2=0.077$, $p=0.004$), and accuracy on stop go trials ($R2=0.165$, $p<0.001$). Despite this relationship, measures that show insignificant correlations with age, such as stop signal RT ($R2=0.022$, $p=0.136$), standard deviation of stop go trial RT ($R2=0.026$, $p=0.099$), facial affect accuracy ($R2=0.045$, $p=0.033$), and auditory affect RT ($R2=0.039$, $p=0.049$), strongly characterized the differences between subgroups (FIG. 15) and between diagnostic samples (FIGS. 22A and 22B). This analysis suggests that gender and age may have had minimal influence on the predictive features despite the differences between ASD and TDs.

Discussion

Ultimately, it was found that the relationship between age and predictive features varied by task. Measures from CPT and spatial span tasks were associated with age, whereas facial affect, delayed discounting, and stop tasks were not. Stop and facial affect tasks contained measures that were considered extremely important by the RF (see: supplemental analysis 6). Taken together, these findings suggest that age and gender are less likely to be driving any RF classification. Nevertheless, it can certainly be possible that combinations of variables may be associated with age and gender. Therefore, examining the effects of age and gender on RF classification and subgroup identification can help determine which explanation can be more likely.

Supplemental Analysis 2: RF Classification when Controlling for Age and Gender

Introduction

Supplemental analysis 1 suggested that RF classification may not be affected by associations between task performance and age or gender, but it is far from conclusive. This question can be further addressed directly by testing whether RF classification accuracy can be affected when controlling for age and gender. If RF accuracy can be unaffected, then it is more likely that age and gender did not affect RF classification performance. Unfortunately, due to the strong association between age, gender, and clinical outcome, reductions in RF classification performance should be expected, even if age and gender are weakly related to the task performance measures. However, if RF model performance falls below chance, it can be more likely that RF classification was driven by demographics. If RF model performance can be above chance, subgroups will be identified via Infomap and examined further to explore what features may drive RF classification in this supplemental analysis.

Methods

Age and gender were controlled for via linear and logistic regression separately. Per feature, the residuals from linear regression of the feature against age were calculated, and the residuals were input into a logistic regression against age, where new residuals were calculated. This procedure resulted in 34 residual features, controlling for both age and gender, which were used as input for the RF algorithm (see the main manuscript for details). It can be important to interpret these results cautiously. Because gender and age are different between ASD and TDs, if gender and age are not related to the predictors, then this regression procedure may add variance into the input data without removing any bias. In other words, because of the gender and age confounds, reduced classifier performance can be expected when performing regression.

Results

After controlling for age and gender, random forest successfully classified participants without an ASD from participants with an ASD RF model accuracy is shown in FIG. 20A. Applying the RF algorithm on behavioral data from 7 different tasks (34 variables) achieved an overall classification accuracy of 62% (M=0.623, SD=0.063) and an independent sample t-test revealed that the RF model was significantly more accurate than the permutation accuracy measure of 50% [M=0.504, SD=0.077; t(1998)=37.83, p<0.001]. The RF model had a sensitivity of 64% (M=0.647, SD=0.123) when classifying ASD participants, the ability to correctly identify true positives, and an independent sample t-test revealed that the model's sensitivity was marginally, albeit significantly, higher compared to the permutation sensitivity of 47%. [M=0.467, SD=0.137; t(1998)=30.98, p<0.001]. The RF model also had a specificity of 60% (M=0.603, SD=0.106) when classifying TD participants, the ability to correctly identify true negatives, and an independent sample t-test revealed that this was significantly more accurate compared to the permutation specificity of 53%. [M=0.534, SD=0.123; t(1998)=13.55, p<0.001]. After controlling for age and gender, the RF model separates TDs and ASDs equally. However, the proximity matrix notes strong separation between the groups (FIG. 20B). Because few predictive features were significantly related to age and gender, but age and gender were significantly different between the cohorts, the observed loss of accuracy may reflect increased noise in the residuals as opposed to a removal of age and gender confounds.

Proximity Matrices from Random Forest Model Suggest Three Subgroups Each for ASD and Two for Control Cohorts The community detection algorithm identified three putative ASD subgroups and two putative TD subgroups (FIG. 20B). For children with an ASD diagnosis, the largest subgroup comprised 27 individuals, while the other two subgroups numbered 15 and 4 children respectively. One child was not part of any community and left out of remaining analyses. For children without an ASD diagnosis, the largest subgroup comprised 31 individuals, the second group numbered 27 individuals. To characterize these subgroups, variance of accuracy of classification between subgroups was examined, and then variation in the task measures between the subgroups was examined.

ASD Subgroups Differed in Terms of Classification Accuracy

A one-way between participants ANOVA was conducted to compare classification accuracy between the 3 ASD subgroups identified by community detection (FIG. 20C). There was a significant effect of subgroups on classification accuracy [F(2,43)=12.212, p<0.001]. Post-hoc comparisons using an independent-sample t-test indicated that the classification accuracy for Subgroup 3 (M=0.005, SD=0.007) was significantly worse than Subgroup 1 [M=0.706, SD=0.297; t(27)=−4.645, p<0.001] and Subgroup 2 [M=0.678, SD=0.237; t(17)=−5.558, p<0.001], while Subgroups 1 and 2 were not significantly different from one another [t(40)=0.315, p=0.754].

An independent sample t-test was conducted to see if subgroup classification accuracy significantly differed from chance (0.5) using a Bonferroni adjusted alpha level of 0.017 per test (0.05/3). Subgroup 1 [t(26)=3.604, p=0.001] and Subgroup 2 [t(14)=2.908, p=0.012] were both significantly better at classification than chance, while Subgroup 3 was significantly worse than chance [t(3)=−146.247, p<0.001].

TD Subgroups Differed in Terms of Classification Accuracy

Supplemental FIG. 20D shows the accuracy for TD subgroups. An independent samples t-test was conducted to compare classification accuracy between the two TD subgroups identified by community detection which revealed that Subgroup 1 (M=0.870, SD=0.286) had significantly higher classification accuracy compared to Subgroup 2[M=0.287, SD=0.240; t(56)=8.339, p<0.001].

An independent sample t-test was conducted to see if subgroup classification accuracy significantly differed from chance (0.5) using the Bonferroni adjusted alpha level of 0.025 per test (0.05/2). Participants in Subgroups 1[t(30)= 7.206, p<0.001] were correctly classified as TDs significantly more than chance, while participants in Subgroup 2 [t(26)=−0.4.611, p<0.001] were incorrectly classified as ASD more than chance.

Similar Cognitive Profiles were Identified with ASD and within TD Subgroups

To test whether ASD subgroups may reflect quantitative variation in autism symptom severity, it was examined whether identified ASD subgroups varied by Social Responsiveness Scale (SRS; FIG. 20E). A one-way ANOVA revealed no significant differences between the subgroups on SRS (F(2,44)=0.012, p=0.988), suggesting that ASD subgroups may have had similar autism severity but varied in other ways.

Because normal variation in cognitive profiles may affect the manifestation of a developmental disorder (Fair, 2012), it was then examined the variation in task performance for ASD (FIG. 21; left) and TD (FIG. 21; right) subgroups. For both sets of subgroups, all measures were significantly different. For both ASD and TD subgroups, similar cognitive profiles were observed and separated by overall task performance. The largest subgroup performed best across all tasks. The second largest subgroup performed worst across all tasks. For ASD, the third subgroup was characterized by varying performance in the middle.

Discussion

RF Classification can be Reduced when Controlling for Age and Gender, but Still Greater than Chance Compared to the original analysis (FIG. 14A), accuracy for the supplemental RF model decreased approximately 11 percent. The reduction in overall accuracy can be driven entirely by a 20 percent reduction in specificity, whereas sensitivity was unchanged. Although the reduction in model performance is large, it is difficult to dissociate whether the supplemental or original analysis should be the preferred analysis. Nevertheless, both RFs show over 60% accuracy and perform significantly better than the null models. Therefore, subgroups were identified and subgroup similarity and model performance per subgroup were examined.

Two ASD Subgroups Appear More Similar to the Second TD Subgroup than the Third ASD Subgroup In the supplemental RF, model performance varied dramatically by subgroup. The third ASD and second TD subgroups could not be accurately classified, and visual inspection of the similarity matrix (also referred to as a "proximity matrix") reveals almost no similarity between the two TD subgroups, or between the ASD subgroups. In fact, the second TD subgroup was more similar to the first two ASD subgroups than to the other TD group. The supplemental RF subgroups are substantially different from the original RF subgroups, so further examinations of how these subgroups may vary by demographics (see: Supplemental Analysis 4 and 5), and cognitive profile, were performed.

Subgroups Differed by Overall Performance but not Symptom Severity

Both ASD and TD subgroups varied by cognitive profile. The third ASD subgroup and first TD subgroup showed high performance across the variables, whereas the second TD and first two ASD subgroups showed low performance. These cognitive profiles are consistent with the model performance; the second TD subgroup and third ASD subgroups could not be accurately classified. Furthermore, autism symptom severity, as measured by the social responsiveness scale, did not vary between ASD subgroups, which suggests that autism symptom severity was similar across the three ASD subgroups. Taken together, these results suggest that the RF model can be identifying subgroups by typical heterogeneity rather than ASD symptom severity, which can be also consistent with the findings from the original RF.

Supplemental Analysis 3: Effect of Subgroup on ADOS Scores

Introduction

The social responsiveness scale (SRS), while a quantitative estimate of autism symptom severity, may fail to capture aspects of autism traits that can be captured through other instruments. In order to further test whether ASD subgroups varied in autism symptom severity measures, variance in autism symptom severity, as measured by the Autism Diagnostic Observation Schedule (ADOS), between ASD subgroups was determined. The ADOS measures observed child behavior as the child interacts with a trained clinician, while the SRS is a parental report of symptoms over an approximate six month period. Therefore the ADOS represents a very different type of measure than the SRS. If no differences in ADOS symptom severity can be observed, it is more likely that the ASD subgroups reflect typical heterogeneity more than autism symptom severity.

Methods

A one-way ANOVA was used to examine the effect of subgroup on ADOS sum scaled scores, where subgroup was modeled as a factor and the ADOS sum scaled scores were the dependent variable. This analysis was performed for the subgroups identified by both the original (FIG. 22A), and supplemental (FIG. 22B) analyses.

Results

ADOS symptoms for the original (FIG. 22A) and supplemental (FIG. 22B) subgroups are shown in FIGS. 22A and 22B. For the original analysis, no significant effects of subgroup were observed ($F(2,46)=1.122$, $p=0.335$), and the largest numerical difference was observed between the first (M=11.8 SD=2.79) and second (M=13.54 SD=3.52) subgroups (cohen's d=0.53). For the supplemental analysis, no significant effects of subgroup were observed ($F(2,45)=1.256$, $p=0.295$). However, large numerical effects were observed comparing the third subgroup (M=10.75 SD=1.258) to the first (M=12.07 SD=3.234; cohen's d=0.56) and second (M=13.4 SD=3.924; cohen's d=0.9) subgroups. The large effect size in the supplemental results may have been affected by demographics, particularly differences in gender.

ASD Original Subgroups Show No Significant Variation in ADOS Symptom

Both the original and supplemental RF subgroups showed similar effects; the effect of subgroup on autism symptom severity for either model was found. Coupled with the prior findings, it is likely that the subgroups identified by both the supplemental and original RFs reflect variation in typical heterogeneity rather than ASD severity. However, typical heterogeneity could reflect variation in demographics, cognitive profile or both. Having already compared cognitive profiles (FIG. 15 and FIG. 21), it was investigated whether demographics such as age, and gender varied within the original and supplemental RF subgroups.

Supplemental Analysis 4: Comparison of Demographics Between ASD Subgroups and Between TD Subgroups Introduction Variation in typical heterogeneity could be explained either by cognitive or demographic factors, such as age and gender. Therefore, it was examined whether demographic traits like age and gender, or cognitive traits like intelligence, vary between the ASD and TD subgroups. Variation in such demographic factors and not autism symptom severity would indicate that RFs were sensitive to demographic factors. Comparing demographic differences between the original and supplemental RF subgroups may indicate how age and gender regression affected subgroup affiliation.

Methods

In order to examine factors that may drive subgroup identification, it was examined whether ASD and TD subgroups showed significant variation in gender, age, or intelligence as measured by the WISC-IV block design scaled score. Age per individual was calculated as the mean age across all behavioral tasks the individual participated in. The MRI ages were excluded because those would not factor into the RF model itself, for MRI data were analyzed independently from the RF model. As with ADOS symptom scores, separate one-way ANOVAs per age and IQ measure were used to test the effect of subgroup on ASD and TD subgroups. For gender, a chi-squared analysis was used. Both supplemental and original RF subgroups were examined.

Results

Therefore, it was examined whether the ASD and TD subgroups varied by age (FIGS. 23A to 23D), gender and IQ (FIGS. 24A to 24D). For the TD original subgroups, there was no significant variation in age (FIG. 23B; $F(4,57)=2.09$, $p=0.095$), IQ (FIG. 24B; $F(4,57)=2.33$, $p=0.068$), or gender ($\chi2(df=4, N=57)=4.979$, $p=0.290$). The supplemental subgroups split into female (first) and male (second) subgroups ($\chi2(df=1, N=57)=58.00$, $p<0.001$) but showed no significant age (FIG. 23D; $t(56)=0.343$, $p=0.733$) or IQ (FIG. 24D; $t(56)=-1.54$, $p=0.129$) differences, suggesting that the supplemental RF may have classified the groups primarily on gender differences.

Both the ASD supplemental and original subgroups varied by age (FIGS. 23A to 23D) and IQ (FIGS. 24A to 24D), but in very different ways. For the original subgroups, the largest (N=25) and best classified subgroup had significantly lower age (FIG. 23A; $F(2,46)=3.39$, $p=0.043$) and IQ (FIG. 24A; $F(2,46)=8.4$, $p=0.001$). For the supplemental subgroups, the smallest (N=4) and worst classified subgroup had significantly lower age (M=9.76, SD=1.59) and IQ (M=24.3, SD=9.95). It is possible that the discrepancy between the original and supplemental results may be driven by differences in gender composition; the supplemental ASD subgroups varied by gender ($\chi2(df=2, N=57)=20.112$, $p=<0.001$), with the smallest subgroup comprising female ASD children, whereas the original ASD subgroups did not vary by gender ($\chi2(df=2, N=57)=0.875$, $p=0.646$).

Discussion

Original ASD Subgroups Vary by Age and IQ

Demographic differences for the original dataset show that age and IQ vary by ASD subgroup, while TD subgroups show no differences in demographics. In particular, the largest and best classified ASD subgroup can be both younger and has a lower IQ than the other two ASD subgroups. Notably, this subgroup can be closest to the mean age and IQ of the TD subgroups. These findings suggest that the ASD subgroup variation reflects typical variation in cognitive profile, age and IQ, but not gender.

Supplemental ASD and TD Subgroups May be Driven by Gender Differences

Demographics differences for the supplemental dataset suggest that TD subgroups were stratified by gender. ASD supplemental subgroups showed significant variation across age, IQ and gender. In particular, the worst classified and smallest subgroup was youngest and had lower IQ. Notably, the poorly classified ASD subgroup shows the greatest demographic similarity to the TD subgroups. TD subgroups were effectively split into male and female subgroups, suggesting that the supplemental RF was driven by gender differences. Given that gender was controlled for, this effect was somewhat surprising. However, the univariate regression approach does not TD for combinations of multiple variables, which may still enable one to dissociate male from female participants. Therefore, it may be unclear whether effects of gender in the supplemental material is artifactual, or represents variation in gender.

Supplemental Analysis 5: Comparison of Demographics Between Accurately Classified Subgroups Introduction Because it may be unclear whether regression produced an RF model that identified artifactual or meaningful subgroups, it was tested whether age and IQ varied between accurately classified ASD and TD subgroups. If accurately classified subgroups in the original RF model do not differ by age or IQ, then it can be unlikely that the original RF model classified participants on the basis of such factors, suggesting that variation in typical cognitive profile may have driven RF classification and subgroup identification. If accurately classified subgroups in the supplemental RF model differ by age or IQ, then it can be likely that the supplemental RF model classified participants by demographics, suggesting that demographic variation may have driven the supplemental results.

Methods

If RF classification accuracy can be driven by variation in demographics, significant differences in age/gender/IQ between the accurately classified subgroups would be expected. Therefore, it was tested whether the RF classification was driven by demographic variables (i.e. age, gender, and IQ) using one-way ANOVAs and chi-squared tests. Subgroups whose accuracy was greater than random chance were modeled in the analyses. As with the above analyses, both the original and supplemental subgroups were examined, to see how controlling for age and gender via regression impact subgroup composition.

Results

Given the uncertainty with the supplemental analysis, it was examined whether the results of either analysis could be explained by age or IQ. If successfully classified ASD and typical subgroups vary by demographics, then such variation could affect the RF model. Therefore, age and IQ were compared using a one-way ANOVA across ASD and TD subgroups that were accurately classified in the original (FIGS. 14C and 14D) and the supplemental (FIGS. 20C and 20D) analyses.

IQ and age for accurately classified supplemental and original subgroups are shown in FIGS. 25A to 25D. For the original analysis, subgroups did not significantly vary by age (FIG. 25A; $F(2,66)=1.37$, $p=0.261$), or IQ (FIG. 25C; $F(2,66)=2.65$, $p=0.078$). However, IQ may be numerically lower in the ASD subgroup (M=34, SD=12.75) than in the first (M=40.5, SD=12.64; cohen's d=0.51) or fourth (M=46.3, SD=9.61; cohen's d=1.1) TD subgroups. For the supplemental analysis, both age (FIG. 25B; $F(2,72)=11.29$, $p<0.001$) and IQ (FIG. 25D; $F(2,72)=3.13$, $p=0.05$) showed significant variation across the subgroups. In particular, the TD subgroup was numerically younger (M=10.3, SD=0.157) and had lower IQ (M=35.6, SD=13.7) than the ASD subgroups.

Discussion

Due to small sample sizes, these tests are interpreted cautiously. Nevertheless, the results here suggest that the RF model in the original analysis does not differentiate between ASD and TD samples by simple age or IQ. In fact, the ASD subgroup closest to the TD subgroups in age shows the highest classification accuracy. IQ shows a numerical difference, suggesting that variation in cognitive profile may have driven the RF. As noted above, subgroups in supplemental appear to be split by gender, but also may vary by both age and IQ. The direction of this variation differs from the original analysis, in that the ASD accurately-classified subgroups are older, more female, have lower IQ, and all of the observed effects are much larger. Taken together with the ADOS and SRS findings, these results suggest that ASD subgroups vary by typical heterogeneity more than autism symptom severity. Notably, the original RF model can be less driven by demographic criteria than the regressed model in the supplemental, particularly age. Given that few task variables are associated with age and gender (see: FIG. 19), it is possible that the supplemental regression may have contaminated the analysis. Therefore, it may be advisable to perform such a regression only when an association can be observed. Additionally, a careful examination of the subgroup demographics can help determine whether demographics affect the accuracy of the model.

Supplemental Analysis 6: Examination of Variable Importance from Features

Introduction

Because associations between input features and demographics varied across tasks and measures, the importance of each feature used in the original RF was evaluated. This analysis provides context for the supplemental analyses above. If features important for classification were associated with age and gender, controlling for age and gender is likely produce a more appropriate model. On the other hand, if features important for classification are unrelated with age and gender, such regression could contaminate the analysis, because age and gender are associated with the clinical outcome in the sample. Additionally, a number of included features are controlled by the experimenter, and should not be useful in classification. If such features were important for classification, then the RF model may be affected by variation in task parameters, and not task performance.

Methods

Features used in the RF algorithm were assessed for variable importance 1. Briefly, cases not used in the bootstrapped dataset for a given tree, also known as the out of bag (OOB) cases, are run through the decision tree and the OOB error rate can be calculated. Per feature, the values for the OOB cases' given feature are then permuted and the difference between the permuted OOB error rate and observed can be calculated. This procedure can be repeated across all trees, and because each tree can be independent, a z-score can be calculated for each feature across all trees. Thus, this variable importance measure indicates which variables meaningfully contribute to classification.

The eight features showing improved classification accuracy were entered into a supervised random forest algorithm, to assess the performance of these eight features vs. including all 34 features across all tasks. Age and gender were not regressed in order to compare the RF performance with the original RF. 1000 iterations were run with 40 percent holdout (see: Supplemental Analysis 2; methods, for more details) for testing data and 60 percent as training data. Mean and standard deviation for total accuracy, sensitivity, and specificity are reported.

Results

FIG. 26 shows the variable importance for all 34 features. Only 8 of the 34 features contributed meaningfully to classification: mean stop task RT, standard deviation stop task RT, spatial span backwards RT, spatial span backwards span, spatial span forwards RT, accuracy on face identity task, accuracy on face emotion task, and RT on vocal affect task.

The eight feature RF performed similarly to the original RF. Total accuracy was slightly higher for the original (M=0.727, SD=0.087) than the eight feature (M=0.7144, SD=0.0577) RF. Sensitivity was higher in the eight feature (M=0.678, SD=0.114) than in the original (M=0.631, SD=0.153) RF. Specificity was higher in the original (M=0.807, SD=0.153) than in the eight feature (M=0.743, SD=0.0914) RF.

Discussion

Variable importance plot shows that eight features contribute to ASD classification. It is noteworthy that none of the eight features show a large relationship with gender or age (FIG. 19). Furthermore, features that are controlled by the experimenter, such as accuracy on the stop task, did not contribute meaningfully to classification. All eight of these measures are considered important when evaluating performance on these tasks. On the other hand, both the delayed discounting task and the continuous performance task did not contribute at all to classification. The results from the eight feature RF further suggest that the delayed discounting and continuous performance tasks did not dilute classification.

Summary of Findings

Taken together, the findings from the supplemental analyses suggest that ASD subgroups vary by typical heterogeneity. The features important for the model were not strongly associated with age and gender. However, controlling for age and gender altered subgroups and reduced classification accuracy to 62 percent. ASD subgroups did not vary significantly by symptom severity scores, however, ASD subgroups in both original and supplemental analyses varied by age and IQ, but in opposite directions. In the original analysis, the largest and most accurately classified ASD subgroup was youngest and had the lowest IQ; accurately classified TD and ASD subgroups did not differ by age and IQ. In the supplemental analysis, the most accurately classified ASD subgroups were older and had higher IQs; accurately classified TD and ASD subgroups differed by age, IQ, and gender. Based on these analyses, it is possible the subgroups identified by the supplemental RF were split by gender, and that the age and gender regression may have contaminated the data. Future studies should be cautious in choosing whether to perform such a regression prior to machine learning, especially if the input features and demographics show small relationships, but demographics and clinical outcomes are highly associated.

Example 3: Classification of ASD Subgroups Using Infomap

Example 3 relates to an application of models to identify clinical trajectories (see, e.g., FIG. 9), in the identification of ASD subgroups via RF and infomap. Diagnostic criteria were assessed via expert consensus. Parental assessments included the Social Responsiveness Scale (SRS), developmental history, the Child Communication Checklist (CCC-2). Clinical assessments included the Autism Diagnosis Observation Scale (ADOS). Features unused for scoring the ADOS were included in the model. All participants had their diagnosis confirmed by ADHD and ASD research diagnostic teams, and each team included two licensed psychologists and a child psychiatrist. Subjects taking prescribed psychoactive medication completed medication washout prior testing and scanning. Subjects taking prescribed psychoactive medication completed a medication washout to eliminate the effects of treatment on behavior and imaging measures.

Participants: Diagnostic measures were collected on 103 confirmed ASD positive and 78 confirmed negative participants. All participants were between the ranges of 9-13 years old. An additional 152 participants were used for Aim 2 below. Approach (FIG. 10): Clinical features were entered into a supervised RF model, which attempted to classify whether participants had a confirmed positive diagnosis. The RF model comprises a random ensemble of decision trees, where each tree can be generated using bootstrapped data from a subset of training data. Per tree, each branch can be determined by selecting the best feature, from a random subset of all the features, that minimizes training error, and the tree can be grown until the training data are classified. For a test or out of bootstrap aggregated (also referred to herein as "out-of-bag" or OOB) case, each tree votes on the classification, and the majority vote determines the class. In order to evaluate the success of the approach, 10 fold, 3 repetition cross-validation was performed. Data were divided into 10 folds, and per iteration, one fold can be held as testing data and the remaining nine are used to train the model. A permutation test was used to evaluate null performance, where the class labels for the participants were randomly shuffled per repetition.

Figure 28A:
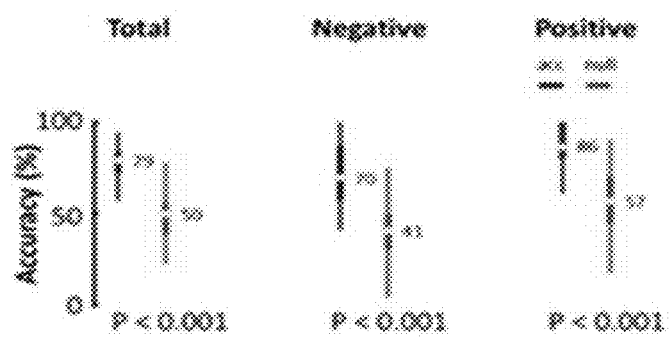
FIGS. 28A and 28B illustrate results related to Example 3 according to various implementations of the present disclosure.
Figure 28B:
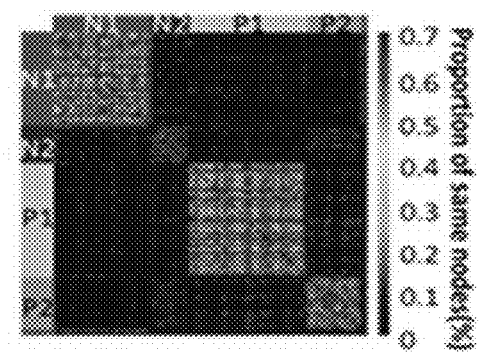

Results: Classification results are in FIG. 28A. The model showed greater sensitivity (%86.5, SD=%11.9) than specificity (%69.1, SD=%16.0), but both groups were classified above chance (p<0.001). Due to the model performance, two positive and two negative subgroups were identified from the resultant similarity matrix (FIG. 28B) using Infomap.

Conclusions: This preliminary study extends Examples 1 and 2, and demonstrates that the supervised RF approach can capture confirmed diagnoses in children with ASD, and a high probability of success for completing Aim 2. By tying the similarity matrix to the RF model performance, putative subgroups can be identified with context. Here, the identified subgroups likely reflect heterogeneity tied to a research confirmed ASD diagnosis. A prospective study can test whether this approach may benefit providers, and information from aim 2B will help design this study.

Example 4: Identifying ADHD Subgroups Using a Supervised Random Forest Model Example 4 relates to an application of the example model illustrated in FIG. 10 in the identification of ASD subgroups via RF and infomap. Diagnostic criteria were assessed via expert consensus. Parental assessments included the ADHD rating scale (ADHD-RS), and the Conners rating scale. Clinical assessments included the Kiddie Schedule for Affective Disorders and Schizophrenia (KSADS). Features unused for scoring the KSADS were included in the model. All children had their diagnosis confirmed by an ADHD diagnostic team, which included two licensed psychologists and a child psychiatrist. The unclean category represents subjects who did not meet criteria for the study for other reasons. For Aim 1, subjects taking prescribed psychoactive medication completed medication washout prior testing and scanning. Subjects taking prescribed psychoactive medication completed a medication washout to eliminate the effects of treatment on behavior and imaging measures.

Participants: Clinical diagnostic measures were collected on 520 participants from an ADHD study. All participants were between the ranges of 7-14 years old.

Approach (see, e.g., FIG. 10): Clinical features were entered into a supervised RF model, which attempted to classify whether participants diagnosis, which comprised 5 categories: typical, subthreshold ADHD, inattentive ADHD, combined ADHD, unclean. The RF model comprises a random ensemble of decision trees, where each tree can be generated using bootstrapped data from a subset of training data. Per tree, each branch can be determined by selecting the best feature, from a random subset of all the features, that minimizes training error, and the tree can be grown until the training data are classified. For a test or OOB case, each tree votes on the classification, and the majority vote determines the class. In order to evaluate the success of the approach, I performed 10 fold, 3 repetition cross-validation. Data were divided into 10 folds, and per iteration, one fold can be held as testing data and the remaining nine are used to train the model. A permutation test was used to evaluate null performance, where the class labels for the participants were randomly shuffled per repetition.

Figure 29:
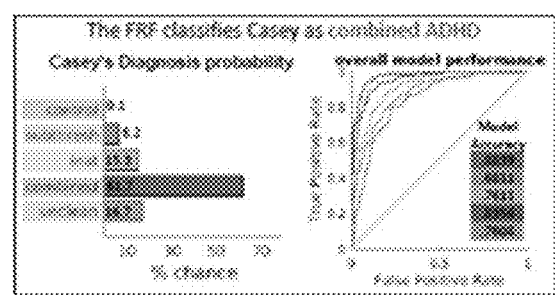
FIG. 29 illustrates results related to Example 4 according to various implementations of the present disclosure, including output from the clinical decision tool. The left side of FIG. 29 illustrates diagnosis probability per class for a given case. The right side of FIG. 29 illustrates a Receiver Operating Characteristic curve (ROC) plot representing overall model performance.

Results: FIG. 29 illustrates classification results of Example 4. As illustrated, the groups were classified above chance ($p<0.001$), with the lowest performance for the unclean group (0.7604 AUC).

Conclusions: This preliminary study extends Example 1, and demonstrates that the supervised RF approach can capture a "gold standard" diagnosis in children with ADHD, and a high probability of success for completing Aim 2. A prospective study can test whether this approach may benefit providers, and information from aim 2B will help design this study. Within this study, clinicians will be provided with information from the FRF (e.g., FIG. 29) as an additional diagnostic aid.

Example 5: Identifying ADHD Subgroups Using a Functional Random Forest Model Those with autism spectrum disorder (ASD) and/or attention-deficit-hyperactivity disorder (ADHD) exhibit symptoms of hyperactivity and inattention, causing significant hardships for families and society. A potential mechanism involved in these conditions is atypical executive function (EF). Inconsistent findings highlight that EF features may be shared or distinct across ADHD and ASD. With ADHD and ASD each also being heterogeneous, we hypothesized that there may be nested subgroups across disorders with shared or unique underlying mechanisms. In Example 5, participants included adolescents aged 7 to 16 with ASD (n=64) and ADHD (n=66). Typically developing (TD) participants (n=28) were included for a comparative secondary subgroup analysis. Parents completed the KSADS and youth completed an extended battery of executive and other cognitive measures. A two-stage hybrid machine learning model called functional random forest (FRF) was applied as a classification approach and then subsequently to subgroup identification. 43 EF variables were inputted to the classification step, a supervised random forest procedure in which the features estimated either hyperactive or inattentive ADHD symptoms per model. The FRF then produced proximity matrices, and Infomap algorithm (a type of community detection derived from graph theory) was used to identify optimal subgroups. Resting state functional connectivity MRI (rfMRI) was used to evaluate the neurobiological validity of the resulting subgroups. As a result of this analysis, both hyperactive (Mean absolute error (MAE)= 0.72, Null model MAE=0.8826, (t(58)=−4.9, $p<0.001$) and inattentive (MAE=0.7, Null model MAE=0.85, t(58)=−4.4, $p<0.001$) symptoms were predicted better than chance by the EF features selected. Subgroup identification was robust (Hyperactive: Q=0.2356, $p<0.001$; Inattentive: Q=0.2350, $p<0.001$). Two subgroups representing severe and mild symptomology were identified for each symptom domain. Neuroimaging data revealed that the subgroups and TD participants significantly differed within and between multiple functional brain networks, but no consistent "severity" patterns of over or under connectivity were observed between subgroups and TD. Accordingly, the FRF model estimated hyperactive/inattentive symptoms and identified two distinct subgroups per model, revealing distinct neurocognitive profiles of Severe and Mild EF performance per model. Differences in functional connectivity between subgroups did not appear to follow a severity pattern based on symptom expression, suggesting a more complex mechanistic interaction that cannot be attributed to symptom presentation alone.

Introduction

Although they co-occur sufficiently often to be clustered in the syndrome of Attention-deficit Hyperactivity disorder (ADHD), hyperactivity-impulsivity and inattention-disorganization comprise two partially separable symptom domains with distinct validation in regard to factor structure, clinical correlates, and neurobiology (Willcutt, E G, et al., J ABNORM PSYCHOL, 121(4), 991-1010 (2012)). The clinical significance of these problems in the adolescent period is substantial— they are associated with peer rejection (Nijmeijer et al., 2008), are strong predictors of worse academic outcomes (Breslau, N., et al., PSYCHOLOGICAL MEDICINE. (2010); Galéra, C., et al., PSYCHOLOGICAL MEDICINE (2009)) and related issues often persist throughout life (Doshi, J. A., et al., J AM ACAD CHILD ADOLESC PSYCHIATRY, 51(10), 990-1002 e2 (2012); Matza, L. S., et al., COST EFFECTIVENESS AND RESOURCE ALLOCATION: C/E, 3, 5 (2005)). However, although they are most pronounced and synchronous in individuals with ADHD (particularly the combined presentation), symptoms of inattention and hyperactivity are not necessarily confined to ADHD. Rather, they are an associated comorbid feature of many conditions (just as many conditions overlap with ADHD itself.)

ASD is a second neurodevelopmental population in which symptoms of hyperactivity and inattention are a substantial problem that has now been recognized in the DSM-5 (American Psychiatric Association. DSM 5 DIAGNOSTIC AND STATISTICAL MANUAL OF MENTAL DISORDERS. AMERICAN PSYCHIATRIC ASSOCIATION (APA) (2013)). Best estimates across studies utilizing clinical, in-lab, and national samples report that adolescents with ASD and comorbid ADHD broadly represent anywhere from ~28-50% of all ASD cases (Matson, J. L., et al., https://doi.org/10.1007/978-3-030-13027-5_3 (2019)). However, the number of adolescents with ASD experiencing sub-clinical hyperactive/inattentive symptoms are likely substantially higher (Stevens, T., et al., RESEARCH IN AUTISM SPECTRUM DISORDERS, 31, 11-18 (2016)). Moreover, ASD and ADHD appear to share some etiological features; for example, parents with ADHD have elevated rates of ASD offspring compared to parents without ADHD (Musser, E. D., et al., JOURNAL OF CHILD PSYCHOLOGY AND PSYCHIATRY AND ALLIED DISCIPLINES (2014)) and siblings cross aggregate within ADHD and ASD (Miller, M., et al., JAMA PEDIATRICS (2019)).

Atypical Executive Functions Might Relate to Hyperactive and Inattentive Symptoms A potential shared mechanism across ADHD and ASD—or at least ASD cases with elevated ADHD symptoms, is atypical executive functioning (EF) (Karalunas et al., 2018). EF can represent a collection of functions ranging in complexity, from holding two things in mind at once to complex sequential planning, but comprises abilities supporting self-monitoring and goal-oriented behavior (Welsh, M. C., et al., DEV NEUROPSYCHOL, 4, 199-230 (1988)). Although the best decomposition of EF into component functions is debated, a theme of unity and diversity recognizes that they have both shared and distinct elements (Friedman, N. P., et al., CORTEX (2017)). When statistically decomposed in factor analytic studies, examples of EF include working memory, inhibition, task-control, and cognitive flexibility (Baddeley, A. NATURE REVIEWS NEUROSCIENCE, 4(10), 829-839 (2003); Barkley, 1997; Diamond, 2013; Miyake, et al., COGNITIVE PSYCHOLOGY, 41(1), 49-100 (2000)). EF has been commonly associated with hyperactive and inattentive symptoms (Silverstein, M. J., et al., JOURNAL OF ATTENTION DISORDERS (2018); Willcutt, et al., BIOLOGICAL PSYCHIATRY, 57(11), 1336-1346 (2005) and the severity of EF impairments has also been linked to an increased number of ADHD symptoms for adolescents with ADHD and ASD (Semrud-Clikeman, M., et al., JOURNAL OF AUTISM AND DEVELOPMENTAL DISORDERS (2010); see also Semrud-Clikeman, M., et al., JOURNAL OF AUTISM AND DEVELOPMENTAL DISORDERS, 44(2), 331-342 (2014)).

These findings have led to several theories outlining the role of EF in inattentive and hyperactive symptom domains and ADHD (Barkley, R. A., PSYCHOLOGICAL BULLETIN, 121(1), 65-94 (1997); Nigg, J. T., PSYCHOLOGICAL BULLETIN, 126(2), 220-246 (2000)). However, several areas of EF functioning may be correlated with symptoms of inattention and hyperactivity (Kofler, Rapport, Bolden, Sarver, & Raiker, 2010; Martel, M. M., et al., JOURNAL OF ABNORMAL PSYCHOLOGY, 37(3), 337-348 (2009); Shiels, K., et al., CLINICAL PSYCHOLOGY REVIEW (2010); Willcutt, et al., 2005). As well, several of the same components of EF may be linked to hyperactive and/or inattentive symptom domains for those with ASD and/or ADHD (Sinzig, J., et al., CHILD AND ADOLESCENT PSYCHIATRY AND MENTAL HEALTH (2008)).

EF should Predict Hyperactive/Inattentive Symptoms but Study Results are Discrepant If EF tasks are measuring the same thing in children with ADHD and ASD, and if any proposed theories of EF and their relation to hyperactive/inattentive symptoms are correct, it is reasonable to assume that measures of EF should be able to predict the level of hyperactive/inattentive symptom severity among adolescents with ASD as well as those with ADHD.

For example, EF tasks can discriminate those with ADHD (i.e., a defined increase of hyperactive/inattentive symptoms) and typically developing (TD) adolescents (Holmes, J., et al., CHILD AND ADOLESCENT MENTAL HEALTH (2010)). Another study found that when comparing participants with ASD (without comorbid ADHD) to those with ADHD, the ADHD group showed greater impairment across all EF domains, pointing to the link between both hyperactive/inattentive symptom domains of ADHD and EF deficits. Inattentive symptoms were also significantly associated with EF deficits in metacognition for those with ASD and comorbid ADHD, indicating that metacognitive EF may be linked to inattention for those with ASD and ADHD (Berenguer, C., et al., RESEARCH IN DEVELOPMENTAL DISABILITIES (2018)). Meta-analysis indicates that although EF were associated with ADHD, effect sizes were moderate and findings were not universal per effected individual (Willcutt et al., 2005). This variability in the relationship between EF and ASD has also been demonstrated, but whether this is due to overlapping ADHD remains unclear (Karalunas et al., 2018).

Several Assumptions in the Literature Might be Related to these Discrepancies

It is increasingly recognized that EF are not a sole or sufficient explanation for elevated ADHD symptoms or for the ADHD syndrome (Nigg, J. T., BIOL PSYCHIATRY, 57(11), 1424-1435 (2005)) but that multiple routes can contribute to heterogeneity (Volkow, N. D., et al., MOLECULAR PSYCHIATRY (2011)). In addition, adolescents with ASD have shown measurable impairments in EF without a clinically significant number of hyperactive/inattentive symptoms (Karalunas et al., 2018). Thus, an interesting possibility is that some EF are specific to hyperactivity or inattention but other elements are non-specific or are more specific to ASD. The heterogeneity problem is, of course, significant across various example psychiatric disorders (Feczko, E., et al., TRENDS IN COGNITIVE SCIENCES (2019)) but quite notable for ADHD and ASD. This suggests that it may be more useful to study the relatively homogenous dimensions (inattention versus hyperactivity) to clarify the role of EF across ASD and ADHD, rather than the relatively heterogeneous syndrome of ADHD itself.

However, additional complexity is added to the study of EF and hyperactive/inattentive symptoms if one considers that the symptom domains across disorders are not necessarily caused by the same underlying mechanisms (Chan, Shum, Toulopoulou, & Chen, 2008; Molitor, S. J., et al., JOURNAL OF EMOTIONAL AND BEHAVIORAL DISORDERS (2018)). In other words, the complex relationship between symptom expression and EF deficits across disorders may also reflect shared liability. This proposes that ASD and ADHD share some etiological basis (Musser et al., 2014; Reiersen, A. M., et al., EXPERT REVIEW OF NEUROTHERAPEUTICS (2008)). While the limited literature thus far suggests common mechanisms across disorders, this concept is nevertheless important. For example, a recent study examining the relationship of EF and ADHD assessment for adolescents with ADHD, ASD, and learning deficits found that while all participants had higher scores than a typical population on inattention and hyperactivity, they clustered into unique cognitive profiles (Bathelt, J., et al., JOURNAL OF THE AMERICAN ACADEMY OF CHILD AND ADOLESCENT PSYCHIATRY (2018)). One group exhibited more problems with hyperactivity/inattention and EF across the board, a second showed reduced, but still clinically significant hyperactive/inattentive rates and primary deficits in inattention and not hyperactivity, while a third group showed more problems with EF despite having fewer hyperactive/inattentive symptoms. Importantly, while the first group consisted of mostly participants diagnosed with ADHD, all three groups contained children from each of the three diagnostic categories.

Overall, it is unclear which EF deficits persist among those with ASD and/or ADHD in light of, or in the absence of, hyperactive/inattentive symptoms. The underlying mechanisms may in fact be shared and distinct, both between and within the disorders (Karalunas et al., 2018; Rommelse, N., et al., JOURNAL OF NEURAL TRANSMISSION, 124(2), 259-271 (2017)). It has been insufficient in the literature to assume one common pattern of EF deficits within or between disorders. Instead, this Example 5 examines specifically how particular EF measures might explicitly relate to overall hyperactive/inattentive symptoms.

New approaches might help us better handle the "heterogeneity problem"

The fact that distinct mechanisms for ASD and ADHD for the same inattentive/hyperactive symptoms might be unique or whether these symptoms can be tied to EF transdiagnostically is an important question for the field (Lombardo, M. V., et al., BIORXIV, 278788 (2018)). Elucidating these mechanisms via transdiagnostic studies of shared symptoms themselves has the potential to direct treatment targets through precision medicine.

Newer machine learning techniques may offer an assistance by parsing out non-linear patterns in data that are missed with general linear model-based statistical tests and predictive modeling (see, e.g., Duda, M., et al., TRANSLATIONAL PSYCHIATRY (2016); Uluyagmur-Ozturk, M., et al., PROCEEDINGS—2016 15TH IEEE INTERNATIONAL CONFERENCE ON MACHINE LEARNING AND APPLICATIONS, ICMLA 2016 (2017)). Example 5 adopts a hybrid approach called the functional random forest (FRF) for tackling these issues. An FRF model combines supervised (machine learning) with unsupervised (graph theory) approaches. It does so by using a series of independent classifiers in a decision-tree approach to make predictions about an outcome using input data (see, e.g., Feczko, E., et al., NEUROIMAGE (2017)). After making these predictions, it then employs a community detection approach (see, e.g., Rosvall & Bergstrom, 2008) to identify subgroups based on shared and unique features among the participant data.

In various implementations, an FRF model identifies profiles (in this case of EF) based on features optimized for a relevant outcome (e.g., inattention) a priori, rather than post hoc.

While applying the FRF as a transdiagnostic approach to identify potential subgroups tackles the issue of tying EF to clinical phenotypes, in some cases, evaluating the clinical relevance of such subgroups can necessitate additional validation metrics. Utilizing an independent dataset and testing the model is one method for validating machine learning. Aside from testing generalizability or replication in an independent data set, within-sample cross-validation can be used and, in some cases, combined with secondary validation tests. In Example 5, internal cross-validation was performed and neurobiological correlates were identified using brain imaging as an index of validity (see, e.g., the validation methods described in Filiou, M. D., et al., INTERNATIONAL REVIEW OF NEUROBIOLOGY (2011)). In line with behavior-based EF studies, a data driven approach can better account for the heterogeneity of symptom expression as tied to brain imaging (Costa Dias, T. G., et al., DEVELOPMENTAL COGNITIVE NEUROSCIENCE, 11, 155-174 (2015); Karalunas et al., 2018; Ray et al., 2014). Therefore, utilizing the within and between brain-network connectivity as derived from resting state functional magnetic resonance imaging (fMRI) data serves to validate the existence of subgroups discovered by the FRF by informing the unique mechanistic underpinnings.

In Example 5, measures of EF in the FRF model were used to predict hyperactive and inattentive symptom domains among adolescents with ASD and/or ADHD transdiagnostically. In the method of Example 5, the presence of potential sub-populations across diagnoses that do not split by DSM categories for hyperactive or inattentive symptoms was identified. The identified subgroups were further validated using fMRI to examine group differences among the sub-populations within and between several brain networks.

Methods and Materials

Participant Demographics

FIG. 30 illustrates tables reporting demographics of participants in Example 5. Table 4 reports demographics for ASD and ADHD participants with significance tests. Table 5 illustrates demographics for ASD and ADHD participants with usable scan data. One hundred and thirty participants between the ages of 7-16 with a primary ASD diagnosis (N=64, female=13) or ADHD diagnosis (N=66, female=18) were included in the analysis (See Table 4 for demographic comparisons.) A TD group (n=28) was also included for descriptive purposes. These participants were demographically matched to ASD and ADHD participants with useable scan data (see: fMRI data, below, and Table 5 for demographic comparisons.

Although continuous measures across diagnostic categories were examined, rather than explicitly comparing groups, a batch effect is possible due to participant age differences. Because of this, the age differences and potential relationship to the EF variables were further examined.

Neuropsychological Tasks and Other EF Data:

In Example 5, multiple methods were used to assess EF including standardized cognitive batteries and a parent answered questionnaire. The battery was designed to comprehensively assess the aforementioned different domains of EF including response inhibition, working memory, task control, and cognitive flexibility (see Nigg, 2005; Pennington, B. F. EVOLUTION, NEUROBIOLOGY, AND BEHAVIOR (pp. 265-281) (1997); Pennington, et al., JOURNAL OF CHILD PSYCHOLOGY AND PSYCHIATRY, 37(1), 51-87 (1996)). Because impairments may vary across all of the EF domains, including tasks that cover a variety of potential impairments may provide a more comprehensive understanding of subgroup neurocognitive profiles. While many of the variables recruit more than one cognitive domain (Friedman & Miyake, 2017), the broad EF categories here can be considered as a context by which to consider the many components of EF.

Individual Task Descriptions and Review

A total of 43 variables from multiple behavioral tasks and one parent answered questionnaire were used as inputs in the FRF models. The measures span multiple cognitive domains as identified in the main manuscript, and are categorized into four broader domains including cognitive flexibility, response inhibition, working memory, and task control.

Verbal Fluency: Cognitive Flexibility

The verbal fluency task measures a participant's ability to recall and list out words in 2 categories (semantic: animals and food) and recall words beginning with a letter (phonemic: S and F) over a 1 minute span for each item. Including both categorical and letter fluency allows for the testing of semantic and phonemic word generation and retrieval. The verbal fluency task was audio recorded and reviewed by both the administrator and a secondary tester to verify the accuracy of administration and scoring. Variables included in the model were the semantic, phonemic, and contrast scores—all of which were scaled.

The majority of prior research indicates that those with ASD tend to perform worse on semantic word generation than their TD peers (Geurts, H. M., et al., JOURNAL OF CHILD PSYCHOLOGY AND PSYCHIATRY AND ALLIED DISCIPLINES, 45(4), 836-854 (2004); Spek, Schatorje, & Scholte, 2009; Verté, Geurts, Roeyers, Oosterlaan, & Sergeant, 2006). Still, some researchers have shown equal numbers of total semantic word production for ASD and TD children and adolescents (ages 6-23) (Begeer et al., 2014). Another group found delays in performance on letter fluency for ADHD adolescents as compared to TD (Hurks et al., 2004).

In one study, male ASD participants performed a VF task while undergoing fMRI (Kenworthy et al., 2013). They found reduced activity in regions associated with executive control compared to TD, despite no significant differences in word generativity. The ages of the participants in this study were similar, but had mean of 16(ASD) and 17(TD) years old, putting both groups over the threshold where one would expect ASD participants to perform more similarly to their TD peers.

Behavior Rating Inventory of Executive Function (BRIEF): Response Inhibition, Cognitive Flexibility, Working Memory, Task Control The BRIEF is a parent answered questionnaire that covers a broad range of EF as exhibited by the child in everyday life. For example, an item from the emotional control module states "Has explosive angry outbursts" and the parent is asked to rate the truthfulness of the statement, as it pertains to their child, as never (1), sometimes (2), or often (3). The scored categories include inhibition, shifting, emotional control, working memory, planning and organizing, organization of materials, monitoring, behavioral regulation, and metacognition. Parents answered the questionnaire on a computer or tablet. T-Scores from all domains were included in the model.

The newness of the BRIEF (2000) may contribute to the limited amount of research. Children with ADHD have shown impaired ratings on the BRIEF, and the BRIEF itself is highly correlated with other questionnaire based measures of EF (Mahone et al., 2002). One group examining ASD and TD participants found that by applying a graph theory metric derived from task and rest states, they could successfully predict a subject's BRIEF metacognition index based on changes within the frontoparietal, salience, and subcortical networks (Lynch et al., 2017). As previously mentioned in the main manuscript, the BRIEF has also been used to examine the connection between EF and everyday impairments (Gardiner & Iarocci, 2017).

Color Word Interference: Response Inhibition

The D-KEFS Color-Word Interference test is based on the Stroop procedure and involves a participant's ability to inhibit a learned response. In this case, we examined the inhibitory condition in which a subject is asked to name the color of the ink that a dissonant color word name was printed in. For example, the word "blue" might be printed in red ink and therefore, the correct verbal response is "red." Variables included in the model were the time to complete the task, uncorrected errors, self-corrected errors, and total errors—all of which were scaled.

Inhibiting a response using the stroop task has been found to be largely in-tact for those with ASD (Adams & Jarrold, 2012). However, as with many other studies, comorbid ADHD is often unaccounted for when comparing ASD participants to TD. Because some ASD participants may perform worse than others based on varying levels of ADHD symptoms, the stroop task was included in the models. Some researchers have found no differences on performance between two ADHD "subtypes" (combined and inattentive) and their TD peers, but did find that the ADHD subtypes were slower than the TD group which may reflect a compensatory mechanism (Nigg, Blaskey, Huang-Pollock, & Rappley, 2002). For this reason, both performance and time scores were included in the models.

Digit Span: Working Memory (Auditory)

The WISC-IV Digit Span task measures a child's ability to both recall and manipulate information in short-term storage. A series of numbers are spoken aloud by the tester and the child is then asked to recall them either in forward or backward order. The amount of numbers in the sequences increase as the child responds correctly to each administration. For the model, the backward and forward scaled scores, and percentiles for the longest digit recalled both backward and forward, were included.

Broadly, working memory is known to be impaired in those with ADHD, but there is conflicting research regarding the role of auditory working memory in ASD. Some researchers found that ASD subjects show working memory deficits similar to those seen in individuals with EF impairments (Bennetto, Pennington, & Rogers, 1996). However, another study showed that working memory may perhaps be in-tact (Ozonoff & Strayer, 2001). It's possible that differences in performance may be due to varying numbers of ASD individuals with comorbid ADHD impairments in any given cohort, which is not accounted for in these studies. Another limitation is the inclusion of only a single working memory measure, rather than including auditory and spatial working memory in the same analysis.

Trails: Cognitive Flexibility

In the trail making task the 4th condition (number-letter switching) is the primary condition used to assess EF domains of switching, sequencing, and task control. In condition 4, the participant is asked to trace a line from "a number (1) to a letter (A) to a number (2) to a letter (B) and so on, in order, until they reach the end (16)." Variables included in the model were the total time to completion, sequencing errors, set loss errors, and total errors. All of the variables were scaled or percentiles.

Two studies showed no significant differences on versions of the trail making task between ASD and TD (Nakahachi et al., 2006), and high-functioning autism (HFA) and TD groups (Losh et al., 2009). Another study compared ASD, ADHD, and TD participants and showed that the ASD group differed from both the ADHD and TD groups (Corbett, B. A., et al., PSYCHIATRY RESEARCH, 166(2-3), 210-222 (2009)). However, each of the aforementioned mentioned studies used either a different version of the trails task (DKEFS or ATMT) or a different task type (switching vs. sequencing.) These slight differences in effect, make it harder to compare results across studies as they may be measuring similar, but slightly different parts of EF. Including the time to completion as well as different types of errors (sequencing or set-shifting) provides a more comprehensive picture of EF deficits.

D-KEFS Tower Test: Cognitive Flexibility, Task Control

The tower test is a table task that requires a participant move disks of varying sizes across three pegs in order to match their tower to the specified picture using the fewest possible number of moves. When administered correctly, the complexity of the task enables the measurement of multiple EF domains including cognitive flexibility and task control. The tower task was video and audio recorded, and then reviewed by both the initial tester themselves and a secondary rater to verify the accuracy of both administration and scoring. Variables included the mean accuracy of the time to first move, overall accuracy, rule violations per item administered, time per move, total achievement score, and total rule violations. All of the included variables were either scaled scores or percentiles.

Researchers using a similarly constructed task showed no significant differences between ASD and TD individuals on a MANCOVA for Planning (minimum moves, initial thinking, and subsequent thinking) (Corbett et al., 2009). HFA participants have also shown associations between planning deficits on the tower task and reduced efficiency in visuospatial short-term memory (Zinke et al., 2010). Another group showed that ASD youth had the lowest global performance compared to ADHD and TD groups, but that those with comorbid ASD and ADHD showed greater improvement trajectories than those that were ASD alone (Unterrainer et al., 2015). Inclusion of the tower variables might enable for a better understanding of how these impairments relate to other cognitive domains in individuals with ASD and/or ADHD.

Stop Task: Response Inhibition, Task Control

The go/no-go Stop Task measures a participant's ability to both react quickly to a stimuli and to inhibit a response. In brief, participants fixate on a white screen and are presented with a rainbow "X" or "O." They are asked to either make a key press corresponding to the X or O, or to inhibit their response at the presentation of an auditory tone. The variables used in the model included an accuracy measure of X/O key press on go-trials, a probability measure of inhibition on stop-trials, the stop signal reaction time, mean reaction time on go-trials, and the standard deviation of reaction times on go-trials. While accuracy of X/O key press on go-trials serves as a control for other task variables, it may also provide information about letter anticipation which may be task-control related and thus was included in the models. Justifications for including data in the FRF should be carefully considered, but another benefit of the FRF is that it successfully ignores features that show no valuable contribution. Because the stop task is not scaled, potential age confounds were also examined in the supplementary analyses.

It has been widely demonstrated that participants with ADHD perform worse than their TD peers on the stop task (Senderecka, Grabowska, Szewczyk, Gerc, & Chmylak, 2012). Yet for one study that covaried for ADHD symptoms in ASD and ADHD groups, these differences all but disappeared—with the exception of the ASD group showing increased premature responses (Carter Leno et al., 2017). Meta-analyses on response inhibition in ASD, including the stop-task, further emphasized that heterogeneity of ASD may have an effect on the inconsistent results (Hilde M. Geurts, van den Bergh, & Ruzzano, 2014). As evidenced by the inconsistencies across the literature. Similar to other researchers, consideration of comorbidities such as ADHD is recommended, as well as looking further into ASD subtypes.

Spatial Span: Working Memory

The spatial span is a computerized task that measures spatial working memory. The task presents 10 white boxes in random locations on the screen—a subset of which change color, one at a time, in a fixed order. In the Forward task, upon completion of the color change sequence, subjects hear a tone and are asked to click on the boxes in the order in which they changed color on the screen. The number of squares that change color range from 3 to 9, with two trials for each span length, and the task discontinues when a child fails both trials of the same span. The Backward task is presented in the same way, but instead, subjects are asked to click on the boxes in the opposite order in which they appeared. The forward and backward spans were counterbalanced and subjects had the opportunity to practice prior to administration of the task. Because the spatial span task is not scaled, potential age confounds were further analyzed.

Several recent studies have suggested both impaired (Chen et al., 2016) and non-impaired (Macizo, Soriano, & Paredes, 2016) spatial working memory among those with ASD. Stronger evidence exists to support such an impairment among those with ADHD, as they have been shown to exhibit deficits in visio-spatial working memory as compared to TD peers across multiple studies (Kasper, Alderson, & Hudec, 2012). A study comparing participants with ADHD, ASD+ADHD, ASD, and TD on a spatial working memory task showed that ADHD participants performed worse than both the TD and ASD+ADHD groups and that both ASD+ADHD and ADHD groups needed longer to perform the task than TD and ASD (Sinzig, Morsch, Bruning, Schmidt, & Lehmkuhl, 2008).

Missing Data

Very few data points were missing in the dataset gathered for Example 5. Of the 43 input variables used in the model for all participants, only 0.9% of the total data was missing. The participants averaged 0.7% missing data each, with the maximum amount of missing data for a single participant at 14% and only 10% of participants with any missing data at all.

fMRI Data

Participants were scanned at OHSU's Advanced Imaging Research Center (AIRC) on a 3.0 T Siemens Tim Trio Magnetom scanner using a 12 channel head coil, and completed one T1 weighted structural image as well as 3 5-minute resting state scans. All of the data were processed using a modified version of the Human Connectome Project (HCP) image processing pipeline (Glasser et al., 2013; Mills, B. D., et al., NETWORK NEUROSCIENCE (Cambridge, Mass.), 2(2), 200-217 (2018)). After processing, a manual curation process was used to further assess the data quality.

Figure 31:
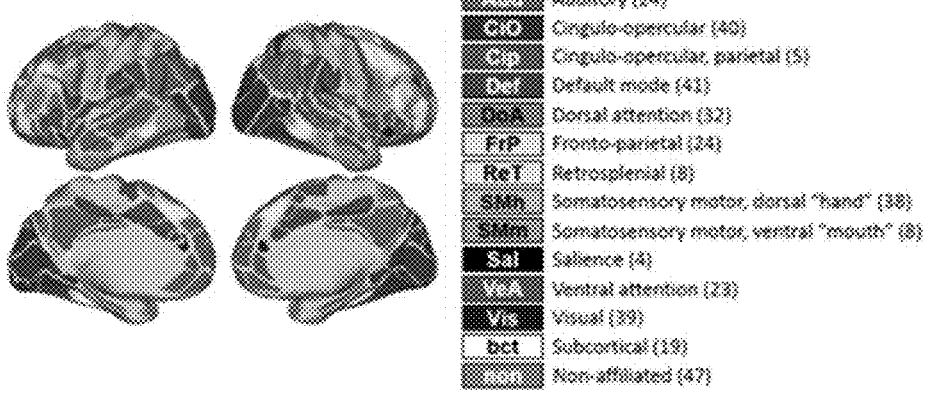
FIG. 31 illustrates the 352 Regions of Interest (ROIs) analyzed in Example 5.

FIG. 31 illustrates the 352 Regions of Interest (ROIs) analyzed in Example 5. The ROIs included 19 subcortical regions. The ROIs were generated based on previously identified parcellation schemes (e.g., Gordon Parcellation; Gordon et al., 2014). The identified networks are illustrated in FIG. 31 with the number of assigned ROIs and color-coded by network.

To analyze the imaging data, the ROIs, including 19 subcortical regions, were generated based on previously informed parcellation schemes. Individual parcellation matrices were generated per subject, then subgroup matrices were created by averaging each individual matrix across subgroups.

Analysis Overview

Functional Random Forest and Subgroup Detection

An FRF model was used in two separate models to estimate either the participant's total hyperactivity or total inattentive ADHD symptom total score from the Kiddie Schedule for Affective Disorders and Schizophrenia (K-SADS) ADHD module (Kaufman, J., et al., J AM ACAD CHILD ADOLESC PSYCHIATRY, 36(7), 980-988 (1997)). Input (predictive) measures include the 43 variables from the EF tasks and the EF questionnaire.

The FRF algorithm constructed a series of 1000 decision trees using the input EF measures. Each tree was then given a bootstrapped subset of randomly selected training data to optimize performance. From there, a random selection of participants and variables excluded from the training data were used to evaluate the overall accuracy of the model using 10-fold, 3 repetition, cross-validation by comparing the accuracy distributions from 30 permutation tests against 30 null models with a t-test (Kohavi, R., A study of cross-validation and bootstrap for accuracy estimation and model selection in INTERNATIONAL JOINT CONFERENCE ON ARTIFICIAL INTELLIGENCE (IJCAI) (pp. 1137-1145) (1995)). Twenty trees were used to determine surrogate splits for the training data (Breiman, 2001).

A proximity matrix was then generated from the decision trees, wherein each cell in the matrix indicated the number of times across all trees and forests that any given two participants end up in the same terminal branch. Community detection via the infomap algorithm (described, e.g., in Rosvall & Bergstrom, 2008) was then used to identify subgroups from this proximity matrix, with nodes and edges determined in steps of a 0.05 threshold from 0.2 to 1. To determine the optimal groupings, an iterative procedure using matrix thresholds from 0.2 to 1 in steps of 0.05 was used to identify a consensus of subgroup assignments from all generated thresholds.

Imaging Data and Chi-Squared Test:

To help validate the subgroups, parcellated matrices for each subgroup (see: fMRI data) two mass univariate analysis of variance (ANOVA) tests, and a chi-squared analysis (described, e.g., in Eggebrecht et al., 2017) were used to identify significant differences in functional connectivity between the subgroups ascertained from each model.

For every ROI to ROI pair, as represented in the parcellated matrices, the ANOVA tests were used to measure significant differences in correlations between 1) the identified Hyperactive Subgroups (HSG) and the TD group and 2) the identified Inattentive Subgroups (ISG) and TD group. For the chi-squared analyses, the results of the ANOVAs were then binarized at p<0.05 significance. An expectancy ratio was subsequently calculated by comparing the number of expected significant and non-significant functional connections to the observed number. A chi-squared test statistic was then calculated from the observed and the expected ratio of significant connections. Permutation tests were used to construct an empirical distribution of null chi-squared tests to determine the statistical significance of the observed chi-squared test statistics. FDR correction was used to control for multiple comparisons.

Results

Hyperactive Model EF Prediction and Subgroups Across ASD and ADHD

Figure 32A:
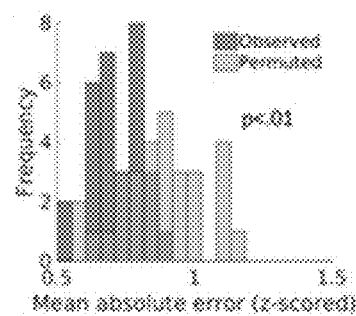
FIGS. 32A and 32B illustrate results of the Hyperactive model and the Inattentive model with subgroups across ASD and ADHD.
Figure 32B:
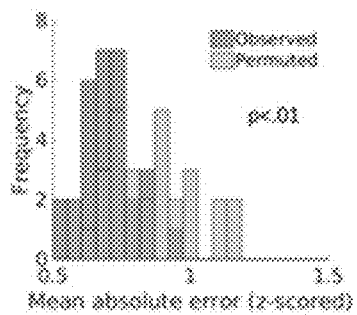

FIGS. 32A and 32B illustrate results of the Hyperactive model and the Inattentive model with subgroups across ASD and ADHD. FIG. 32A illustrates the mean absolute error (MAE) over permutations of the Hyperactive model (teal) plotted in a histogram with the MAE of the null module permutations (tan). FIG. 32B illustrates MAE over permutations of the Inattentive model (purple) plotted with the MAE of the null model. The FRF predicted the hyperactivity scores among ASD and/or ADHD participants better than the null model (Mean absolute error (MAE)=0.72, Null model MAE=0.8826, (t(58)=−4.9, p<0.001) (FIG. 32A)

There was no significant difference observed in the model performance between subgroups (Hyperactive error: t(128)= v−1.107, p=0.271.)

Figure 33A:
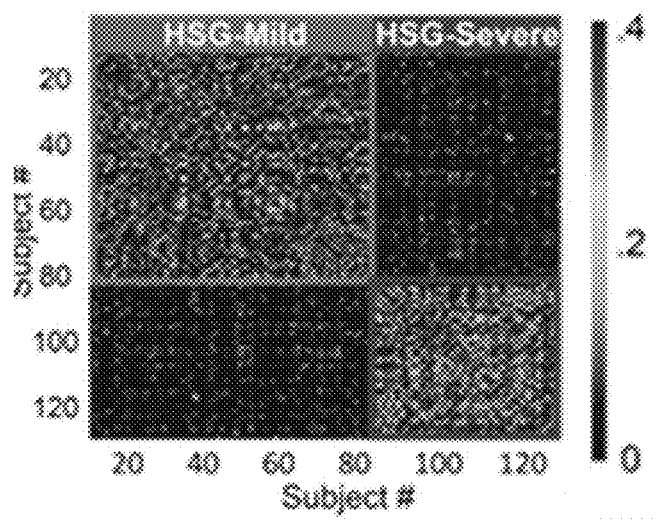
FIGS. 33A and 33B illustrate proximity matrices produced by the Hyperactive and Inattentive FRF models.
Figure 33B:
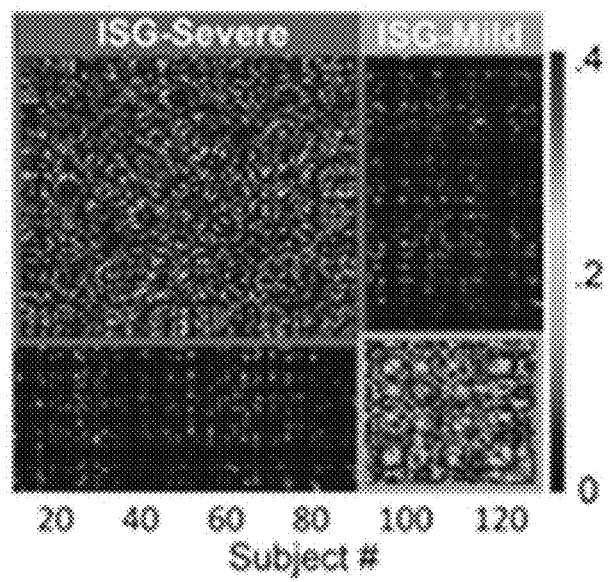

FIGS. 33A and 33B illustrate proximity matrices produced by the Hyperactive and Inattentive FRF models. FIG. 33A illustrates a proximity matrix produced by the Hyperactive FIRF model. The participants were reorganized into Hyperactive model subgroups (HSGs) identified via infomap. The HSGs were captured in teal squares to show the boundaries of each subgroup. A colorbar included in FIG. 33A indicates the proportion of times each participant ended up in the same terminal branch as another participant on the alternate axis over FRF permutations. FIG. 33B illustrates a proximity matrix for the Inattentive FRF model, reorganized into identified Inattentive model subgroups (IMS) and captured in purple squares to show the boundaries of each subgroup.

Community detection identified two unique subgroups in the Hyperactivity model (FIG. 33A) The subgroups were split with 79 participants in HSG-1 (Mild; ASD=40, ADHD=39) and 51 in HSG-2 (Severe; ASD=24, ADHD=27).

FIG. 34 illustrates Table 6, which provides demographics for identified Hyperactive subgroups and significance tests comparing HSG-Mild and HSG-Severe. As illustrated in FIG. 34, there were no significant observed differences between the subgroups on diagnostic composition of ASD and ADHD participants per subgroup, gender, age, or estimated IQ.

Figure 35A:
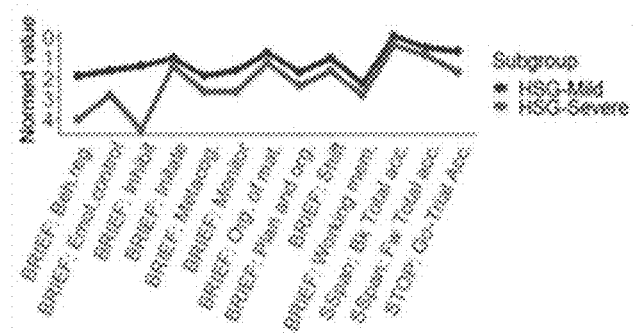
FIGS. 35A and 35B illustrate behavioral measures used in the FRF Hyperactive model (FIG. 35A) and the FRF Inattentive model (FIG. 35B).
Figure 35B:
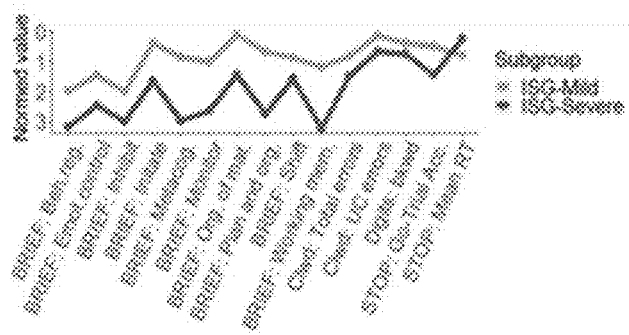

FIGS. 35A and 35B illustrate behavioral measures used in the FRF Hyperactive model (FIG. 35A) and the FRF Inattentive model (FIG. 35B). FIGS. 35A and 35B show observable differences between the subgroups. Normed means (y axis) from Table 8 are plotted on the x axis of FIG. 35A in a line plot. To emphasize the true differences when compared to a normative sample, the measures in each of FIGS. 35A and 35B have been normed to the TD group. In addition, normed means (y axis) from Table 9 are plotted on the x axis of FIG. 34B in a line plot.

FIG. 36 illustrates Table 7, which provides variables included in the Hyperactive model that measurably differed between identified subgroups. Table 7 is organized by primary cognitive domain on the left. T-tests comparing identified subgroups (HSG-Severe, HSG-Mild), with degrees of freedom in parentheses, are shown for each variable. Columns for HSG-Severe and HSG-Mild show their groups means, normed to the TD sample.

As shown in FIGS. 35A to 36, HSG-Mild had significantly better EF performance and ratings than HSG-Severe across all of the cognitive domains on several of the tasks. Note that the plots in FIGS. 35A and 35B are scaled as z-scores relative to the TD population such that 0=TD mean and all points below 0 are weaker performance and all scores above 0 are better. Thus FIG. 35A highlights lower scores on all measures for both subgroups. HSG-Mild had better ratings than HSG-Severe on multiple BRIEF modules involved in response inhibition (inhibit, emotional control, monitor), cognitive flexibility (shift, behavioral regulation, metacognition), working memory (working memory), and task control (initiate, plan and organize, organization of materials). HSG-Mild also showed better working memory (spatial span; backward and forward total accuracy.)

Inattentive Model EF Prediction and Subgroups Across ASD and ADHD

As shown in FIG. 32B, the FRF also predicted the inattentive scores for our participants with greater accuracy than the null model (MAE=0.7, Null model MAE=0.85, t(58)=−4.4, p<0.001). There were no significant differences observed in model performance between subgroups (Inattentive error: t(128)=−0.494, p=0.622). FIG. 33B shows that community detection identified two distinct subgroups for the inattentive model.

In the Inattentive model, the subgroups were split with 84 participants in ISG-1 (Severe; ASD=38, ADHD=46) and 46 in ISG-2 (Mild; ASD=26, ADHD=20). FIG. 37 illustrates Table 8, which provides demographics for identified Inattentive subgroups and significance tests comparing ISG-Mild and ISG-Severe. There were no significant differences observed between the subgroups on diagnostic composition of ASD and ADHD participants per subgroup, gender, age, or estimated IQ FIG. 38 illustrates Table 9, which provides variables included in the Inattentive model that observably differed between identified subgroups. The variables are organized by primary cognitive domain. T-tests comparing identified subgroups (ISG-Severe and ISG-Mild), with degrees of freedom in parentheses, are shown for each variable. Columns for ISG-Severe and ISG-Mild show their groups means, normed to the TD sample. As shown in FIGS. 35B and 38, ISG-Mild had significantly better performance and ratings than ISG-Severe across all cognitive domains on several tasks.

ISG-Mild was rated better on multiple BRIEF modules involved in response inhibition (inhibit, emotional control, monitor), cognitive flexibility (shift, behavior regulation, metacognition), working memory (working memory), and task control (initiate, plan and organize, organization of materials). ISG-Mild also demonstrated better performance on tasks involved in response inhibition (stop task accuracy) and working memory (digit span backwards). Interestingly, ISG-Mild had a slower reaction time than ISG-Severe on the stop task which may reflect a speed-accuracy tradeoff (Heitz, R. P., FRONTIERS IN NEUROSCIENCE (2014); Mulder, M. J., et al., BIOLOGICAL PSYCHIATRY, 68(12), 1114-1119 (2010)), for ISG-Mild also showed better accuracy than ISG-Severe within the same task.

Brain Connectivity Differences Between Subgroups

In the Hyperactive model, 38 participants from HSG-Mild (ASD=16, ADHD=22) and 29 from HSG-Severe (ASD=10, ADHD=19) met the requirements for analyzable imaging data and were subsequently included in the analysis along with the matched TD group (n=28).

Figure 39A:
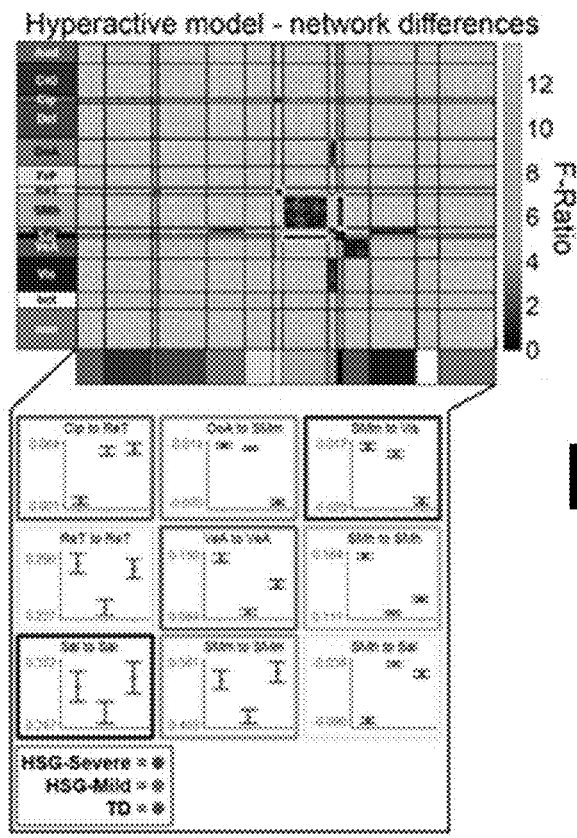
FIGS. 39A and 39B illustrate network connectivity associated with the Hyperactive (FIG. 39A) and Inattentive (FIG. 39B) models.
Figure 39B:
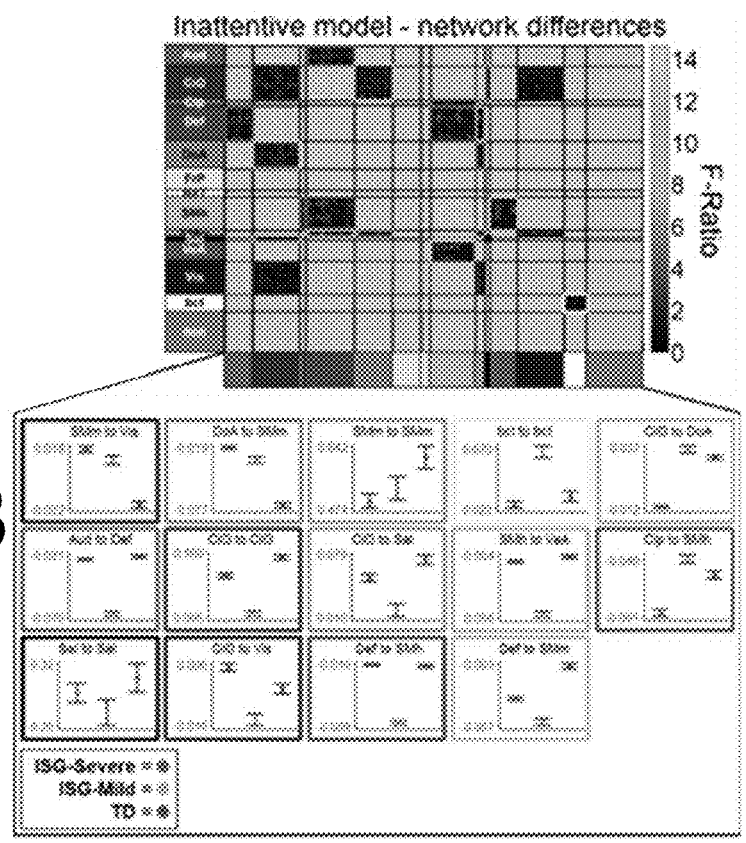

FIGS. 39A and 39B illustrate network connectivity associated with the Hyperactive (FIG. 39A) and Inattentive (FIG. 39B) models. As shown in FIG. 39A, using the ANOVA and chi-squared test, several network connections were significantly different between the three groups of the Hyperactive model (e.g., HSG-Severe, HSG-Mild, and TD). Connectivity differences did not appear to follow severity patterns based on ADHD symptoms an EF impairment. For example, although the TD group showed significantly greater connectivity between the cingulo-opercular parietal (CiP) and retrosplenial (ReT) (FIGS. 31 and 39A) networks as compared to HSG-Mild, and HSG-Mild was significantly greater than HSG-Severe, nearly all other network connections show no distinguishable trends—with the TD, Mild, and Severe groups swapping directionality depending on the connection.

In the Inattentive model, 47 participants from ISG-Severe (ASD=17, ADHD=30) and 20 from ISG-Mild (ASD=9, ADHD=11) were determined to have enough good imaging data and were analyzed along with the comparison TD group. As shown in FIG. 39B, using the combined ANOVA and chi-squared test, many network connections were significantly different between the three groups. This same "non-pattern" emerged across networks, with the first three network connections on 5b showing severity trends, and the remaining 11 connections having no distinguishable patterns as related to ADHD symptoms and EF impairment.

Discussion

Results Summary

Using EF Variables in the FRF Models, we Predicted ADHD Symptom Severity for Participants with ASD and/or ADHD Better than Random Chance Example 5 links behavioral variables from the EF tasks and rating scale directly to clinical hyperactive/inattentive outcomes for ASD and ADHD participants using the FRF approach. EF measures predicted hyperactivity and inattentive symptom counts better than random chance for both of the models. Example 5 also shows that task and ratings measures both contributed, something many prior reports did not do. Because task and ratings measures that purport to measure executive functions typically do not correlate very well, it is unclear they measure the same construct. Thus, it is reassuring that here they both contributed to the prediction model.

Example 5 also identified subgroups and further validated them by confirming neurocognitive phenotypes. Different combinations of EF variables helped identify the unique profiles among participants, thereby informing subgroups. Example 5 identified two subgroups per hyperactive/inattentive model using community detection. The identified subgroups differed significantly on measures that are purportedly related to multiple EF processes.

These results support the growing supposition in the field that there may be multiple mechanistic subgroups across diagnostic categories in these neurodevelopmental disorders (E. Sonuga-Barke, Bitsakou, & Thompson, 2010). In other words, several different underlying causes may also lead to similar phenotypes that inform subgroups. In our study the subgroups did not split by participant diagnosis, indicating that features of EF may be shared transdiagnostically.

To determine if subgroups had real, measurable differences in their biological underpinnings, Example 5 further validated them via neuroimaging and compared them to a TD population. Some of the imaging results appeared to follow a severity trend (i.e. ISG-Severe showing decreased connectivity between identified regions compared to ISG-Mild, which is decreased compared to TD.) However, the entirety of the results do not follow a discernable trend. For example, it may be expected that high performing groups showing "greater" connectivity between related functional networks, such as attentional and default, as compared to a lower performing group. It appears that the subgroups cannot simply be measured on a continuum of functional-connectivity and rather, may have unique underpinnings.

Measures of EF estimate hyperactive and inattentive symptoms in adolescents with ASD and/or ADHD Multiple theories have been proposed regarding the relationship between EF and hyperactive/inattentive symptoms (Castellanos, F. X., et al., TRENDS IN COGNITIVE SCIENCES, 10(3), 117-123 (2006); Corbett, Constantine, Hendren, Rocke, & Ozonoff, 2009; Martel, M., et al., JOURNAL OF THE AMERICAN ACADEMY OF CHILD AND ADOLESCENT PSYCHIATRY, 46(11), 1437-1444 (2007); Sonuga-Barke, E., et al., JOURNAL OF THE AMERICAN ACADEMY OF CHILD AND ADOLESCENT PSYCHIATRY, 49(4), 345-355 (2010); Thorell, L. B. JOURNAL OF CHILD PSYCHOLOGY AND PSYCHIATRY AND ALLIED DISCIPLINES (2007)). The results of Example 5 support growing evidence that while EF are involved in perceived hyperactive/inattentive symptoms across ASD and ADHD, they are not the sole cause. This was evidenced by the contribution of the BRIEF to model performance, showing that it may be measuring something slightly different than the other EF tasks which were also included in the models.

Importantly, until recently, many of the prior studies have not been conducted transdiagnostically (Geurts et al., 2004; Joshi, G., et al., JOURNAL OF ATTENTION DISORDERS, 21(10), 846-855 (2017)). Indeed Example 5 builds on a handful of recent studies that have employed transdiagnostic approaches (Dajani, D. R., et al., NEUROIMAGE: CLINICAL, 21 (2019); Karalunas, S. L., et al., JOURNAL OF ABNORMAL CHILD PSYCHOLOGY (2018); Lecei, A., et al., NEUROIMAGE: Clinical (2019)). Such studies suggest that impairments across ASD and ADHD are not entirely attributable to comorbid diagnoses (Karalunas et al., 2018). While not informing 'causality,' our results compliment these findings, demonstrating that EF may be tied to hyperactive/impulsive symptoms for those with ADHD and/or ASD.

Subgroups were Identified Based on Unique Combinations of EF Features for Both Hyperactive and Inattentive Models A growing body of evidence suggests multiple pathways lead to shared symptoms among a given disorder (Castellanos et al., 2006; Eric Feczko et al., 2019). Yet challenges arise in understanding the association between domains (e.g., EF) and outcome (e.g. hyperactive/inattentive symptoms), while accounting for multiple pathways and nested subgroups. Knowing these challenges, the FRF was used in prior work with a different clinical question in mind. In that study the model identified 3 ASD and 4 TD subgroups (Feczko et al., 2017) based on measures of EF and facial/vocal affect recognition and processing. As such, the outcome of interest is a critical component in guiding the research question itself. In our case, we probed the role of hyperactive and inattentive symptoms by looking at predictive accuracy and determining whether more than one pathway is present for a given outcome.

FRF was Employed to Tie EF to Clinical Outcomes and Identify Neurocognitive Phenotypes Thus, Example 5 demonstrates applications of the FRF using EF to examine their relationship to hyperactive and inattentive symptoms across ASD and ADHD, and to determine whether more than one 'pathway' exists for these outcomes. A secondary benefit of such an approach was also accomplished in Example 5. By including both ADHD and ASD participants in a trans-diagnostic study, a characterization of whether hyperactive or inattentive symptoms are related to the same underlying mechanisms across disorders can be achieved. If the identified subgroups split by primary diagnostic category, it would indicate that the mechanisms leading to observed ADHD symptoms are potentially distinct. Inversely, if the subgroups share participants across ASD and ADHD, it would indicate that the mechanisms are likely to be shared. With EF features creating "pathways" to the ADHD outcome of interest, ASD and ADHD participants end up in the same or different subgroups.

In employing the FRF approach, Example 5 illustrates the existence of sub-groups that differed on severity of multiple EF features, representing putatively mild and severe subgroups per model. The hyperactive subgroups differed on measures related to multiple cognitive domains—with HSG-Mild showing improved performance across multiple measures of EF as compared to HSG-Severe. HSG-Mild also showed fewer total hyperactivity symptoms than HSG-Severe.

The inattentive subgroups showed observable differences on multiple measures of EF, with ISG-Mild out-performing/ showing better ratings than ISG-Severe across tasks. Most notable was ISG-Mild's slower reaction time on the stop task as compared to ISG-Severe. This may reflect a speed-accuracy tradeoff (Heitz, 2014; Mulder et al., 2010) in which ISG-Mild is compromising speed in order to improve performance accuracy on the task. This tradeoff may also be reflected in their superior stop task accuracy score compared to ISG-Severe. As several studies have confirmed the variability of performance of ADHD participants on inhibitory tasks (Huang-Pollock, C. L., et al., JOURNAL OF ABNORMAL PSYCHOLOGY, 121(2), 360-371 (2012); Karalunas, S. L., et al., NEUROPSYCHOLOGY (2012); Mulder et al., 2010), our results may further validate the necessity for subgroup splitting.

Importantly, Example 5 also demonstrates that the subgroups in both analyses were not defined by diagnostic category (Tables 7 and 8), indicating that the underlying mechanisms leading to observed symptoms are likely shared across disorders. This is consistent with previous work suggesting that causes of ADHD symptoms in those with ASD and/or ADHD may share an underlying mechanism (Leitner, Y., FRONTIERS IN HUMAN NEUROSCIENCE (2014)), even though there may be more than one (Chan, et al., ARCHIVES OF CLINICAL NEUROPSYCHOLOGY, 23(2), 201-216 (2008); Eric Feczko et al., 2019; Molitor et al., 2018). The results of Example 5 further support the transdiagnostic approach given the aforementioned fact that our subgroups did not split based on diagnostic category.

Other modeling approaches, such as latent class analysis, have been used to derive low and high performing groups (Fair 2013, Karalunas 2014, Katuwal, Baum, Cahill, & Michael, 2016). The difference between the FRF approach and other methods is that the FRF may discover any number of groups or none at all, as demonstrated in prior work (E. Feczko et al., 2017). In addition, the discovered groups may vary depending on outcome of interest. In other words the low and high performing groups, identified in the current work, are tied to the relevant symptom dimensions, and other outcomes (e.g, prognosis, response to therapy, etc), are likely to reveal distinct grouping characteristics.

Hyperactive and Inattentive Subgroups were Comprised of Different Participants Per Subgroup Another important observation in the data of Example 5 is that subgroups defined for inattentive symptoms and those for hyperactive symptoms were comprised of unique participants. This finding highlights that the identified subgroups are not simply duplicated across the two models. The result is consistent with previous literature suggesting there may be different "drivers" for these two symptoms dimensions (Kofler, M. J., et al., JOURNAL OF ABNORMAL CHILD PSYCHOLOGY (2010); M. M. Martel et al., 2009; Shiels & Hawk, 2010).

Subgroups Showed Functional Connectivity Differences Among their Brain Imaging Data Any machine learning model, in particular those using cross-validation, can further validate identified subgroups (Eric Feczko et al., 2019). This validation can be accomplished using independent participants in a unique sample. In the absence of such a cohort, independent data within the same participants can be used. Because multiple brain regions have been implicated in the various EF processes (Alexander, A. S., et al., NATURE NEUROSCIENCE. (2015); Braga, R. M., et al., NEURON (2017); Braunlich, K., et al., NEUROIMAGE (2015); Corbetta, M., et al., *Nature Reviews. Neuroscience,* 3(3), 201-215 (2002); Dosenbach, N. U. F., et al., PROCEEDINGS OF THE NATIONAL ACADEMY OF SCIENCES OF THE UNITED STATES OF AMERICA, 104(26), 11073-11078 (2007); N. U. Dosenbach, N. U., et al., The network structure of task control. In SOCIETY FOR NEUROSCIENCE (Vol. Abstract). Atlanta, Ga. (2006); Fox, et al., PROCEEDINGS OF THE NATIONAL ACADEMY OF SCIENCE, 102(27), 9673-9678 (2005); Leech, R., et al., THE OFFICIAL JOURNAL OF THE SOCIETY FOR NEUROSCIENCE (2011); Lin, H. Y., et al., JOURNAL OF THE INTERNATIONAL NEUROPSYCHOLOGICAL SOCIETY (2015); Power, J. D., et al., NEURON, 72(4), 665-678 (2011); Seeley, W. W., et al., JOURNAL OF NEUROSCIENCE, 27(9), 2349-2356 (2007); Vann, S. D., et al., NATURE REVIEWS NEUROSCIENCE (2009); Zhang, R., et al., BRAIN STRUCTURE AND FUNCTION, 222(9), 3973-3990 (2017)), the methods of Example 5 were further validated using neuroimaging data as derived from rs-fMRI.

The Subgroups Showed Differences within and Between Many Functional Networks Implicated in EF The identified subgroups identified in Example 5 and the TD group significantly differed from one another both within and between functional networks related to EF. In the hyperactive model, notable differences were found between the HSG-Mild, HSG-Severe, and TD group within and between brain regions associated with attention (salience (SaI), DoA) (Corbetts & Shulman, 2002; Power et al., 2011; Seeley et al., 2007), response inhibition (ventral attention (VeA)) (Zhang et al., 2017) and motor activity (somatosensory motor, ventral "mouth" (SMm, somatosensory motor, dorsal "hand" (SMh)) (FIG. 5a) (Power et al., 2011). These findings highlight the potential implications for the SMm+SMh, attentional, and response inhibition networks and their relationship to EF domains, such as behavioral regulation and initiation, which were shown to be different between groups (Table 6, FIGS. 35A and 35B).

For the inattentive model, the ISG-Mild, ISG-Severe, and TD groups showed significant differences within and between networks associated with task-positive (cingulo-opercular (CiO), DoA) (Fair, D. A., et al., PROCEEDINGS OF THE NATIONAL ACADEMY OF SCIENCES OF THE UNITED STATES OF AMERICA, 104(33), 13507-13512 (2007)) and attentional networks (SaI, DoA.) (FIG. 39B). This is consistent with the findings showing significant performance differences on measures related to task control initiation and organization (Table 7, FIGS. 39A and 39B). There were also several differences seen between the task-negative (Def) (Braga & Buckner, 2017; Fox et al., 2005; Leech et al., 2011) and multiple sensory networks including motor (SMm, SMh), visual (Vis), and auditory (Aud). This difference in task negative and sensory networks may suggest varying strategies participants engage to manage their attention to internal and external stimuli.

Unlike Behavior, Subgroups Did not Follow a "Severity Trend" Across Functional Brain Networks Another interesting finding in the imaging data was that unlike the behavior, the subgroups did not appear to follow a clinical 'severity trend' across functional brain networks. This is helpful in suggesting true configural types as opposed to merely recapturing severity. At the same time it may seem counterintuitive. It might be expected, for example, that for any given network the TD group would show the most connectivity between regions, followed by high-performers, followed by low-performers, or vice-versa. However, the majority of within and between network connections observed in Example 5 did not follow this pattern. Rather, multiple patterns of connectivity were present in the data (FIGS. 39A and 39B). These results demonstrate that despite identification of lower (HSG-Severe, ISG-Severe) and higher (HSG-Mild, ISG-Mild) performing groups, such behavioral manifestations are not entirely attributable to a global theme of over- or under-connected functional networks per group, suggesting a more intricate mechanistic interaction.

As demonstrated in Example 5, specific complex patterns of brain interactions do not map one to one with a more or less optimal state (Holmes, A. J., et al., TRENDS IN COGNITIVE SCIENCES (2018)). To further explain, consider a simple example. Imagine a study whereby the goal was to identify the factors attributable to the length of time participants were able to stay upright on a balance beam. To identify characteristics, participants may be split into 'good' and 'bad' balancers. On the one hand, participants who practice balancing are better balancers than those who do not—i.e., more practice equates to a better balancer. In this case the 'cause' of good or bad follows the same pattern, along the dimension of more or less practice. On the other hand, the bad-balancers may have just simply had their eyes closed, whereby it was the lack of visual perception that made them worse at the task. In this latter case, the 'cause' does not follow the same pattern, i.e. there is no dimensional relationship with the outcome. The findings of Example 5 are more akin to the latter scenario wherein brain networks do not follow along one dimension from high to low connectivity (or vice versa) leading to high and low performers; rather, a fundamentally different organization is seen between the high and low performing subgroups.

Example 6: Generating Maternal Perinatal Stress Trajectories Using a Functional Random Forest Model Introduction Maternal psychological stress during pregnancy is a common and potentially modifiable risk factor for offspring psychiatric disorders. Little is known about how the heterogeneity of stress across pregnancy affects brain systems and behavioral phenotypes in infancy. Example 6 examines the relationship of maternal trajectories to newborn resting state functional connectivity and negative affect development over the first two years of life. The Functional Random Forest model was used to create maternal perinatal stress trajectories from early pregnancy to 1 month postpartum. A first trajectory characterized by peak stress in late pregnancy was associated with stronger amygdala to anterior insula and ventromedial prefrontal cortex functional connectivity. A second trajectory characterized by increasing stress in late pregnancy was associated with stronger amygdala to ventromedial prefrontal cortex connectivity and an altered trajectory of infant negative affect development. Understanding the heterogeneity of perinatal stress and its influence on infant brain and behavioral development is critical to targeting interventions.

Maternal psychological stress during pregnancy (e.g., anxiety, depression, and perceived stress) has implications for maternal health and is a common and potentially modifiable risk factor for offspring psychiatric and other health disorders. Previous studies of maternal psychological stress during pregnancy primarily consider stress in terms of its magnitude (i.e., high, medium, or low). However, several lines of evidence highlight the dynamic nature of psychosocial stress over the course of pregnancy (Buss C, et al., CEREBRUM (2012); Mora P A, et al., AM J EPIDEMIOL, 169(1): 24-32 (2009); Ahmed A, et al., BMC PREGNANCY CHILDBIRTH, 19(1):26 (2019)). Despite such evidence, there is a limited understanding of how the individual differences or heterogeneity in maternal psychological stress across pregnancy relate to offspring neurodevelopment. Fetal neurodevelopment is a dynamic process that is differentially sensitive to environmental influences during distinct phases. Thus, it is likely that the effect of any insult, such as maternal stress, may depend just as much on timing and rate of change as it does on severity.

The fetus receives cues about the extrauterine environment via stress-sensitive aspects of maternal-placental-fetal biology (Buss, et al; Graham A M, et al., BIOL PSYCHIATRY, 85(2):172-181 (2019); Sandman C A, et al., NEUROENDOCRINOLOGY, 95(1):7-21 (2012); Sandman C A, et al., NEUROENDOCRINOLOGY, 95(1):7-21 (2012); Entringer S, et al., CURR OPIN ENDOCRINOL DIABETES OBES. 17(6):507-516 (2010), potentially influencing brain systems sensitive to stress and commonly implicated in neuropsychiatric disorders. For example, maternal psychological and biological stress mediators during pregnancy have been associated with altered offspring limbic-prefrontal system development in infancy (Graham A M, et al., BIOL PSYCHIATRY 83(2):109-119 (2018); Qiu A, et al., TRANSL PSYCHIATRY, 5 (2015); Rifkin-Graboi A, et al., J AM ACAD CHILD ADOLESC PSYCHIATRY, 54(4):313-321 (2015); Qiu A, et al., TRANSL PSYCHIATRY, 3(9):e306-e306 (2013); Rifkin-Graboi A, et al., BIOL PSYCHIATRY, 74(11):837-844 (2013); Qiu A, et al., CEREB CORTEX, 27(5):3080-3092 (2017)). Because the limbic-prefrontal system plays an important role in the regulation of stress and negative affect, these stress-induced alterations may increase the risk for emotional and behavioral dysregulation (Tottenham N, et al., DEV SCI. 14(2):190-204 (2011); Herringa R J, et al., PROC NATL ACAD SCI USA. 110(47):19119-19124 (2013); Callaghan B L, et al., DEV PSYCHOBIOL., 56(8):1635-1650 (2014); Burghy C A, et al., NAT NEUROSCI. 15(12):1736-1741 (2012); Banks S J, et al., SOC COGN AFFECT NEUROSCI. 2(4):303-312 (2007); Morawetz C., et al., SOC COGN AFFECT NEUROSCI., 12(4):nsw169 (2016); Buss C, et al., PROC NATL ACAD SCI USA., 109(20):E1312-9 (2012); Rogers C E, et al., J AM ACAD CHILD ADOLESC PSYCHIATRY, 56(2):157-166 (2017)), heightened negative affect and stress reactivity (Davis E P, et al., PRENATAL MATERNAL ANXIETY AND DEPRESSION PREDICT NEGATIVE BEHAVIORAL REACTIVITY IN INFANCY (1986); Davis E P, et al., J CHILD PSYCHOL PSYCHIATRY, 52(2):119-129 (2011); Yong Ping E, et al., PSYCHONEUROENDOCRINOLOGY, 56:62-78 (2015)), and subsequent psychopathology (Etkin A, et al., AM J PSYCHIATRY, 164(10):1476-1488 (2007); Roy A K, et al., J AM ACAD CHILD ADOLESC PSYCHIATRY, 52(3):290-299.e2 (2013); Gold A L, et al., DEPRESS ANXIETY, 33(10): 917-926 (2016); Hahn A, et al., NEUROIMAGE, 56(3):881-889 (2011); Prater K E, et al., DEPRESS ANXIETY, 30(3):234-241 (2013); Kim M J, et al., CEREB CORTEX, 21(7):1667-1673 (2011)). Alterations in limbic-prefrontal system function and associated increases in negative emotionality are of particular interest as transdiagnostic indicators of susceptibility for psychiatric disorders (Insel T R, AM J PSYCHIATRY, 171(4): 395-397 (2014); Insel T, et al., AM J PSYCHIATRY, 167(7):748-751 (2010)).

Figure 40:
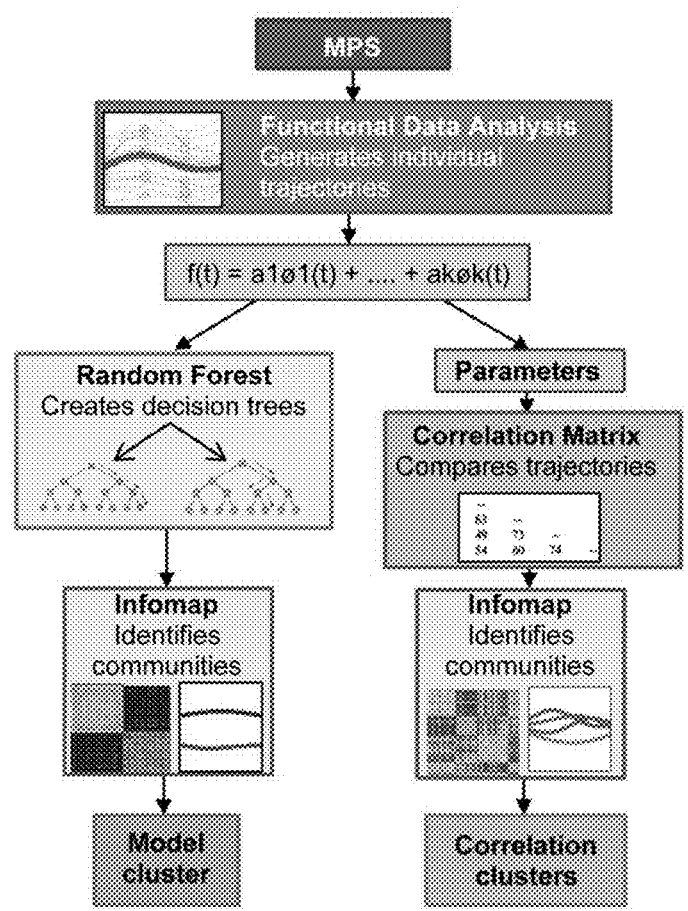
FIG. 40 illustrates a diagram of the FRF model utilized in Example 6 to characterize individual longitudinal trajectories of maternal prenatal and early postpartum stress and to identify heterogeneous subgroups.

Fetal neurodevelopment follows a rapid and sequential progression; therefore, characterizing the timing and variability of maternal stress across pregnancy is a critical step in advancing our understanding of stress as an early influencer of offspring brain and behavioral development. Example 6 therefore employs a novel, flexible and data-driven approach to characterize individual longitudinal trajectories of maternal prenatal and early postpartum stress and identify heterogeneous subgroups. FIG. 40 illustrates a diagram of the FRF model utilized in Example 6 to characterize individual longitudinal trajectories of maternal prenatal and early postpartum stress and to identify heterogeneous subgroups. The FRF model combines functional data analysis, the Random Forest, and Infomap to characterize subgroups within populations. Self-report measures of maternal perinatal stress (MPS) were used to create model and correlation clusters. Example 6 reports testing of the associations between these subgroups and infant amygdala and affective development.

Results

Maternal Trajectories of Perinatal Stress

Approach 1. Model-Based Clustering Captures Magnitude

Figure 41A:
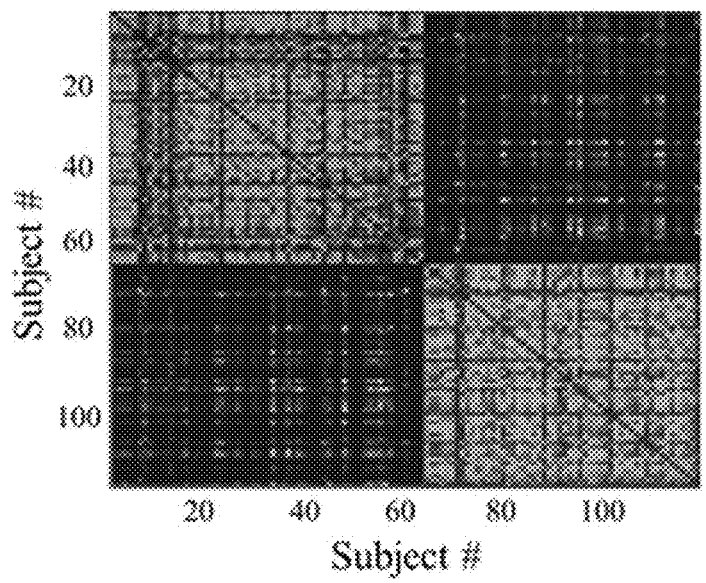
FIGS. 41A and 41B illustrate FRF-identified distinct subgroups in accordance with Approach 1.
Figure 41B:
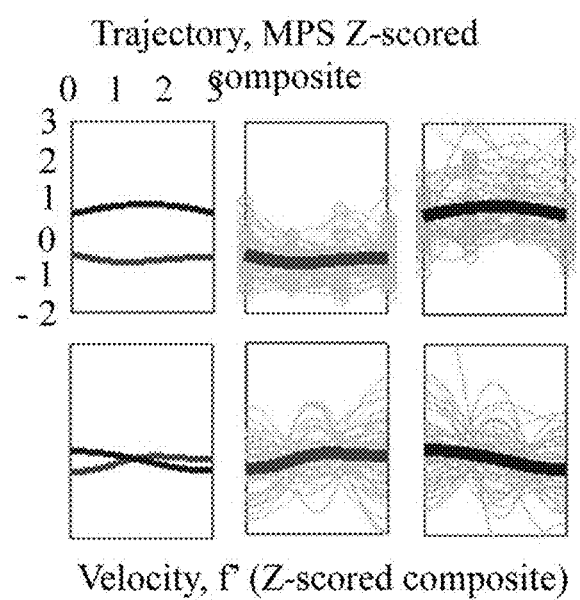

Maternal perinatal composite stress scores from 115 mothers were entered into the FRF model. FIGS. 41A and 41B illustrate FRF-identified distinct subgroups in accordance with Approach 1. FIG. 41A illustrates a sorted proximity matrix for the model-based approach. FIG. 41B illustrates two distinct trajectories reflecting high/low maternal perinatal stress from the model-based approach. In FIG. 41B, the top row shows individual stress trajectories with central tendency of each cluster in bold. Group 1 (red) had lower maternal perinatal stress scores. Group 2 (blue) had higher scores and greater variability. The bottom row of FIG. 41b shows the velocity of perinatal stress with central tendency of each cluster in bold. The left column shows the central tendency of the clusters.

As illustrated in FIG. 41A, the Model-based approach identified two clusters, divided nearly evenly, with a third cluster containing only one subject who was excluded from analysis ($Q=0.125$, $p=0.009$). The two remaining clusters captured magnitude differences in maternal perinatal stress ($t(1998)=113.47$, $p<0.001$, CI 0.414, 0.429), see FIG. 41A. These clusters, which differed measurably at every time point in a two-way ANOVA (all $p<0.001$), reflected mothers with high ($Q=0.247$, $p=0.001$) and low ($Q=0.247$, $p=0.001$) mean composite scores. We refer to these clusters, hereafter as "magnitude clusters." FIG. 41B illustrates plots of the associated trajectories of the magnitude clusters, which reflect the high/low split. The mean velocities of the two clusters were similar and mostly flat because they encompassed participants with varying trajectories.

Figure 42A:
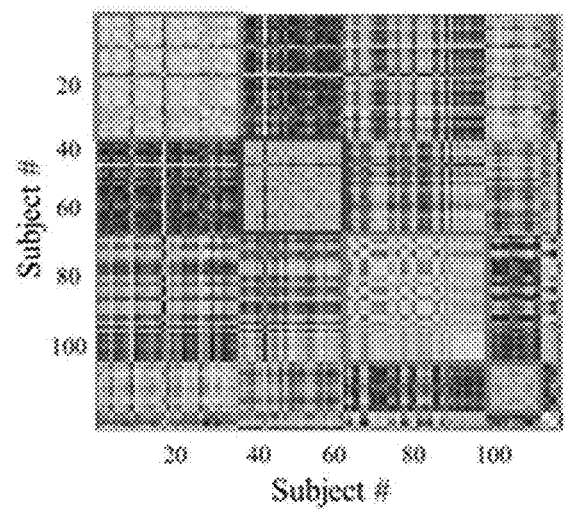
FIGS. 42A and 42B illustrate FRF-identified distinct subgroups in accordance with Approach 2.
Figure 42B:
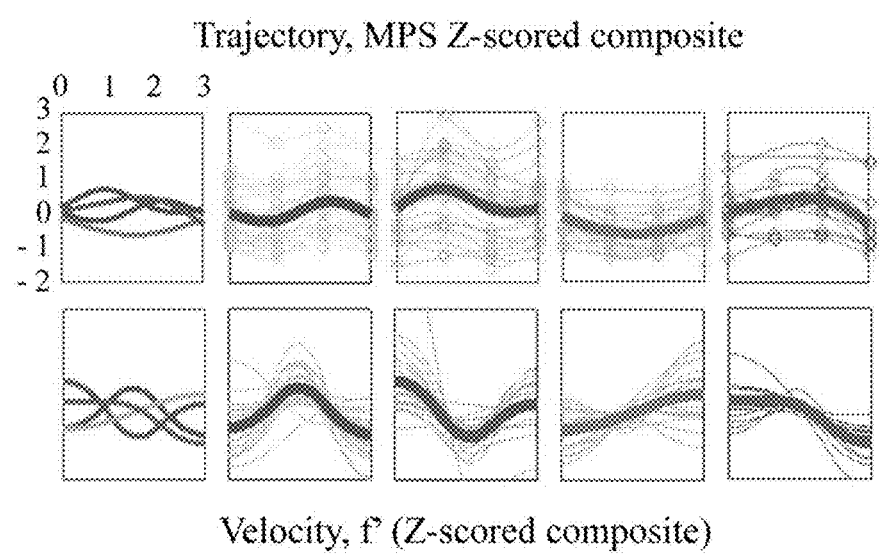

Approach 2. Correlation-Based Clustering Captures Shape and Velocity of Maternal Perinatal Stress The correlation-based approach utilized the same participants as Approach 1. FIGS. 42A and 42B illustrate FRF-identified distinct subgroups in accordance with Approach 2. In Approach 2, maternal perinatal stress measures were completed during early (0), mid (1), and late (2) pregnancy, and 1 month postnatal (3). FIG. 42A illustrates a sorted proximity matrix for the correlation-based approach. FIG. 42B illustrates the four distinct trajectories used in the correlation-based approach, which reflect differences in peak stress. The top row illustrates individual stress trajectories with the central tendency of each cluster in bold. The bottom row shows the velocity of perinatal stress with the central tendency of each cluster in bold. The left column shows the central tendency of the clusters.

As shown in FIGS. 42A and 42B, this analysis identified four Correlation-based clusters with distinct trajectories defined by the shape and velocity of changes in maternal perinatal stress. We hereafter refer to these clusters as "trajectory clusters". Clusters with less than 10 subjects were not considered reliable and were excluded from further analyses. The final trajectory clusters accounted for 102 mothers. The 13 mother-infant dyads that belonged to clusters excluded from the analyses did not differ significantly from those included.

FIG. 42B shows the shapes of the trajectories. Trajectory 1 ($Q=0.221$, $p=0.001$) demonstrated a sideways s-shape with lower stress at second trimester and a peak stress at the third trimester. The velocity for trajectory 1 was highest between the second and third trimester indicating the greatest change in stress level across this period. The opposite pattern was present in trajectory 2 (Q=0.202, p=0.001), which showed an early peak in stress at the second trimester followed by a decrease in stress in the third trimester. This trajectory also showed the greatest change between the second and third trimester, but in a direction opposite to trajectory 1, indicating a decrease in stress. Trajectory 3 (Q=0.170, p=0.001) was u-shaped with a trough at the second trimester increasing across the third trimester. The velocity of trajectory 3 demonstrated increasing stress across the third trimester to the first postnatal month. Finally, the shape and velocity of trajectory 4 (Q=0.154, p=0.001) both reflected a shallow initial rise followed by a drop-off in stress from the third trimester to the first postnatal month.

Maternal Perinatal Stress Clusters are Associated with Infant Functional Connectivity To examine the effects of the maternal clusters on infant outcomes we evaluated both neonatal offspring brain connectivity, and longitudinal relationships to offspring negative affect development through 2 years of age. Maternal clusters were dummy coded and included as predictors in all analyses. Non-significant associations between covariates and maternal stress clusters are reported in the Supplement.

Figure 43A:
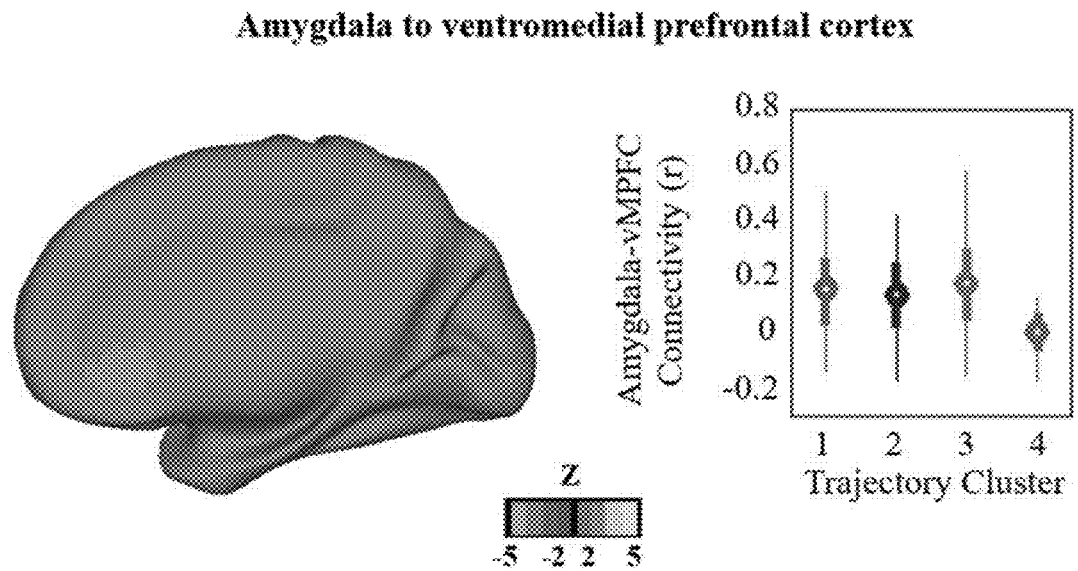
FIGS. 43A and 43B illustrate that maternal perinatal stress trajectory clusters are associated with neonatal infant amygdala connectivity.
Figure 43B:
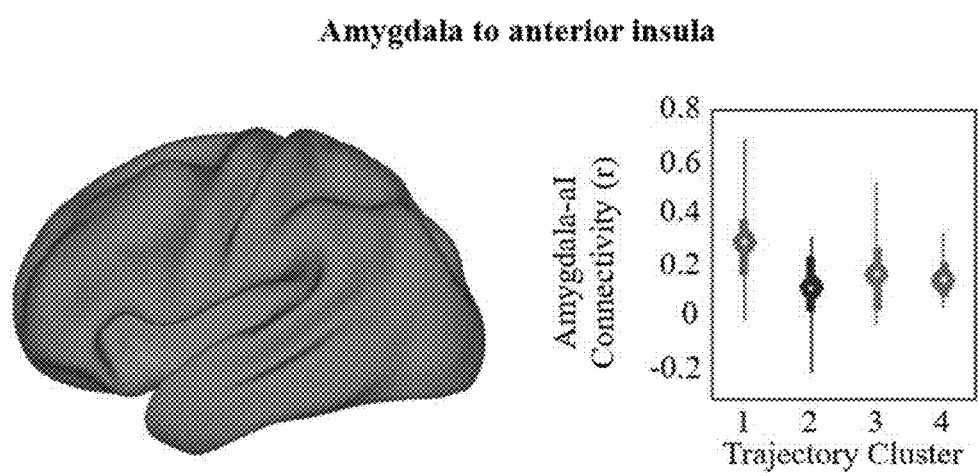

FIGS. 43A and 43B illustrate that maternal perinatal stress trajectory clusters are associated with neonatal infant amygdala connectivity. Both panels show results for left amygdala. Covariates for gestational age at birth and infant age at scan were included to account for neonatal brain maturity at the time of MRI scan acquisition. Correlation values are reported for amygdala functional connectivity (r). Circles represent cluster means. Bolded color bars represent interquartile range (25th to 75th percentile) and thin lines represent data from the 2.5th to 97.5th percentile. In FIG. 43A, trajectory clusters 1 and 3 were associated with increased connectivity to the ventromedial prefrontal cortex (vMPFC). Am-vMPFC connectivity for trajectory 2 approached significance (B=0.127, p=0.069), but demonstrated greater variance than trajectory 1 and a lower mean than both trajectories 1 and 3. In FIG. 43B, trajectory cluster 1 was associated with increased connectivity to the bilateral anterior insula (aI).

The magnitude clusters, capturing symptom severity, were not associated with neonatal Am-vMPFC (B=0.015, p=0.746) or Am-aI (B=0.008, p=0.841) functional connectivity; however, the trajectory clusters showed significant associations with amygdala connectivity. Trajectory 1, was significantly associated with stronger Am-vMPFC (B=0.173, p=0.011) and Am-aI (B=0.166, p=0.006) connectivity (see FIGS. 43A and 43B). Trajectory 3 also predicted stronger Am-vMPFC connectivity (B=0.172, p=0.011), see FIG. 43A. Although Trajectory 3 does not demonstrate peak stress during the third trimester, as seen in Trajectory 1, stress is increasing during this time. Trajectory 2 and 4 did not predict alterations in Am-vMPFC or Am-aI connectivity.

Maternal Perinatal Stress Clusters are Associated with Infant Negative Affect Growth The association between maternal perinatal stress clusters and infant negative affect development was examined by adding perinatal stress clusters as predictors, along with relevant covariates, to the LGM model of negative affect from 3-24-months-of-age.

Figure 44A:
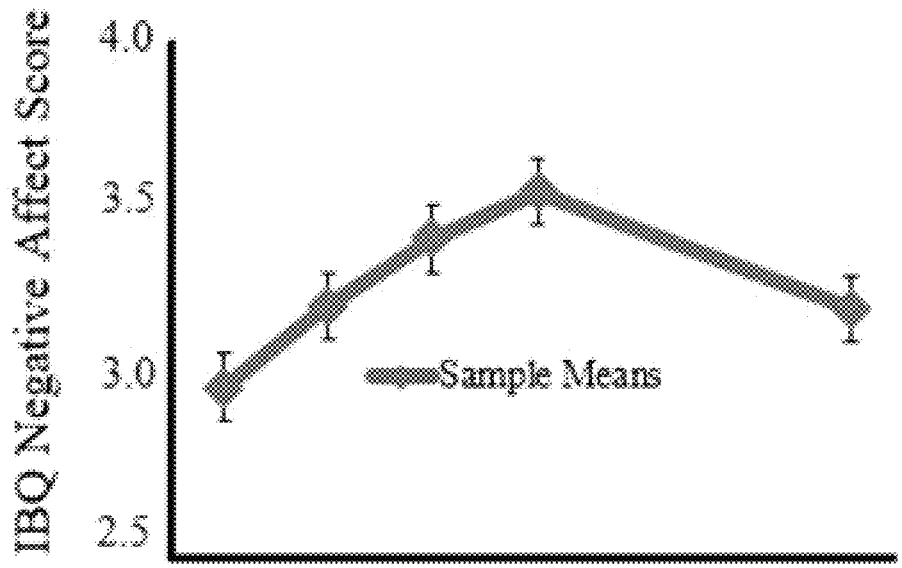
FIGS. 44A and 44B illustrate that infant negative growth has an inverted u-shaped trajectory.
Figure 44B:
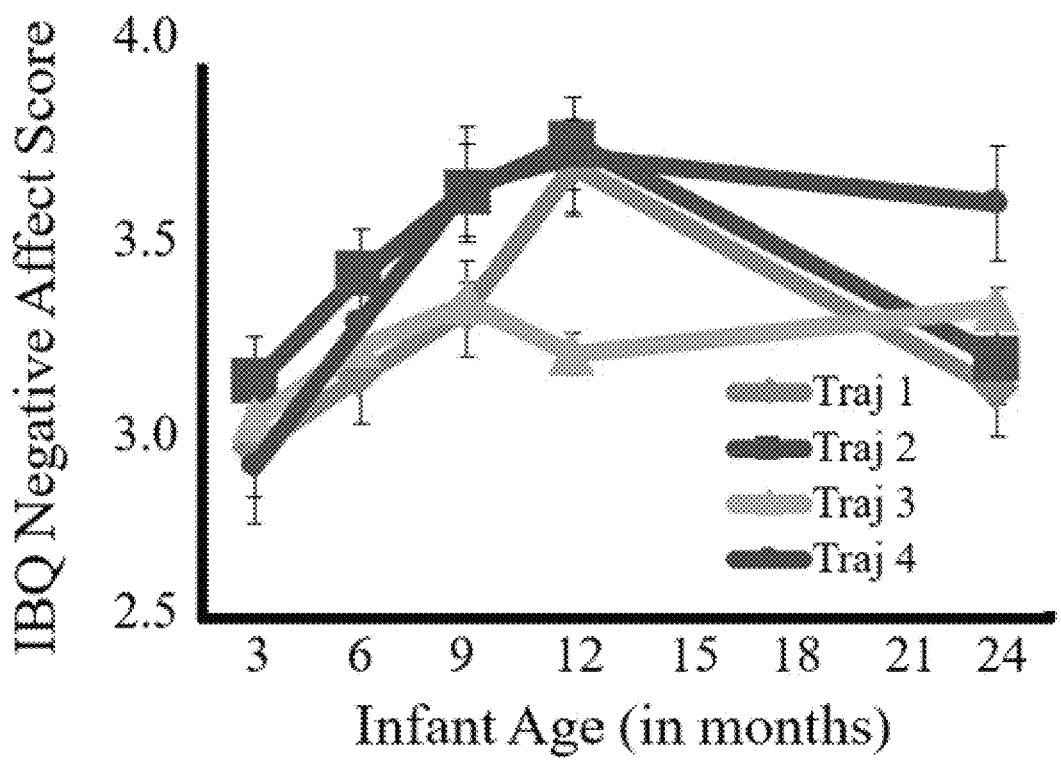

FIGS. 44A and 44B illustrate that infant negative growth has an inverted u-shaped trajectory. FIG. 44A illustrates an unconditional model of IBQ negative affect. The quadratic shape in this model reflects an increase in negative affect until 12 months of age with scores then decreasing through 24 months of age, as described by the significant negative mean of the quadratic term (M=−0.421, p<0.001). FIG. 44B illustrates maternal trajectory clusters. Trajectory cluster 3 independently predicts the slope of infant negative affect growth. Maternal trajectory 3 (orange) differs significantly from the other clusters at 12 months of age (t=−2.841, p=0.01).

Magnitude clusters. The magnitude clusters predicted the intercept term (B=0.339, p=0.008) suggesting that higher maternal perinatal stress throughout pregnancy is related to elevated infant negative affect at 3 months of age. When adjusting the models for maternal postnatal stress scores, magnitude clusters no longer predicted infant negative affect at the intercept suggesting that postnatal maternal stress at 3 months of infant age may explain the relationship between maternal perinatal stress and infant negative affect.

Trajectory clusters. Maternal trajectory clusters did not predict intercept. However, Trajectory 3 predicted less linear growth (B=−0.918, p=0.032) of infant negative affect growth (FIG. 44B). When adjusting for maternal postnatal stress scores, Trajectory 3 continued to measurably predict the linear term of infant negative affect development (B=−0.921, p=0.031). The plot of infant negative affect development (FIG. 44B) suggests that infants of mothers in the Trajectory 3 cluster show an overall divergent pattern of negative affect development, beginning at approximately 12 months of age. The level of negative affect was found to be significantly different between Trajectory 3 and the others clusters at 12-months (t=−2.841, df=69, p=0.01).

Discussion

Example 6 demonstrates that trajectories of maternal perinatal stress were related to infant brain phenotypes and negative affect development over the first two years of life. Overall, the data highlight that the trajectory of maternal perinatal stress contributes to offspring brain and affective development. To many in the field, the finding that maternal psychological stress during pregnancy is related to infant emotional development, especially negative emotionality, is not surprising given the extant literature in this area.

The large majority of these prior studies only consider the magnitude of stress. Example 6 show that heterogeneity exists in maternal stress during pregnancy, with regard to magnitude, timing and rate of change. Importantly, when grouping women by overall magnitude of stress versus the timing and rate of change in stress (trajectory), the trajectory appears to be more important for offspring brain and behavioral development.

These findings can be considered in two ways in the context of the current literature: 1) that the entire trajectory is an important parameter for offspring development that needs to be considered, and 2) in the absence of the trajectory (i.e. when studies only sample one time point), the time when that sample was taken is also critically important. Follow-up analyses of each perinatal time point separately indicate that it is likely the former, at least with regard to the brain outcomes. Results for infant behavior indicated that sampling in the second or third trimester may be more likely to reveal associations between prenatal stress and infant negative affect development.

Both Trajectory 1 and Trajectory 3 had either peaks or increases in maternal stress in the third trimester. Both of these trajectories related strongly to amygdala connectivity and negative affect in offspring. It is possible that the increase in stress at the end of pregnancy has a unique impact compared to consistently high levels of maternal stress throughout pregnancy. These results suggest this is the case as the overall magnitude of stress was included in the same model along with the trajectories. In fact, previous studies suggest that maternal responsivity to stress is often dampened as pregnancy progresses supporting the idea that the timing of stress in pregnancy is relevant for offspring development (Sandman C A, et al., NEUROENDOCRINOLOGY, 95(1):7-21 (2012); de Weerth C, et al., NEUROSCI BIOBEHAV REV. 29(2):295-312 (2005); Entringer S, et al., Stress, 13(3): 258-268 (2010); Glynn L M, et al., HEAL PSYCHOL., 27(1): 43-51 (2008)). Rapid cortical maturation, circuit formation, and increased neuronal connectivity, which are hallmarks of this developmental period (Andescavage N N, et al., CEREB CORTEX. 27(11):5274-5283 (2016); Vasung L, et al., J ANAT., 217(4):400-417 (2010); Vasung L, et al., NEUROIMAGE, 187: 226-254 (2019); Tau G Z, et al., NEUROPSYCHOPHARMACOLOGY, 35(1):147-168 (2010); Rice D, et al., ENVIRON HEALTH PERSPECT, 108(suppl 3):511-533 (2000); Gao W, et al., BRAIN STRUCT FUNCT., 220(2):1173-1186 (2015); Thomason M E, et al., DEV COGN NEUROSCI. 11:96-104 (2015)), might be one reason why this period is particularly sensitive to increases in maternal stress Trajectory 2 demonstrated the lowest stress during the third trimester and was not associated with neonatal functional connectivity. Similarly, negative affect growth in the offspring of trajectory 2 mothers followed the expected developmental pattern (FIG. 44A; see also (Graham A M, et al., DEV COGN NEUROSCI, 18:12-25 (2016); Thomas E, et al., DEV COGN NEUROSCI., 37:100604 (2019); Garstein M, et al., INFANT BEHAV DEV., 26:64-86 (2003); Partridge T, et al., INFANT CHILD DEV., 16(3):255-265 (2007); Braungart-Rieker J M, et al., DEV PSYCHOL., 46(4):791-804 (2010); Brooker R J, et al., DEV SCI., 16(6):864-878 (2013)). The fact that the offspring of trajectory 2 mothers showed typical patterns of brain and behavioral development in early life compared to other trajectories further emphasizes the importance of late pregnancy and its influence on outcomes.

There are several limitations to consider. First, maternal stress was characterized using self-report measures. Although not a diagnostic interview, the use of self-report measures to characterize stress is clinically relevant given that this is how depression and anxiety are typically monitored during routine prenatal care. Similarly, infant behavior was based on maternal-report measures. Infant emotions are difficult to assess and could reflect maternal mood, expectations, or recall. We addressed this limitation by including maternal stress at each infant behavior time point as a covariate.

The identified trajectories provide information on the timing and variability of stress during pregnancy. Importantly, the trajectory clusters identified by the FRF differed in terms of the timing of peak stress and changes in the rate of stress across pregnancy. Recognizing the sequential process of neurodevelopment, it is possible that these alterations in psychological stress have a differential impact on brain development depending on the timing of peak stress or change. Example 6 illustrates that maternal perinatal stress trajectories were related to both infant neurodevelopment and psychosocial development. These maternal perinatal stress trajectories may provide insight into early childhood developmental trajectories, potentially highlighting infant risk or sensitivity. Understanding the heterogeneity of perinatal psychological stress and its influence on infant neurobiological and psychosocial development is critical to targeting preventive interventions.

Methods and Materials

Participants

Mothers and infants were part of a prospective longitudinal study conducted at the University of California, Irvine (see Moog N K, et al., BIOL PSYCHIATRY, 83:120-127 (2018)). Mothers were recruited during their first trimester of pregnancy. A subset of mothers (n=115) was selected based on the completion of maternal stress measures in early pregnancy and at one month postpartum. All procedures were approved by the Institutional Review Board at the University of California, Irvine.

Maternal Psychological Stress Measures

Participants completed the Center for Epidemiological Studies Depression Scale (CESD) (Radloff L S, APPL PSYCHOL MEAS, 1(3):385-401 (1977)), Perceived Stress Scale (PSS) (Cohen S, et al., J HEALTH SOC BEHAV., 24(4):385 (1983)), and State-Trait Anxiety Inventory (STAI) (Spielberger C D, et al., MANUAL FOR THE STATE-TRAIT ANXIETY INVENTORY (1970)) in early (M: 12.84, SD: 1.83 weeks), mid (M: 20.50, SD: 1.44 weeks) and late (M: 30.48, SD: 1.39 weeks) pregnancy and at 1, 3, 6, 9, 12, and 24 months postpartum. Early-, mid-, and late pregnancy, and one-month postpartum maternal z-transformed composite stress scores were generated based on these 3 scales in order to create an overall indicator of maternal psychological stress at each time point from early pregnancy through early postpartum. Measures at each time point were highly correlated (r: 0.359 to 0.817, p<0.01), supporting our creation of a composite indicator. Postnatal maternal composite stress scores from 3 to 24 months were used as covariates in analyses examining infant behavior in order to adjust for the potential influence of the postnatal environment.

Resting-State Functional Connectivity MRI

Infant neuroimaging data were acquired at approximately one month of age (28.42±13.31 days) during natural sleep. Data acquisition and preprocessing procedures were previously described (Graham A M, et al., BIOL PSYCHIATRY 83(2): 109-119 (2018); Moog N K, et al., BIOL PSYCHIATRY, 83:120-127 (2018); Graham A M, et al., DEV COGN NEUROSCI, 18:12-25 (2016); Rudolph M D, et al., NAT NEUROSCI., 21(5):765-772 (2018)). Previously, patterns of increased neonatal amygdala connectivity with the ventromedial prefrontal cortex (vMPFC) and anterior insula (aI) have been identified, which predicted infant negative affect development (Graham A M, et al., DEV COGN NEUROSCI, 18:12-25 (2016); Thomas E, et al., DEV COGN NEUROSCI., 37:100604 (2019)). Example 6 focused on these predefined amygdala connections due to prior work indicating the vulnerability of the amygdala to early life stress exposure, beginning in the prenatal period (Thomas E, et al., DEV COGN NEUROSCI., 37:100604 (2019); Graham A M, et al., DEV COGN NEUROSCI., 18:12-25 (2016)).

Data Acquisition

A TIM Trio, Siemens medical System 3.0T scanner was used to obtain High-resolution T1-weighted (MP-RAGE TR=2400 ms, inversion time=1200 ms, echo time=3.16 ms, flip angle=8°, resolution=1×1×1 mm, 6 min 18 secs) and T2-weighted (TR=3200 ms, echo time=255 ms, resolution=1×1×1 mm, 4 min 18 secs) images. Resting-state functional connectivity (rs-FC) MRI images were obtained using a gradient-echo, echoplanar imaging (EPI) sequence sensitive to blood oxygen level-dependent (BOLD) contrast (TR=2000 ms; TE=30 ms; FOV=220×220×160 mm; flip angle=77°).

fMRI Data Preprocessing

Pre-processing followed established for neonatal neuroimaging (Graham A M, et al., DEV COGN NEUROSCI., 18:12-25 (2016)). Briefly, brain images were isolated from surrounding head tissue and functional images were pre-processed to reduce artifacts. Atlas transformation involved calculation of a single matrix to facilitate registration to a standard infant template (0- to 2-month age range; National Institutes of Health MRI Study of Normal Brain Development) (Fonov V, et al., NEUROIMAGE, 54(1):313-327 (2011); Fonov V, et al., NEUROIMAGE, 47:S102 (2019)) and to the Talairach coordinate system (TALAIRACH, J., CO-PLANAR STEREOTAXIC ATLAS OF THE HUMAN BRAIN-3-DIMENSIONAL PROPORTIONAL SYSTEM. AN APPROACH TO CEREB IMAGING (1988)).

rs-fcMRI Preprocessing

Additional preprocessing steps were conducted to address potential signal stemming from non-neuronal processes including temporal low-pass filtering (0 f<0.1 Hz) (Fair D A, et al., FRONT SYST NEUROSCI., 6:80 (2012); Fox M D, et al., NAT REV NEUROSCI., 8(9):700-711 (2007)), regression of rigid body head motion parameters in 6 directions, regression of whole brain signal, regression of average ventricular signal, regression of white matter signal, and regression of first order derivative terms for the whole brain, ventricular, and white matter signals (Graham A M, et al., DEV COGN NEUROSCI, 18:12-25 (2016); Rudolph M D, et al., NAT NEUROSCI., 21(5):765-772 (2018)). To correct for motion, an examination of frame-wise displacement (FD) was conducted and volumes with greater than 0.3 mm FD plus the preceding volume and subsequent 3 volumes were removed (Power J D, et al., NEURON, 72(4):665-678 (2011)). Following volume removal for motion, scan length for the remaining infants (n=60) was about five and half minutes (M: 5.66 minutes, range: 4.27-6.37 minutes) with a remaining FD of 0.085 (M: 0.085, range: 0.048-0.135).

Amygdala Connections

Automatic amygdala segmentation was performed using a multi-template, multi-modality based method that combined T1 and T2 weighted high-resolution images (Wang J, et al., FRONT NEUROINFORM. (2014)). Following anterior-posterior realignment, amygdala segmentations were manually corrected using ITK-Snap (Yushkevich P, et al., NEUROIMAGE SH-(2006)). For rs-fcMRI analyses, amygdalae were transformed to atlas space based on the previously computed atlas transformation (Graham A M, et al., BIOL PSYCHIATRY 83(2):109-119 (2018)).

Infant Negative Affect

Mothers completed the Infant Behavior Questionnaire-Revised (IBQ-R) (Parade S H, et al., INFANT BEHAV DEV., 31(4):637-646 (2008)) to assess infant negative affect at 3, 6, 9, and 12 months of infant age and The Early Childhood Behavior Questionnaire-Short Form (ECBQ) (Putnam S P, et al., INFANT BEHAV DEV., 29(3):386-401 (2006); Putnam S P, et al., J PERS ASSESS, (4):445-458 (2014)) at 24 months age. A latent growth model (LGM; Mplus 8: Muthén L K, et al., MPLUS USER'S GUIDE (2017)) was used to define infant negative affect development from 3-24-months-of-age. Only subjects with identified maternal perinatal clusters (Model- and Correlation-based) and IBQ/ECBQ scores with a minimum of one time point were included in the LGM in order to better compare the unconditional and conditional models (n=110). The parameter estimates for the unconditional model are listed in the supplement. Consistent with our prior work and the literature (Graham A M, et al., DEV COGN NEUROSCI, 18:12-25 (2016); Thomas E, et al., DEV COGN NEUROSCI., 37:100604 (2019); Garstein M, et al., INFANT BEHAV DEV., 26:64-86 (2003); Partridge T, et al., INFANT CHILD DEV., 16(3):255-265 (2007); Braungart-Rieker J M, et al., DEV PSYCHOL., 46(4):791-804 (2010); Brooker R J, et al., DEV SCI., 16(6):864-878 (2013)), infant negative affect increases over the first year of life and then decreases to 24-months-of-age, forming an inverted u-shaped trajectory defined by a quadratic term with a significant negative mean (M=−0.452, p<0.001; FIG. 43A). The slope (M=1.061, p<0.001) was positive and significant, reflecting an overall increase in negative affect over time. The mean (M=2.990, p<0.001) and variance ($\sigma^2$=0.304, p<0.001) of the intercept term were also significant indicating variability in infant negative affect at 3 months of age. The intercept and growth terms from these models were used as outcome variables in analyses examining infant behavior.

Analytic Approach

The Functional Random Forest is a novel approach designed to capture unknown heterogeneity in samples, and is extended here to characterize heterogeneity of maternal perinatal stress trajectories. The approach integrates three validated techniques, Functional Data Analysis, Random Forest, and community detection (i.e., Infomap). Community detection is applied in two ways to identify (1) "Model-based clusters" or (2) "Correlation-based clusters." Both approaches capture longitudinal symptom heterogeneity in a flexible and data-driven manner. Mothers included in the model had data for at least two of the four assessments; including the first and the last time point.

The Functional Random Forest

Using two approaches, the FRF identified different symptom-associated clusters. Because the FRF makes few assumptions about the nature of the data, these clusters represent trajectories that cannot be captured using a single parametric model, such as mixture modelling used in LGMs. LGMs are very powerful approaches to identifying clusters, but require specifying how many clusters to find and the shape of the trajectories. The FRF can identify varying trajectory shapes that are not specified or explored via multiple model comparisons. Though the FRF can be a hybrid approach to identify clusters tied to a developmental or clinical outcome, Example 6 used the FRF in an unsupervised manner.

Approach 1: Model-Based Clusters

The Model-based approach to identify clusters is a hybrid approach, where a Random Forest (RF) model evaluates whether real trajectories based on the symptom data provided to the algorithm can be dissociated from artificially generated trajectories. The approach uses a combination of Functional Data Analysis (FDA), RF, and Infomap. First, FDA is employed to capture underlying trajectories present in the longitudinal data (Brumback B A, et al., J AM STAT ASSOC. 93(443):961 (1998); James G, et al., BIOMETRIKA, 87(3):587-602 (2000); Ramsay T, J R STAT SOC B., 64(2): 307-319 (2002); Hall P, et al., BIOMETRIKA, 89(1):145-158 (2002); Malfait N, et al., CAN J STAT LA WVUE CAN STAT VOl. 31(2):115-128 (2003)). Specifically, $4^{th}$ order cubic B-splines are fit to each individual's dataset and the coefficients (weights) for each individual are extracted from the best fit solution. Knots, fixed values with respect to time, are set at each of the observed time points. To limit the potential for unrealistic values (e.g. as shown by Runge's phenomenon) $2^{nd}$ order cubic B-splines form a set of cost functions, to penalize coefficients where limited data may be available. Finally, unrealistic fits are evaluated by generating a dense timeseries from the basis functions per individual. This dense timeseries represents the "trajectory" of a given individual, and timeseries that do not fall within realistic values for the measures (i.e. between X or Y) are rejected and the individual is excluded from subsequent analysis. For each individual with acceptable data, the model's coefficients are passed to the Random Forest (RF) which classifies multiple patterns or pathways in these weights using decision trees (Breiman L C A. BREIMAN AND CUTLER'S RANDOM FORESTS FOR CLASSIFICATION AND REGRESSION. Packag "random Forest."). Here, we used an unsupervised approach, meaning that the subject's stress scores were not linked to a specific outcome variable of interest, to classify between fake and real trajectories, using a 10-fold cross validation strategy repeated thrice. Fake trajectories were simulated by randomly shuffling the weights across the subjects, such that fake trajectories, show only random fluctuations with time. Null models are generated by randomly permuting the labels between fake and real trajectories and performing the same 10-fold cross-validation. The null model measures performance under the assumption that trajectories are random. If the observed model performs better than expected by the null model, then it is likely that the observed trajectories are non-random. The RF produces a similarity matrix, which represents the number of times pairs of participants traveled the same paths throughout the forest. This proximity matrix is passed into Infomap (see FIG. 40) (Feczko E, et al., NEUROIMAGE 172:674-688 (2017); Rosvall M, et al., PROC NATL ACAD SCI USA., 105(4):1118-1123 (2008)). To generate consensus communities, the proximity matrix was thresholded at multiple edge densities, from 20 to 100 percent in steps of 5 percent. Per threshold, communities were identified and a consensus community matrix was formed, where each cell represents the proportion of times two participants were in the same community. Consensus communities were identified by running Infomap on this consensus matrix.

Approach 2: Correlation-Based Clusters

The Model-based, hybrid approach described above represents one way to identify putative trajectory subtypes. However, it is possible that other, equally valid subtypes may be identified with other approaches. Therefore, Example 6 contrasts the Model-based cluster approach with another approach to examine potential differences in identified subtypes. Therefore, an alternate correlation-based approach was also used and compared with the model-based approach to see whether identified subgroups overlap, or whether it could identify new subtypes that may be important to potentially different outcomes. With the correlation-based approach, the trajectories of participants derived from FDA can be correlated from every participant to every other participant and passed into Infomap instead. From correlation-based clusters the FRF identified distinct trajectory clusters based on changes in maternal stress during the prenatal and perinatal period.

Post-hoc analyses were conducted to examine the validity of identified clusters and further characterize differences in clusters (chi-square and ANOVAs). Clusters were significant with regard to modularity (Q), indicating valid and stable subgroups.

A simple multiple regression approach was used to examine maternal stress clusters in relation to infant amygdala connections and negative affect development. Covariates for gestational age (GA) at birth and infant age at scan were included in all analyses to account for neonatal brain maturity at the time of MRI scan acquisition. Additional covariates were also tested to ensure that model results remained consistent, including infant sex, maternal annual income and maternal obstetric risk factors.

Example 7: Identifying ADHD Subgroups by Spline-Fitting

Example 7 provides an implementation of models to identify clinical trajectories (see, e.g., FIG. 9) as applied to the identification of ADHD subgroups via spline-fitting.

Figure 45:
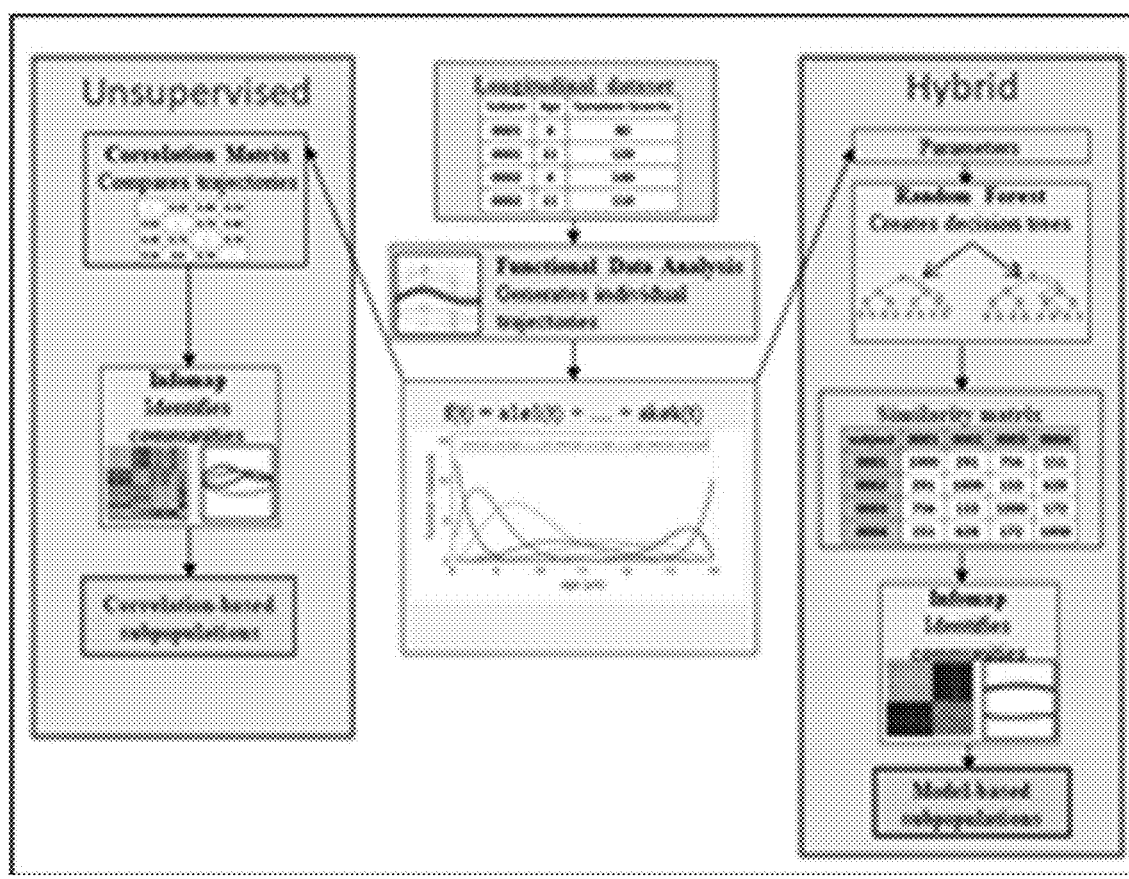
FIG. 45 illustrates a diagram of the model used to identify clinical trajectories in Example 7.

FIG. 45 illustrates a diagram of the model used to identify clinical trajectories in Example 7.

Participants: 8-14 year longitudinal measures of ADHD hyperactive and inattentive symptoms were collected across 443 individuals (see: Diagnostics below) with six timepoints. Of these participants, 92 were used in this preliminary study.

Approach: Using an approach (FIG. 45, unsupervised) influenced by FDA, and coding theory, each participant was fitted with $6^{th}$ order B-splines, with knots at each of the ages. The fits at each of the knots were penalized using a $4^{th}$ order B-spline, and the penalty weights per timepoint were estimated by calculating the root-mean-square error across the group. From the coefficient fits, the symptoms, their velocities, and accelerations per month were calculated across the age range (72 timepoints). For each participant pair, the lag-zero Pearson correlation was calculated for the expected symptoms, velocities, and accelerations. A participant-participant correlation matrix was derived by taking the mean correlation across every possible participant pair. The correlation matrix was recast as a graph, where the participants were nodes and the top 5 to 10 percent of correlations were retained as edges to maintain sparsity. Per edge density, Infomap, a coding theory approach to community detection, was used over 100 iterations to identify communities. A second graph was formed across all iterations, where participants were nodes and the edges were the number of times the two participants were in the same community, and the final putative subgroups were identified via Infomap. 32 of the participants in the first three subgroups had sufficient functional magnetic resonance imaging (MRI) data to measure the connectivity of each data point to every other data point, and to calculate the correlation of each point's connectivity vector to a large typical sample. An ANOVA was performed on this similarity measure across the cortical surface to see whether these subgroups may vary in neural mechanisms associated with ADHD.

Figure 46:
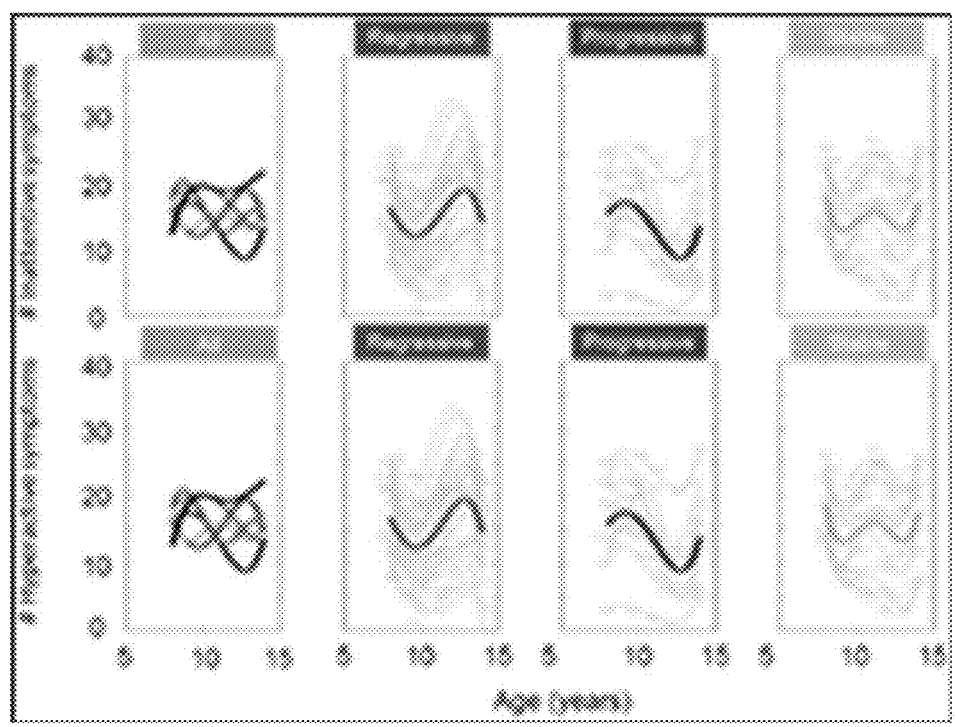
FIG. 46 illustrates a plot of symptom data for Example 7.
Figure 47:
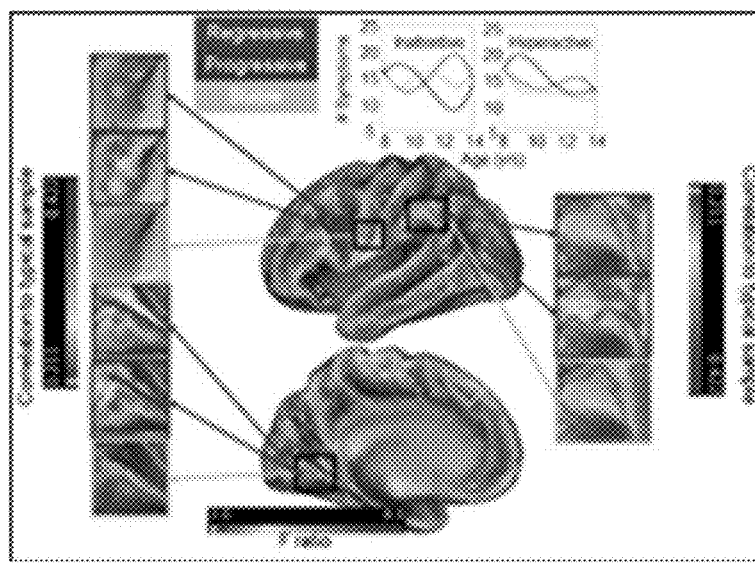
FIG. 47 illustrates an F ratio map from analysis of variance on the first three subgroups.

Results: FIG. 46 illustrates a plot of symptom data (circles). Six putative subgroups were identified across the 92 participants, and each subgroup's mean (bolded) trajectories are plotted in FIG. 46. Due to the small sample identified in the fourth, fifth, and sixth subgroups, these results focus on the first three. FIG. 47 illustrates an F ratio map from analysis of variance on the first three subgroups. Although these groups are described using progressive, regressive, and stable, these labels reflect the endpoints, but do not sufficiently characterize the trajectories revealed by the analysis. The largest subgroup (red) shows progressive symptoms that worsen through 10 years of age but start to improve afterwards. The second largest subgroup (blue) shows regressive symptoms, which improve early but then worsen as the child ages from 10 to 12. The third largest subgroup shows stable symptoms that fluctuate across development. These three subgroups show significant variation in neural mechanisms associated with ADHD (FIG. 47). Three regions implicated in ADHD and important for motor (top left), visual (bottom left), and multi-modal processing (right), show significant variation across the ADHD subgroups. such regions are therefore expected to drive classification differences between groups.

Example 7 Further Demonstrates the Utility of this Novel FDA/Infomap Approach.

Conclusions

The environments and individual elements described herein may of course include many other logical, programmatic, and physical components, of which those shown in the accompanying figures are merely examples that are related to the discussion herein. Other architectures may be used to implement the described functionality and are intended to be within the scope of this disclosure. Furthermore, although specific distributions of responsibilities are defined above for purposes of discussion, the various functions and responsibilities might be distributed and divided in different ways, depending on circumstances. Furthermore, although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

As will be understood by one of ordinary skill in the art, each embodiment disclosed herein can comprise, consist essentially of, or consist of its particular stated element(s), step(s), ingredient(s), and/or component(s). Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Explicit definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A system, comprising:
   at least one processor; and
   memory storing instructions that, when executed by the at least one processor, cause the at least one processor to perform operations comprising:
   receiving training data indicating first behavioral features of a sample population and biomarkers associated with Autism Spectrum Disorder (ASD) diagnoses of the sample population, the sample population comprising individuals;
   generating, using a supervised machine learning technique, at least 1000 decision trees in a Random Forest (RF) based on the training data, each one of the decision trees being configured to divide the individuals of the sample population into multiple categories of the ASD diagnoses based on the first behavioral features;
   in response to generating the decision trees, generating a proximity matrix comprising multiple entries using the RF, the entries indicating proportions of the decision trees that categorize pairs of the individuals into the same categories among the multiple categories;
   identifying, using an unsupervised machine learning technique, subgroups of the ASD diagnoses by detecting communities of the proximity matrix;
   receiving patient data indicating second behavioral features of a particular individual outside of the sample population;
   determining, based on the second behavioral features and the RF, that the particular individual is part of a particular subgroup among the subgroups;
   predicting, based on the particular subgroup, a treatment that will improve a prognosis of the particular individual with respect to ASD; and
   outputting, on a clinical device, an indication of the treatment.

2. The system of claim 1, wherein the first behavioral features comprise observed behaviors of the individuals in the sample population,
   wherein the second behavioral features comprise the observed behaviors of the particular individual, and
   wherein the behaviors comprise:
   a behavior related to working memory of each of the individuals;
   a behavior related to response inhibition of each of the individuals;
   a behavior related to temporal reward discounting by each of the individuals;
   a behavior related to attentional vigilance of each of the individuals;
   a behavior related to processing of a facial feature by each of the individuals;
   a behavior related to processing of a vocal affect by each of the individuals; and
   a behavior related to processing of facial emotion by each of the individuals.

3. The system of claim 1, wherein the biomarkers comprise at least one of structural Magnetic Resonance Imaging (MRI) images of brains of the individuals, functional MRI (fMRI) images of the brains of the individuals, or genotypes of the individuals, and
   wherein the patient data omits MRI images and fMRI images of the particular individual.

4. A computer-implemented method, comprising:
   identifying training data indicating features of a sample population and clinical outcomes of the sample population, the features comprising first behavioral features and biomarkers of the sample population, the clinical outcomes being associated with a heterogeneous condition, the heterogenous condition comprising a medical condition that presents as different symptoms in different patients;
   generating, using a supervised machine learning technique, decision trees in a Random Forest (RF) based on the training data, each one of the decision trees being configured to divide the sample population into multiple categories based on the features of the sample population;
   in response to generating the decision trees, generating a proximity matrix comprising multiple entries using the RF, one of the entries indicating a proportion of the decision trees that categorize a first individual among the sample population and a second individual among the sample population into the same categories among the multiple categories;
   identifying subgroups of the heterogeneous condition by detecting, using an unsupervised machine learning technique, communities of the proximity matrix;
   identifying second behavioral features of a third individual outside of the sample population;
   determining, based on the second behavioral features, that the third individual is part of a particular subgroup among the subgroups;
   predicting, based on the particular subgroup, a treatment that will improve a prognosis of the third individual with respect to the heterogeneous condition; and
   outputting, on a clinical device, an indication of the treatment.

5. The method of claim 4, wherein the heterogeneous condition comprises at least one of Autism Spectrum Disorder (ASD), Attention-Deficit/Hyperactivity Disorder (ADHD), or infant neurodevelopment.

6. The method of claim 4, wherein the heterogeneous condition comprises Autism Spectrum Disorder (ASD).

7. The method of claim 4, wherein the first behavioral features of the sample population comprise observed behaviors of the sample population, the observed behaviors comprising at least one of:
   a first behavior related to working memory of at least one third individual among the sample population;
   a second behavior related to response inhibition of the at least one third individual;
   a third behavior related to temporal reward discounting by the at least one third individual;
   a fourth behavior related to attentional vigilance of the at least one third individual;
   a fifth behavior related to processing of a facial feature by the at least one third individual;
   a sixth behavior related to processing of a vocal affect by the at least one third individual; or
   a seventh behavior related to processing of facial emotion by the at least one third individual.

8. The method of claim 4, wherein the features comprise perinatal stress of mothers of the sample population.

9. The method of claim 4, wherein the RF comprises at least 1000 decision trees.

10. The method of claim 4, wherein the unsupervised machine learning technique comprises infomap.

11. The method of claim 4, further comprising:
outputting, on the clinical device, an indication of the particular subgroup,
wherein the RF comprises at least 1000 decision trees.

12. The method of claim 4, further comprising:
outputting, on the clinical device, an indication of the particular subgroup.

13. A system, comprising:
at least one processor; and
memory storing instructions that, when executed by the at least one processor, cause the at least one processor to perform operations, comprising:
identifying training data indicating first behavioral features of a sample population, biomarkers of the sample population, and clinical outcomes of the sample population, the clinical outcomes being associated with a heterogeneous condition, the heterogenous condition comprising a medical condition that presents as different symptoms in different patients;
generating, using a supervised machine learning technique, decision trees in a Random Forest (RF) based on the training data, each one of the decision trees being configured to divide the sample population into multiple categories based on the features of the sample population;
in response to generating the decision trees, generating a proximity matrix comprising multiple entries using the RF, one of the entries indicating a proportion of the decision trees that categorize a first individual among the sample population and a second individual among the sample population into the same categories among the multiple categories;
identifying subgroups of the heterogeneous condition by detecting, using an unsupervised machine learning technique, communities of the proximity matrix;
identifying second behavioral features of a third individual outside of the sample population;
determining, based on the second behavioral features, that the third individual is part of a particular subgroup among the subgroups;
predicting, based on the particular subgroup, a treatment that will improve a prognosis of the third individual with respect to the heterogeneous condition; and
outputting an indication of the treatment.

14. The system of claim 13, further comprising:
a clinical device configured to output the indication of the treatment.

15. The system of claim 13, wherein the heterogeneous condition comprises at least one of Autism Spectrum Disorder (ASD), Attention-Deficit/Hyperactivity Disorder (ADHD), or infant neurodevelopment.

16. The system of claim 13, wherein the first behavioral features of the sample population comprise observed behaviors of the sample population, and
wherein the observed behaviors comprise at least one of:
a first behavior related to working memory of at least one third individual among the sample population;
a second behavior related to response inhibition of the at least one third individual;
a third behavior related to temporal reward discounting by the at least one third individual;
a fourth behavior related to attentional vigilance of the at least one third individual;
a fifth behavior related to processing of a facial feature by the at least one third individual;
a sixth behavior related to processing of a vocal affect by the at least one third individual; or
a seventh behavior related to processing of facial emotion by the at least one third individual.

17. The system of claim 13, wherein the first behavioral features comprise perinatal stress of mothers of the sample population.

18. The system of claim 13, wherein the unsupervised machine learning technique comprises infomap.

* * * * *